US007390894B2

(12) United States Patent
Weinshilboum et al.

(10) Patent No.: US 7,390,894 B2
(45) Date of Patent: Jun. 24, 2008

(54) GLUTATHIONE S-TRANSFERASE SEQUENCE VARIANTS

(75) Inventors: Richard M. Weinshilboum, Rochester, MN (US); Baidehi Mukherjee, Rochester, MN (US); Linda L. Pelleymounter, Rochester, MN (US); Oreste Salavaggione, St. Louis, MO (US); Eric D. Wieben, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 11/482,525

(22) Filed: Jul. 7, 2006

(65) Prior Publication Data

US 2007/0015193 A1 Jan. 18, 2007

Related U.S. Application Data

(60) Provisional application No. 60/697,128, filed on Jul. 7, 2005.

(51) Int. Cl.
*C07H 21/04* (2006.01)
*C07K 14/00* (2006.01)
*C12Q 1/68* (2006.01)
*C12Q 1/48* (2006.01)
*C12N 9/10* (2006.01)
*C12N 15/00* (2006.01)
*C12N 5/10* (2006.01)
*C01N 1/20* (2006.01)

(52) U.S. Cl. .................. 536/24.31; 435/193; 435/15; 435/320.1; 435/325; 435/252.3; 435/6; 536/23.1; 536/23.2; 536/23.5; 530/350

(58) Field of Classification Search ............... 435/193, 435/15, 320.1, 325, 252.3, 6; 536/23.1, 23.2, 536/23.5, 24.31; 530/350
See application file for complete search history.

(56) References Cited

U.S. PATENT DOCUMENTS

| 5,451,683 A | 9/1995 | Barrett et al. |
| 5,733,729 A | 3/1998 | Lipshutz et al. |
| 5,770,722 A | 6/1998 | Lockhart et al. |

FOREIGN PATENT DOCUMENTS

| WO | WO 98/20019 | 5/1998 |
| WO | WO 99/57318 | 11/1999 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Zhao et al., GenBank accession No. AZ909555, Mar. 2001.*
Lovell et al., GenBank accession No. AF389745, Aug. 2001.*
Mineta et al., GenBank accession No. BP190660, Jul. 2003.*
GenBank Accession No. NM_183239 dated Nov. 17, 2006, 3 pages.
GenBank Accession No. NT_030059 dated Aug. 29, 2006, 5 pages.
Adjei et al., "Human estrogen sulfotransferase (SULT1E1) pharmacogenetics: gene resequencing and functional genomics," *Br. J. Pharmacol.*, 2003, 139:1373-1382.
Altshuler et al., "A haplotype map of the human genome," *Nature*, 2005, 437:1299-1320.
Bardelli et al., "Mutational Analysis of the Tyrosine Kinome in Colorectal Cancers," *Science*, 2003, 300:949.
Board et al., "Identification, Characterization, and Crystal Structure of the Omega Class Glutathione Transferases," *J. Biol. Chem.*, 2000, 275(32):24798-24806.
Brodde and Leineweber, "$\beta_2$-Adrenoceptor gene polymorphisms," *Pharmacogenet. Genomics*, 2005, 15:267-275.
Chadwick et al., "Heterozygote and Mutation Detection by Direct Automated Fluorescent DNA Sequencing Using a Mutant *Taq* DNA Polymerase," *BioTechniques*, 1996, 20:676-683.
Chen et al., "Cancer potential in liver, lung, bladder and kidney due to ingested inorganic arsenic in drinking water," *Br. J. Cancer*, 1992, 66:888-892.
Drysdale et al., "Complex promoter and coding region $\beta_2$-adrenergic receptor haplotypes alter receptor expression and predict in vivo responsiveness," *Proc. Natl. Acad. Sci. USA*, 2000, 97(19):10483-10488.
Excoffier and Slatkin, "Maximum-Likelihood Estimation of Molecular Haplotype Frequencies in a Diploid Population," *Mol. Biol. Evol.*, 1995, 12:921-927.
Fullerton et al., "Apolipoprotein E Variation at the Sequence Haplotype Level: Implications for the Origin and Maintenance of a Major Human Polymorphism," *Am. J. Hum. Genet.*, 2000, 67:881-900.
Hacia et al., "Detection of heterozygous mutations in *BRCA1* using high density oligonucleotide arrays and two-colour fluorescence analysis," *Nat. Genet.*, 1996, 14:441-447.
Hartl and Clark, "Organization of Genetic Variation," *Principles of Population Genetics*, 1997, Chapter 3, Sinauer Associates, Inc., Sunderland, MA, pp. 71-109.
Hayes et al., "Glutathione transferases," *Annu. Rev. Pharmacol. Toxicol.*, 2005, 45:51-88.
Hedrick, "An Introduction fo Gametic Disequilibrium," *Genetics of Populations*, 2000, 2nd edition, Jones and Bartlett (Sudbury, MA), pp. 396-406.
Hopenhayn-Rich et al., "Lung and kidney cancer mortality associated with arsenic in drinking water in Córdoba, Argentina," *Int. J. Epidemiol.*, 1998, 27:561-569.

(Continued)

*Primary Examiner*—Delia M. Ramirez
(74) *Attorney, Agent, or Firm*—Fish & Richardson P.C.

(57) ABSTRACT

Isolated GSTO2 nucleic acid molecules that include a nucleotide sequence variant and nucleotides flanking the sequence variant are described, as well as GSTO2 allozymes. Methods for determining if a subject contains a GSTO2 sequence variant also are described.

10 Claims, 35 Drawing Sheets

OTHER PUBLICATIONS

Ivanov and Hei, "Combined treatment with EGFR inhibitors and arsenite upregulated apoptosis in human EGFR-positive melanomas: a role of suppression of the P13K-AKT pathway," *Oncogene*, 2005, 24:616-626.

Ji et al., "Human phenylethanolamine *N*-methyltransferase pharmacogenomics: gene resequencing and functional genomics," *J. Neurochem.*, 2005, 95:1766-1776.

Landi, "Mammalian class theta GST and differential susceptibility to carcinogens: a review," *Mutat. Res.*, 2000, 463:247-283.

Long et al., "An E-M Algorithm and Testing Strategy for Multiple-Locus Haplotypes," *Am. J. Hum. Genet.*, 1995, 56:799-810.

Maeda et al., "Effective treatment of advanced solid tumors by the combination of arsenic trioxide and L-buthionine-sulfoximine," *Cell Death Differ.*, 2004, 11:737-746.

Maeda et al., "Tumor Growth Inhibition by Arsenic Trioxide ($As_2O_3$) in the Orthotopic Metastasis Model of Androgen-independent Prostate Cancer," *Cancer Res.*, 2001, 61:5432-5440.

Maiorino and Aposhian, "Dimercaptan Metal-Binding Agents Influence the Biotransformation of Arsenite in the Rabbit," *Toxicol. Appl. Pharmacol.*, 1985, 77:240-250.

Marnell et al., "Polymorphisms in the Human Monomethylarsonic Acid ($MMA^V$) Reductase/*hGSTOI* Gene and Changes in Urinary Arsenic Profiles," *Chem. Res. Toxicol.*, 2003, 16:1507-1513.

Martin et al., "Human methylenetetrahydrofolate reductase pharmacogenomics: gene resequencing and functional genomics," *Pharmacogenet. Genomics*, 2006, 16:265-277.

Mathews et al., "Single-agent arsenic trioxide in the treatment of newly diagnosed acute promyelocytic leukemia: durable remissions with minimal toxicity," *Blood*, 2006, 107(7):2627-2632.

Minamoto et al., "Arsenic-Contaminated Water and Extent of Acute Childhood Malnutrition (Wasting) in Rural Bangladesh," *Environ. Sci.*, 2005, 12:283-291.

Mulder and Ouwerkerk-Mahadevan, "Modulation of glutathione conjugation in vivo: how to decrease glutathione conjugation in vivo or in intact cellular systems in vitro," *Chemico-Biol. Interact.*, 1997, 105:17-34.

Nebert and Vasiliou, "Analysis of the glutathione *S*-transferase (GST) gene family," *Hum. Genom.*, 2004, 1:460-464.

Paul et al., "Skin cancers in chronic arsenic toxicity—a study of predictive value of some proliferative markers," *Indian J. Pathol. Microbiol.*, 2004, 47(2):206-209.

Pool-Zobel et al., "Modulation of xenobiotic metabolising enzymes by anticarcinogens-focus on glutathione S-transferases and their role as targets of dietary chemoprevention in colorectal carcinogenesis," *Mutat. Res.*, 2005, 591:74-92.

Prince et al., "Robust and Accurate Single Nucleotide Polymorphism Genotyping by Dynamic Allele-Specific Hybridization (DASH): Design Criteria and Assay Validation," *Genome Res.*, 2001, 11:152-162.

Ratnaike, "Acute and chronic arsenic toxicity," *Postgrad. Med. J.*, 2003, 79:391-396.

Salavaggione et al., "Thiopurine *S*-methyltransferase pharmacogenetics: variant allele functional and comparative genomics," *Pharmacogenet. Genomics*, 2005, 15:801-815.

Schafer and Hawkins, "DNA variation and the future of human genetics," *Nat. Biotechnol.*, 1998, 16:33-39.

Schaid et al., "Score Tests for Association between Traits and Haplotypes when Linkage Phase Is Ambiguous," *Am. J. Hum. Genet.*, 2002, 70:425-434.

Schmuck et al., "Characterization of the monomethylarsonate reductase and dehydroascorbate reductase activities of Omega class glutathione transferase variants: implications for arsenic metabolism and the age-at-onset of Alzheimer's and Parkinson's diseases," *Pharmacogenet. Genomics*, 2005, 15:493-501.

Shastry, "Gene disruption in mice: Models of development and disease," *Mol. Cell. Biochem.*, 1998, 181:163-179.

Soignet et al., "Complete remission after treatment of acute promyelocytic leukemia with arsenic trioxide," *N. Engl. J. Med.*, 1998, 339(19):1341-1348.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Strange et al., "Glutathione S-transferase: genetics and role in toxicology," *Toxicol. Lett.*, 2000, 112-113:357-363.

Strange et al., "Glutathione-*S*-transferase family of enzymes," *Mutat. Res.*, 2001, 482:21-26.

Tajima, "Statistical Method for Testing the Neutral Mutation Hypothesis by DNA Polymorphism," *Genet.*, 1989, 123:585-595.

Tchounwou et al., "Carcinogenic and Systemic Health Effects Associated with Arsenic Exposure—A Critical Review," *Toxicol. Pathol.*, 2003, 31:575-588.

Tchounwou et al., "Important Considerations in the Development of Public Health Advisories for Arsenic and Arsenic-Containing Compounds in Drinking Water," *Rev. Environ. Health*, 1999, 14(4):211-229.

Terwilliger and Ott, "Linkage Disequilibrium between Alleles at Marker Loci," *Handbook of Human Genetic Linkage*, 1994, The Johns Hopkins University Press, Baltimore, pp. 188-193.

Thomae et al., "Human catecholamine sulfotransferase (SULT1A3) pharmacogenetics: functional genetic polymorphism," *J. Neurochem.*, 2003, 87:809-819.

Thomae et al., "Human sulfotransferase SULT2A1 pharmacogenetics: genotype-to-phenotype studies," *Pharmacogenomics J.*, 2002, 2:48-56.

Underhill et al., "Detection of Numerous Y Chromosome Biallelic Polymorphisms by Denaturing High-Performance Liquid Chromatography," *Genome Res.*, 1997, 7:996-1005.

Vahter, "Genetic polymorphism in the biotransformation of inorganic arsenic and its role in toxicity," *Toxicol. Lett.*, 2000, 112-113:209-217.

Wang et al., "Human thiopurine *S*-methyltransferase pharmacogenetics: Variant allozyme misfolding and aggresome formation," *Proc. Nat. Acad. Sci.* USA, 2005, 102(26):9394-9399.

Wang et al., "Thiopurine S-methyltransferase pharmacogenetics: chaperone protein association and allozyme degradation," *Pharmacogenet.*, 2003, 13:555-564.

Weinshilboum and Wang, "Pharmacogenetics: Inherited variation in amino acid sequence and altered protein quantity," *Clin. Pharmacol. Ther.*, 2004, 75:253-258.

Whitbread et al., "Characterization of the human Omega class glutathione transferase genes and associated polymorphisms," *Pharmacogenet.*, 2003, 13:131-144.

Whitbread et al., "Glutathione transferase Omega class polymorphisms in Parkinson disease," *Neurology*, 2004, 62(10):1910-1911.

Wood et al., "Human Arsenic Methyltransferase (AS3MT) Pharmacogenetics. Gene Resequencing and Functional Genomics Studies," *J. Biol. Chem.*, 2006, 281(11):7364-7373.

Yang et al., "Role of the Glutathione Metabolic Pathway in Lung Cancer Treatment and Prognosis: A Review," *J. Clin. Oncol.*, 2006, 24(11):1761-1769.

Yu et al., "Genetic Variation in Genes Associated with Arsenic Metabolism: Glutathione *S*-Transferase Omega 1-1 and Purine Nucleoside Phosphorylase Polymorphisms in European and Indigenous Americans," *Environ. Health Perspect.*, 2003, 111:1421-1427.

Zakharyan and Aposhian, "Enzymatic Reduction of Arsenic Compounds in Mammalian Systems: The Rate-Limiting Enzyme of Rabbit Liver Arsenic Biotransformation Is $MMA^V$ Reductase," *Chem. Res. Toxicol.*, 1999, 12:1278-1283.

Zakharyan et al., "Enzymatic Methylation of Arsenic Compounds: Assay, Partial Purification, and Properties of Arsenite Methyltransferase and Monomethylarsonic Acid Methyltransferase of Rabbit Liver," *Chem. Res. Toxicol.*, 1995, 8:1029-1038.

Zakharyan et al., "Human Monomethylarsonic Acid ($MMA^V$) Reductase Is a Member of the Glutathione-S-transferase Superfamily," *Chem. Res. Toxicol.*, 2001, 14:1051-1057.

\* cited by examiner

Figure 1 – page 1

| | | | | | | |
|---|---|---|---|---|---|---|
| 1 | CAGGCATTGA | ACCTGGGGTG | GACGCCTTCG | TCCTCTTACT | TTCGGGAACA | CCCTACTCTG | 60 |
| 61 | TCTATGGAGT | AGCTGTTTTT | TCACCACTTT | ACTTTCTTAA | TAAACTTGCT | TTTGTTTTGC | 120 |
| 121 | ACGGTGGACT | CGCTCTGAAT | TCTTTCTTAT | GCGAGATCCA | AGAACCCTCT | CTTGGGTCTG | 180 |
| 181 | GATCAGGACC | CCTTTCCCGT | AACATCTATG | CAGGAGGAAT | AACATGTGTT | CCATCTTATT | 240 |
| 241 | TTACAGGTGA | GGAAACTGAA | ACACACTGAG | GTTAGTGACT | TCCCCATGTT | CACAGTTAAT | 300 |
| 301 | AAGTGGTTGT | TACGGGTTGA | ATTGTGCTCC | CCCAATTTCA | TACATTGATG | TTCTAATCCC | 360 |
| 361 | CAGTGCCCCA | GTATGTGACC | TTATTTGGAA | ATAGGGTTGT | TGCAGATGTA | ACTAAATTAA | 420 |
| 421 | AATGAGGTCA | TACTGGAGTG | TGAATGAAGA | TGAAGGCACA | GATGGGGTGG | GTGGTGCTTC | 480 |
| 481 | TGCACTCCAA | GGGACACCAA | AGATTCCCTC | AAACCACTAG | AAGCTGGGAG | AGAGGCATGG | 540 |
| 541 | AACAGACTCC | CTCACAGACT | CCCTCCTCAG | AAGGCAGCAA | CCCTGCTGAC | ACCTTCATCT | 600 |
| 601 | TGGACTTGTA | GCCTCTAGAA | CTGTGAGGCA | ACACACTTCT | GTTATTTAAG | CCACTCTGCA | 660 |
| 661 | GTACTTTGTT | ACCCTAGTCC | TAGCAACTGA | ATACAGGGGT | GGAGCCAGGA | TCAAAACAGG | 720 |
| 721 | CAGGGTGCTC | AACACTTGG | TGCTTTTCAC | CTCATTCTCT | GCTCCTCCCA | TAATAGGGCT | 780 |
| 781 | AATCAAAATA | AAAATAGACA | TCTACCCCAA | TCTCACCCCA | ATAAATGGCA | CAGGAGTTAC | 840 |
| 841 | CAGCTTTCAA | ATCTAGGCAA | ACAAGGAAAT | CATTGAATAG | TCTTTTTCCT | CATCTGTATG | 900 |
| 901 | ATGGCCCTGG | AACCCCTCTT | TCCTGACCCC | TAAGTTAAAA | GAGCTGTTTG | AGAGGACTCT | 960 |
| 961 | CTGGCCAGAC | CTTTATTCCC | AGACCCAAAA | CTAAATTCAC | TCATGCCACC | TGCTTGATTC | 1020 |
| 1021 | TGAGCCTGTG | CCCTTATTGT | AACTGAAATG | CAGGTTCAGT | TGCTTCCCGC | TTTCAGAGTC | 1080 |
| 1081 | CAATTATTAA | TAAGAAGAGC | AAAGTCTGGT | ATAAAGAAAG | TGATTTTTTA | TTCCAAAGCT | 1140 |
| 1141 | AGCTTAGGGG | GAGCAAAACA | GGCTTCCTGC | CTTAAGGGTA | CCACTTGCT | TCTGGGCAG | 1200 |
| 1201 | AAAGCAGGGG | CTTTTAAAGG | GGGCAGTTGG | TATGAACTGC | ATGCTGGGA | GGGAGCGAGT | 1260 |
| 1261 | GGGTGGGGGT | TCGCATGACT | CACTTTGGTG | CTTTATCTGC | TGGGTTGTGC | CATCATGGGC | 1320 |
| 1321 | AGAAGTCATT | TGTAAAGTGG | CCTTGTCTCA | GGCATACTTT | TGGATGTAAA | TGGACTGTTA | 1380 |
| 1381 | TCTCTGGAGG | CAGTCTCCTG | GGGGGTGAGA | GTCCTGCTCT | GGAGCTTTTA | AGTAAACACC | 1440 |
| 1441 | CAGTTAGATA | AGCTTGCCCT | GTAGGGAGTG | TCAGGTGAAG | GGAAGGTAAA | AGATGATAAT | 1500 |
| 1501 | TGCATTTCTA | AAGAGCTAAG | TAGGAAGTGG | GGAACAGGGA | GAAAGGAGGA | AACAGAGAAG | 1560 |
| 1561 | ATGGGAGAAA | TAAATAATGT | AAAAAATAAC | TCATCCTCTA | TCTCTTAGAA | AAATGGGAGT | 1620 |

Figure 1 – page 2

```
1621  ACTGTTATAT TACCAGGGCT CCAAAACACA AATGTTTAAT AAGTGGGAGA GTTTTGAAAG  1680
1681  CAGCACCATT ATTCTGAGGT TGATAATATC CAGGTTTGTG CTGTCTCCTA TGGGTTAAAA  1740
1741  TGAAAAGGAT GTATCCTACA GGTGACGGTA GGGACAGAGG CCCTCCCAGT AGTCACGTTA  1800
1801  AGCTAGTACT GACAGAAAAA GGAAAAGCCT GTCCAGGTGG CTGGGCAACC CTGCAGCGAG  1860
1861  GCATAGATGA GCTTGTAAAT CAAAGGAAAT GACCAAGGTG AGTCTCAATC CTTTTAGAGG  1920
1921  TTTATTTTGC CAAGGTTGAG GACACATCTG AGAAAAAGGA ACACAAAATC ACAGGAACAT  1980
1981  CTGTGATCTG TGCTCTTTCC AAAGAGGGCT TGAGGACTTC AATATTTAAA GGGAAAGAGC  2040
2041  AGGCAGTAGG GGAAAGTGGA AAGTAAAAAG GAAGGTAGA TAAAAGGGGA GAGTAGTTGC  2100
2101  ATTCTTTGGG GCCTTTGATC AGCATTCACT GAATGCGCAT GTTACATTCG TGAAAGGAGG  2160
2161  TCGTAGAGGA ATAGTCAGTT ATGCATTCGT CTAGTGCTTG GTGAATCTGC ATTTTTACAA  2220
2221  GATTAAATAT AGGGTAGAGG AAGCGGTCAA ATTGCATTTT TCTCCAGCGA GAGGAAGGAT  2280
2281  GACTCCTAGA CCTGTCTTTG TCCCATACTT GGGAAGATAA GCTGTTAGTT TACATTGCCA  2340
2341  AGATGAAATT CAACTGATCT GTTTTAGAGT AAAGATCTTG CGGGCCAACA AGGAATTTCC  2400
2401  TTGGGGAGGT GTGTGGCCTT TGATCTTTGT AGCTATTTAG CAACAAAATG GGAGGCAGTG  2460
2461  TTGCCTGACT CAGTTTCCAA GCTTGACTCT TCCCTTTGGC ATAGTGAGTT TGGAGTCAAG  2520
2521  AGATTTTTAT TTTCCCTTCA CAAGCTGAAC AGGAGCCTTT GGAGAGAACG CTCTGGACCG  2580
2581  GTGAGTGAGC CATGAGGTCG GGCCACAGGC TCTGAAGTCG TGAAGCCTTG GGACGGAGCG  2640
2641  GGTGGTGCTT CGAGGTCAGT GTCACGGGAG GGAGGTCAGG GTCAGGGTCA GACGTGGAGC  2700
2701  CCCGTGGAGT GCGGAGTGGT GACCCCTTCG TTCGGGGGCG GAGGGATGAC TGAGCATTTA  2760
2761  TAACTTTTGT GTATCTCCCC GTGGGTGCAG CCCTTGGCCA GCGAGATGCT TTGACACAGC  2820
2821  CCCTTAAGAT GTTTTAAGGG CTATCCCATA AAGCCGGGAA GGCACAACGG GTGGAGCTGG  2880
2881  CGGCCGCCGG GGGCAGGCAC TTTTGAGCTA AGGAGGAAGC GGGGGAGGGA AGGAGGGCGG  2940
2941  GAAGGACGCG CCACCTACTT CCTGAATCCC CTGCAAACCC CAGAGGAGCT CGGCCTGCGC  3000
      GST-Omega 1 Exon 1
3001  TGCGCCACGA TGTCCGGGGA GTCAGCCAGG AGCTTGGGGA AGGGTGAGGC CTGCCCGCCG  3060
3061  CGAAGAGGGG GTGATCTCGG CGACCCCCGG CGGCATGTTC GAGGCTGCTC CGGGAGCCCA  3120
3121  GCCGCCCGGG AGCGCCCCAC CGGCGGGGAA CGGGTCGGAG CTGCAGTGGG ACGCGGGGGC  3180
```

Figure 1 – page 3

```
3181  GGTGGGATAC GGGGGGTCTC GACACCTCTC TGGGCCGTAA TCGCCTTCGC TTCTCCCCGG  3240
          GSTO1 Exon 2
3241  CAGGAAGCGC GCCCCGGGG CCGGTCCCGG AGGGCTCGAT CCGCATCTAC AGCATGAGGT  3300
3301  TCTGCCCGTT TGCTGAGAGG ACGCGTCTAG TCCTGAAGGC CAAGGGAATC AGGTGGGCAC  3360
3361  CCAGGCGGGG GACGCTCCCC GAGCCGTCCG GGAGCCTGCT GCAGGCGGCG GGTGGGGTG   3420
3421  GGGTCTCAGC CCCCTTCTAC CCCCCTCCCA CCAGCGTCCT TTACTGCACA TTAAACTATT  3480
3481  CTCGGCCCTT TGGAAAATAG CAAGTTATAG GCCATTCCCC TAGGAAAAAT AGGCCACAGA  3540
3541  TTCCAACGGT CTAGGACACC TCATTTAGAT TAACCAACCA TTTAATGGAT TAGAAAAGCT  3600
3601  GAGGCTCCAG TGATGTTAGT GATTTGCCCG GTAATAACCG GCAGCAGCTC TTTTAGCTTT  3660
3661  GGTAGGTCAC GAATTCCTGG TCCAGAGTCC TTTCGCTTTC GCCCTATTGT GATTTCCCGT  3720
3721  TCTTATTCCA GCTTAACTGT TAGTTGTTAT TCTGAATGTA TTGTTCCCTC CTAGAATAGT  3780
3781  AATTTACCCC AGTACAGCAG AGTTTAGACC CTGACCCTCC TAGGGTAGTG CTGAGTTTAC  3840
3841  TGCACATATT CCTGTGGATT GGGCTGTTGG TTGAGTCAAA TAGAGGGAAG TGTCTGTCTA  3900
3901  GCTCATCCTT CTGCAGAGCC TGTTTTGAAA CTAGCATAGT TTTTGACTTA CGGGCTATCC  3960
3961  ACAGGATATG TGCAACAGTC ACTTGACTTT TCTCTGACAC CAAGTATCCA TTGGAACCAC  4020
4021  TTCCCTTCCC ATGACCTTTG GATGTCTGTT GATTAGACAT TTATTAGATA CCTTTGGTGT  4080
4081  GGAAGGTTCT GTGGAAGTTT AAAACAAACC CCCTATTCTT AAGGAATTTT CTGTCTGTGT  4140
4141  GCTTAGTGTT TGTGAACTAA TTTTAGTCTT CTAAGGGGAT AATCTTTAGG GGTAGGCAAT  4200
4201  TATTTTCCCT AAAAGAAAGG TAAAATGCAT TTAAAAAATA CATTTGAAGG GGATTTGTCA  4260
4261  TTACTTCACT AAGAAATGCA TCTCATTTGG ATGAGATTAT GATTCTGAAC ACATAGAGTA  4320
4321  CTTACTATTT CATAATGTTT CTCAAAAACA CTGTCATATT TGCTGTGATA GAACTCTTTT  4380
4381  ATTGTACTAA GAGAAATCTA ATGTAACCAA AATTGAAAAA AGACATTTTT TGGTACTCAT  4440
4441  TTATTTGAAA AGTCCAGGAG CATGACACAG CTGGATTCAG AGGCACAAAG TCCTGGGTTA  4500
4501  TGTGCTTCAC CCTGGACCTT TAGTTTGAAA ACAACCCTAC CTTATTTACT GGGGCAGTTT  4560
4561  TCCAAAGGAA CATTGAAACT ATCTTCCCCT AATAGTGTGG GGTAGAGGGG AGGAAGAGAG  4620
4621  TGGTTAACAG CTTCCAGACA GTGCAAACAA CAAAGGTCTA CTACATTAAT AGACCAGTTT  4680
4681  TAAGCTTGAG CCCGAGGAGG CTTTTACTGG GAAAGTACTA GATTTTAACC ACATGATATG  4740
```

Figure 1 – page 4

```
4741  ACTTAACAAA GCATGGTTTT CTCTAAAAGA TGCATCTTCC AACTTGCTGT GGCAGGTGTG  4800
4801  TAGACTTGTT GGCTCACAAT GCCAGCTTAC CAAAATTCAT GTGTGTTCTG ACATACTTTT  4860
4861  TTTTTTTTAA ATAACAAAAG CCCAGGATCT TTTTGTTTTC ATAGTAACAA AAGTTTTTGT  4920
4921  TTTATAGTTC AAAAATGTTG ATAATTCTTT GGCAAGGAGC CAAATAATTT TTTTTTTTTT  4980
4981  TGCAATGGCT GGTACTTAAG TGTCCAGTAT TGTCAGCACA TGAACCTTTT AAATTACATG  5040
5041  CACACCTGTG CTCATGTTCA AATTGGATGT TCCTTTGTTT ACATGGGGGA TTATGTATTT  5100
5101  AAATCCTCAA ATGAAATGCT GTTCTAGCTA CAGCTGTGGA TGGGAAAATA GAAAACAAAA  5160
5161  GGTATTGGTG TCTATTTTTT TTTTAGTAAT CTGTTCTATT GAACATTTAT TCAGCCTTGA  5220
5221  CAATCATATG GACCTAGCTC CTTTCTCTTA GTTCCTCTAC AGTCTCAGGC AACATACAAG  5280
5281  ATAGACCTAA ATACAATCTG ACTATAGCCT GGACTTCACC TGTTTCTTC CTTTTTGGTT  5340
5341  TACTTTGTAT GATTTACTCA GACAACATTT TTAAAAAAT CAGTACATGG AGATTTAATC  5400
5401  TGAAAGCTTA TTTTGTGGGT GGATTTTTTT TTTTTTTTCG AGACAGGGTC TCGCCCTGTC  5460
5461  ACCCAGGCTG GAATGCAGTG GTGCAATCAT GGCTCACTGC AACCTCTGCC TCCAGGGCTC  5520
5521  AAGCAATCTT CTCACCTCAG CATCCGGAGT AGCCGAGACT ACAGGTGAGT ACCACCACAC  5580
5581  TTGGCTAATT TTTATATTTT TTGTAGAGAT AGGGTTTCAT CATGTTGCCC AGGCTGGTCT  5640
5641  TGAACTCCTG GGTTTAAGCA ATCCGCCCAC TGCAGTCTCC CAAGGTTCTG GGATTACAGA  5700
5701  TGTAAGCTAC CAAGCCTGGC CTTGTGGGTG GATTTTAAGG ATTCCTTAAT ATCTTCATAA  5760
5761  AAACCAAGAA ACTTTTTACT CAAATTAGCA AAATAAATTG AATTTTATGT TGGTTCTCAT  5820
5821  ATAGTGGATA GTGGACACAA TTCAATTAGT TGCCTCATAT GATTTATAAC TAAGATACCT  5880
5881  CTTAGCCATA AATGGAGTAT CTTATTGACA ATTTGAAGC ATTTCCACAG ATTTATTCAT  5940
5941  TCATTTATAT GAAATATTTC AAAACAAAA TATTTACTGA GTCCTTATTT GAAACTTTTT  6000
6001  ATTTTCTTCA GAGCATTTAT ATCTATATAG CATTTTGCTC ATTTACATGT TTGTTTATTA  6060
6061  CTATGAACAG ATACACAAGA TCCCACCTTT CGTGAAGCTT ACATTCTAGG AAGATAACAA  6120
6121  ACTTGTAAAT AAGTGAGCAA AGTAATTTCA GATACATATT ATCAGTTCAA TGAAGAAAGT  6180
6181  AAAACATGAT AATCATGTAA TAGAAGCTGC TCAGCAACTT CAGAGCTATG GTCAGGGAGG  6240
6241  GCCTGGGGAT GTGTGTTTGA CCTGGGAAGA CCTGGGAAAA GGCAGGCAGA GGAGGCAGAG  6300
6301  GACCATCAAG TGCAAAGACT CTAAGGTGGA AACACATTTG GCAAATTCAA GGAATATAAA  6360
```

Figure 1 – page 5

```
6361  AACCGCCAAC GTGTAAAAGA AAACATAGGG GAAAAGCTTC ATGACACTGG CCTTGGCAAT  6420
6421  GATTTCCTGG ACATGACACC AAAGACCAGG CAACAAGACC AAAAATAAAC ACATGAGACT  6480
6481  ACAGCAAACA AGCTTCCACA CAGCAAAGGA AACGATTAAC AGAGCAAAAA GGCAACCTAT  6540
6541  GGAATAGGAG AAAGTACTTG CAAACCACAT ACCTGGTAAG GGGTTAATCT CCAAAATACA  6600
6601  TAAGGAATCT CTACAACTCA ACAACAAAAA AACCTGATTT TAACATGGGC TAAGATCTTA  6660
6661  CATAGACACT TCTCAGGCTG GGCATGGTAG CTCACGCCTA TAACCCCGAG GCAGACAGTT  6720
6721  CACTTGAGCC CAGGAGTTCA AGACCAGCCT TGGCAACATG GCAGAATCCT GTCTCTACAA  6780
6781  AGAAATTAGC TGGGTGTGAT GGTGCACGCC TGTGGTCCCA ACTACTCGGG AGGTAGGAGG  6840
6841  ATCGCTTTAG CCCAGGAGGT CGAGGCTGCA GTGAGCTGCG ATCAAGCCAC TGTACTCCAG  6900
6901  TCTGGGAGAC AGAGTGTCAA AAAAAATTAA AAATTAAAAA AATAGACATT TCTTCAAAGA  6960
6961  GGATATAAAA ATGGGCAACA CATATATGAA AAAGTTCTTA TCACTAATCA TCAGGAAAAT  7020
7021  GCAAATCAAA ATCACATAAT AACCTCACAC TTGTCAAGAT GACTATAATG AAAAAAGACA  7080
7081  AGTGTTAGCA AGGATGTGTA GAAATCAGAA CCTTTGCACA CTGTTGGCGG GAATGTAAAA  7140
7141  TGGTACAGCT GCTATGGAAA ACAGTATAGA TGTTCTTCAA AAAATTAAAA CTAGAACTAC  7200
7201  CATGTGATTC AGCAATCTCA CTACTGGGTA TATATCCAAA TTAAATGAAA TCAAGTTCTC  7260
7261  AAAGAGATAT TAGCACTCTC ACGTAGACTG CAGCACTGTT CACAACAGCA TAATGTCAAT  7320
7321  GTCCATCAGC AGATGAATGG ATAAAGAAAA TGTGTTAATG CTATTCCACC TAAAAAGGAA  7380
7381  GGAAATTCTG CAATATGTGA CAACATGGAT GGACATTGCG GACATTATGC TAAGTAAAAT  7440
7441  AAGCCAGACA CAGAAAGACA AATACTGCAT GATTGTTCTT AAAAGGTGTA TCAAAAGTAG  7500
7501  TCAGATTCAT AAAATCAAAA ACTAGAATGG AAGGAATCTA GGCAGACTCC TAAATTTGGG  7560
7561  GTCTGATCAG CTAAGTGGAT GGCAAAGCCA GTGAGAATTT ATCCAAAAGC ACAAAAGTTG  7620
                                                      GSTO1 Exon 3
7621  TTTCCTTCTC TTCATAGTCT CCTATGTGTC TTTCAGGCAT GAAGTCATCA ATATCAACCT  7680
7681  GAAAAATAAG CCTGAGTGGT TCTTTAAGAA AAATCCCTTT GGTCTGGTGC CAGTTCTGGA  7740
7741  AAACAGTCAG GGTCAGCTGA TCTACGAGTC TGCCATCACC TGTGAGTACC TGGATGAAGC  7800
7801  ATACCCAGGG AAGAAGCTGT TGCCGGATGA CCCCTATGAG AAAGCTTGCC AGAAGATGAT  7860
7861  CTTAGAGTTG TTTTCTAAGG TTTGTGCATA AGAAATTTCA GCTCCTATTT GAAAAACCTG  7920
```

Figure 1 – page 6

| | | | | | | |
|---|---|---|---|---|---|---|
| 7921 | TTTTTTAAAG | CGAAATCAGT | GCTGCCATTT | ATGGTTCAGT | GATTTGGGAG | AGAAAAACAA | 7980 |
| 7981 | AACAGGAATA | TGCTTGTCAG | CTCTGAGTGT | CCTGCAAGTC | CTTTCACGAT | CCAGTTCCTG | 8040 |
| 8041 | TTTACCTCCA | AAATTATCCC | TTTTCACTCG | TCTCCTGACA | CTTTATATAT | GCCAGCCATA | 8100 |
| 8101 | CTAAACTTTT | CTCAGAATTC | CCAAATTCGC | CCCTTTCTCT | TTCAATTCTT | GCTGTCAGAT | 8160 |
| 8161 | TCTTCCCACT | TCTCACTGTG | CCTGGTTATC | TCCACGTCAT | TTTTCACATG | TCTGCTCCGA | 8220 |
| 8221 | CACTGCTGCC | TTTTCAGGAG | CTTGGCAGGC | TGGTTAGTGC | TCTAGCTTCT | GAGTTCCCAT | 8280 |
| 8281 | CCGTGTGAAC | TTTTGCCTGC | CTTCTTGCCT | GTGTACTGCA | CTGGGGCTGT | GAGCTCCTTG | 8340 |
| 8341 | AGGGTGAGGG | CTGTGTTTTG | ATCACTGTTA | GTTCACTGCC | TAGTTTATG | ACTGGCTCTG | 8400 |
| 8401 | CTACTTTCTT | GTGACTCTGA | GCAAGTTACT | TATTACTTTG | CCTCTCCGTT | CATCATTGGT | 8460 |
| 8461 | AAAATGGATA | TAGTAATTGT | TCCCACCTCA | TAAGATAAAA | ATCAGTTAAT | ATAAAACACC | 8520 |
| 8521 | CAGAACAGAG | TCTGACACAT | GGGAACTACT | TAATTCTTGT | CCTTATAGCC | ATAGCATCAA | 8580 |
| 8581 | GCAGTGAGCA | TCTACTTTGT | GTTGGCAATA | ACTCAGATGA | CTGAATAAAT | AGCAATCCTG | 8640 |
| 8641 | TAGAAGAACT | GTTTGTACCT | TACTTAGCAT | CAACACTGTG | GATTAGTTCA | AACAATTAGT | 8700 |
| 8701 | ATTAACAAAG | AAATGACTAA | AAGATGTGTG | TTTAGACACC | AAGAATAGCA | TGTCTGGTTA | 8760 |
| 8761 | TATGCCTATA | ACATTGTCAC | CTTGGTAGTA | CGGTCAGTAT | ATAAAGGATT | ATCTTTAGAG | 8820 |
| 8821 | AAAAGATGG | TTAAAGAAAT | GCCCTAAGAG | AGAGTTATAG | GGAAAACATT | CTGTTTTAGG | 8880 |
| 8881 | AGACATTATA | AAGGGAAGCC | AATGGGACAG | GAAGAGTGAG | TCATCTGCTT | AGTAAGATGA | 8940 |
| 8941 | GGGTGAAAGA | ATAGTAGAGG | CGGCTGCTGT | GAAAGATAAT | GTAAAGGGAA | CATGACATTT | 9000 |
| 9001 | TCAAGAACGA | TGTGGGAGAG | TTTTACAAAG | TAGTAACAAG | TTAAAGGCAT | GCAGCTTCAA | 9060 |
| 9061 | GACACGAAGT | CATCAATACC | AACCAAAAAA | AATAAGCCTA | AGTGGTTCTT | AAAGAAAAAT | 9120 |
| 9121 | CTCTTTGGTC | TGGTGCCAGT | TCTGGAAAAC | TTTTTTTAGT | ATGGCTGGAA | TATAAAGTGT | 9180 |
| 9181 | CAGGAGAAGA | GATAAAAGGG | GTAACTTTGG | AGAGGTAAAC | AGGAACTGGA | TCGTGAAAGG | 9240 |
| 9241 | ACTTGTAGGA | CACGTCAGAG | AAAATGAGCT | TTAAAAGTAA | AGCTTTTAGA | CATGAAGCTT | 9300 |
| 9301 | TACTTTCATG | CATAAAGCTA | CTACTTTAAA | AAGTAGTCAC | AAGAGATTCA | TTGTACTATC | 9360 |
| 9361 | TAGAAAGAAA | ATGAGATTTA | AAAGTAATGC | TGAAGATGCC | CACCTTTACT | TCCCTGCTTG | 9420 |
| 9421 | GGTTTTAAAG | GAGAGGTGGC | TTTATGTACA | TATGACCCTG | CTCTCCTGGC | CACAGCCCAT | 9480 |
| 9481 | CAGAACAGAA | ATGTACCCCA | CCCCACACAC | CTGGGCCAGT | TATCTTCTCT | CCTGGGAACT | 9540 |

Figure 1 – page 7

```
 9541  TGGAAATGAG ACACAGAACT AAGACAGTAA AGGTTAGGAC AGTAAAGACA ACTAAGCGTT   9600
 9601  GGGGCTCAAA TAATGTTAAT TAGAGGCTAG AAAAACCAAA GCCACTTAAG AAATAAATTT   9660
 9661  TTAGAGGAGC AAGAATTAAA AACATTGCAA AGGGACTGAA GTATGCAAAG TAATATGGAG   9720
 9721  CAGAAATGTG AGGAAAAACA GACGAAAGAC CAGGCAGACC CAGGTGGAAA TGTGGATGAA   9780
 9781  AGGGCTGCCT GAAAGCCTTC AGTCCCAGTG AAGGCAGGCT GAACTGATGT GGATGGGATT   9840
 9841  TCATGGGATT CTATATTTTT ACAAGTGCCT GTTTACTTAA ACTAGGATGA GTGGACTTCT   9900
 9901  GCGTCTTGCA ATAAAATGAT ACCAAAGACC AAGTATTAA AACACATAAA CACCATCACG    9960
 9961  AGCATTAAAG CATCTGATGC TACACCCATC AAGTCTTTAG GTAGTCGGTC CCTTTTGAAC  10020
10021  AGTCTCCTGG TGTCCTCCCC AACAAAGAAA TCAGAAAAAT TTTCTTCCCT AGCTCTTTGC  10080
10081  AGTTGGGGCC AAGTTTTGTG ACCTAGGCTC TTCCTGTCAG ACACACACAT AGAGTTCAAA  10140
10141  TCAGAAACGA GCAAGGTAAG GAAACAGGCT TGGTGGGATA TCTGCTTAAG ATATTCAGCT  10200
10201  CTCCACTGGT TTTCCTGGTG AGAGCAGCGG CAGAGCTTCT GGGTTTCAGC AGTGTGGGTT  10260
10261  ACAAGATAAA ATTCCAGAGT AGAAATGGCA TCAGTGCCAG TGGTGTTAGC AGTTATCTCA  10320
10321  GACTCTACTT TCTGGCAGCC TCACAAACTG AAGCATCTGG TGCTCAGCTT GGACTGGCAG  10380
10381  CAGTGAGTGC TTCCCATTAG GCCATTTCTC AGCATGAATT TGGGATGTTC TGTCTTAATT  10440
10441  CCAAGCCTGT TTGTTCCGCC TCCCAATAAT TCTATGAGCC ACTCAGTCTC CTTTAAAGAA  10500
10501  AGTTGTGTTG GCCGGGCGTG GTGGCTCAAG CCTGTAATCC CAGCACTTTG GGAGGCTGAG  10560
10561  GCAGATGGAT CACCTGAGGT CAGGAGTTTT CAGACCAGCC TGGCCAATAT GGTGAATCCC  10620
10621  CATCTCTACT AAAAATACAA AAATTAGCCT GGCGTGGTGG CGCACGCCCA TAATCTCAGC  10680
10681  TACTAAGGAG GCGGAGACAG GAGAATTGCT TGAGCCCGGG CAGTGGAGGT TGCAGTGAGC  10740
10741  TGAGATCGTG CCACTGCATT CCAGCCTGGG TGATAGAGCA TGACTCCATT TCAAAAAGA   10800
10801  AAGAAAGTTG TTTCTTAAAC GTGCCAGGGT AGCTTCTGTT ATTTGTAATT TATAAAATCC  10860
10861  TGACCAAGCC AGCATTTTAG GCCACAAAAC TGTTCCTAAG ACCAGTCCAT TACCTCTGTG  10920
10921  AGCGCAGGAA CTTGATGCAC CCTTGGTGTT TCTAGAACAC CTTGACACCA GGACTGTAAG  10980
10981  GGTTCTACCA TATTTTTATG TGAGGGGCC GATACAGTTA GCCATAAACT GATAAACTAA   11040
                                GSTO1 Exon 4
11041  GAAATTATTC TCTGTCTAGG TGCCATCCTT GGTAGGAAGC TTTATTAGAA GCCAAAATAA  11100
```

Figure 1 – page 8

| | | | | | | |
|---|---|---|---|---|---|---|
| 11101 | AGAAGACTAT | GCTGGCCTAA | AAGAAGAATT | TCGTAAAGAA | TTTACCAAGC | TAGAGGAGGT | 11160 |
| 11161 | AATTATTTCT | CCTAGCTATC | ATCAGAGTAA | ACGATAACTA | TATCTACCCT | CCTTTTCCTC | 11220 |
| 11221 | CTATTCTTTT | CTTTATATTC | CCACTTTCCA | AGTCACTTTA | AGGTAATTAG | GAAAATTCCC | 11280 |
| 11281 | CTAAACATTT | TTGTTTACAG | CAGACTGCTG | TTATAAAGCA | GAAAGCTGTC | CTGCTTAAGA | 11340 |
| 11341 | TATAAATCAA | AACACCTAAA | CAGACTTTGT | CATGGGCTTG | CTTTTAAAAT | ATTCTGCTAA | 11400 |
| 11401 | TGTTAAAATA | ACAAGGAAAA | AGGAAATTGT | ACCCACGTTT | CCACAAGTTT | TTATGTATCC | 11460 |
| 11461 | AGTTTTCCAT | GCTTGTTTGC | AGTCCTTGTC | CATATATTTA | AAAAAAATTA | ATATAGCTCT | 11520 |
| 11521 | AATCAGAGCA | TAGATATCAT | TCTGTGTCCT | GCTTTTTTTC | CTGTGTCCAC | TTAGTATTAC | 11580 |
| 11581 | ATACTAAATA | TTTCCCACCA | GAAAAGTTT | GCAATGAACA | GTACAGACAC | TTGAGGGAAG | 11640 |
| 11641 | CCCAGATGTA | TTTTACCTTC | TTTTGGGGAC | AGCTGACATT | TGGGCCTTGG | AGTCTGTCTC | 11700 |
| 11701 | TTGGCCTTGA | AATATTTCAT | TCATGCTAAG | CCTGAAGTTT | TTACTGACAG | AAGACATAGT | 11760 |
| 11761 | TCCTGTCTTT | CATGGGAATG | CATTTTAACA | TTTTATCAGT | AAGCATGATG | TTTGCTGTAG | 11820 |
| 11821 | GTTTTTCAGA | AACCTTTTTT | TCATTATAAA | GTTCTCTTCT | ATTACTAGTT | TGCTAATTTT | 11880 |
| 11881 | TAAAAAGTC | ATAAATGTTG | AATTTATTG | AATGGTTTTT | CTGCATCTGT | TACATCTATT | 11940 |
| 11941 | GAAATGTTCA | TAGAATTTTT | TCCTCTTAAT | CTGGTGAATA | TGGTGCTATT | GACAAATTTT | 12000 |
| 12001 | TTTTTTTTA | ATGTTTAACC | ATCCTAGCAT | TCCTAAGATA | AAACCTACTT | GTTCTCTATG | 12060 |
| 12061 | GATTTTTATA | TGTACTGTAG | AATTAGCTAA | TGAATGATTT | TTGTATGTGT | GTTCATAAAT | 12120 |
| 12121 | GAGATTGGCC | TATAAATTTT | CTACTCTTAT | AGTATCATTA | TTGGCTTTTG | GTTTCAAGGA | 12180 |
| 12181 | TATTCTGACC | TCATAAAATG | AGTTGGGTAA | CTAACCTGTT | TTTCTAATCT | CTGAAACCAT | 12240 |
| 12241 | TTGGTAGGGA | CTAGCGGTTT | CTTTAAAACA | TTTGAGCCTG | GTGTCTTTAA | CAGGGGTAGA | 12300 |
| 12301 | TTTTTCATTA | CTAGTTTGAT | TTCTTTAATG | GTAATTGGTT | TTTTGGTTTT | ATATTTCTTC | 12360 |
| 12361 | TTGAATCAGT | GTTGGTACTT | TTATATTTTT | CTGCTGAACA | GTGTGGGAGC | TGGAAAGTAA | 12420 |
| 12421 | GATGCAGTCC | ATATTCTTCA | GATAATTAGT | TTAGTAGTAG | ACAGAACACA | GTAGGTAGAT | 12480 |
| 12481 | ATAAGCAATC | TAAAATGCAT | ATTATGCATT | GAAAAAAAAC | TATGGAGGTT | ATTTATAAAG | 12540 |
| 12541 | GGCAAATTAG | TTTGGTGGTT | TAAATAGCCA | GATAATATTC | TCAATCACCC | CCTTTGGCAA | 12600 |
| 12601 | ACCCTGTAAC | CAATTCGCCT | TCTTAAAATT | TCAGAAACAT | ACAATTTGTG | TTTTGTTTTC | 12660 |
| 12661 | AAATGATTGT | CATCTGTTTA | GCAGTTAATC | CAGTCTATTT | CCAGTATATT | TTAAGTACAA | 12720 |

Figure 1 – page 9

```
12721  ATGCTTTTGC ACTTACAATG GGGTTACATC CAATAAACCC ACCGTAAGCT GAAAATATCA  12780
12781  TAAGTGGAAA ATGCATTTAA TAAACCCAAC CTACAGAGCA TCATAGCTTA GCCTAGCCTG  12840
12841  CTTTAAATGT GCTCAGAAAA CTTCCATTAG CCTGCAATTA GGCAAAATCA TCAAACATAA  12900
12901  AACCATCAAA CATAAAATAT TTATAAAGTG TTGAATATCT CATATAATTT ATCGAATACC  12960
12961  TGCATCCAAA AGATGCTGGC AACACAGCAC ACTTTAGAGC ATTGGTTGTT TACTCTCTTG  13020
13021  ATGGTATGGC TGCCCAGCAT CAAGAGTTAT CATACTGCAA ATCGATAGCC CAGGAAAAGA  13080
13081  GCAAAATTCA AAGTTCAAAG TAGAGTTTTT ACTGAATGCT TGCTTTTGCA CCGTCGTAAA  13140
13141  GTTGAAAAGA ATTTAAATTG AACCATCATA AGCTGCAGAC TGTGCATTTT ATATTGAAAA  13200
13201  GTTAATATTT TTAATTTTTA ATGCAGAGAA GTACCCAAAG CATAAAAACA CAACACGTTT  13260
13261  TCACAAAGCG AACACAGCCA TGGAACCAGC ACCCATATCA ACTAACAAAA TACTAGTTTG  13320
13321  GGCTTTTTTG TACTTTATAC AAATGGACTC ATATAATGTT CATCTTTTGG GTCTGCCTGC  13380
13381  TTTCATTCAA TATTAGGTTT GTGGGTTCAT CTCTGCTGTG TGTAGTTCTT TCCTGTTCTT  13440
13441  TATACAGTGT TCCAAAGTAT AGTATATTAC ACTTTACCCA TTCTACTCTT GATAGTAAAC  13500
13501  GTTTTCACAT TTGGGCTATT ACAAATAGTG CTGCAGTGAA CATTCACATA ACATATCTTT  13560
13561  TGGTGAACAT GTGTTACATT GCCAAGTACA ATTGCTGGGT GATGAGTATG CATACTCTTA  13620
13621  AAACATGGTT GTACCAATTT ACACCTCTAC GACAGTGGTT CCATACCCTT GCCAACTTCA  13680
13681  TTTTGTTCAT TGTAGGCATT CTCTTGGGTG TATAGTGTTA TTGCATTTTG GTTTTAATTT  13740
13741  GCATTTCCCT AATGACTAAT GCAGTTGAAC ACCTTTCCAA ATGATAATTG GCCATTTGGA  13800
13801  CATCATCTTT CTTGAAGATC AAGTCTTGCT CATTTTTCCA ATGGGTCGTT TGCTATTTTT  13860
13861  CTTACTGATT CCCAGGAATC CTTTCTATAT TCTGAATACC AGTCCTTTGT ATTACAAATA  13920
13921  TGTTGTACTC TGTGACTTGT TTTATTTTTC AATTTTCCAG TTTATGTTGT TGATTGTTTT  13980
13981  ACTTCATCCC AGACCAACAG ATTCTAAAGC TTAATTAAGC TTTTTGATCA GAAAAAAACC  14040
14041  CAACTTGGAT ACATCGGAGT AAAAACTGCT TCTCTCACCT GCTCTACTTA TTTCCCTTCA  14100
14101  GCATTTCTAG TGAGTCTTAC TACATGCACA AGTAAGAAAT ACTTTATGC TGTTTAATGT  14160
              GSTO1 Exon 5
14161  TCAGGTTCTG ACTAATAAGA AGACGACCTT CTTTGGTGGC AATTCTATCT CTATGATTGA  14220
14221  TTACCTCATC TGGCCCTGGT TGAACGGCT GGAAGCAATG AAGTTAAATG AGTAAGATAT  14280
```

Figure 1 – page 10

```
14281  TTGAATATTT TGTGCATAAT TTAGGATGAC AGGTGGAATA GTATATATTG ACCTTTCTTT  14340
14341  ATAACAGAAG TTGAAATATT TAATACAACT GGTCTGAATG AGAACAAGCA GACAGGGGAA  14400
14401  TCTTGGACTA TCCCAGGCAT GTCATATACC TACACTAACT ACTCTCCATC ACTGCAATGG  14460
14461  GGCAGGGGAT TTCTGAGACA TGTAGTAAAG TGCTTTAAAA TTTATTCCTT CCTTCCTGAT  14520
14521  TAAAAACCCA TAAGGGGAAG GATATGGTAG CTTACGCCTG TAAGCCCAGC ACTTCGGGAG  14580
14581  GCCGAGACGG GTGGATCATC TGAGGTCAGG AGTTAGAGAC CAGCCTGGCC AATGTGGTGA  14640
14641  AACCCCATCT CTACTAAAAA TACAAAAATT AGCTGGGCAT GGTGGTACAC ACCTGTAATC  14700
14701  TCAGCTACTC GGGAGGCTGA GGCAGGAGAA TCACTTGAAC CCGGGAGGCA GTTGCAGTGA  14760
14761  GCTGAGATCA TGTCACTGAA CTCCAGCCTG GCAAGAGCA AGACACTTCA TCAAAAAAAA  14820
14821  AAAAAAAATT CCATAAGGTT GTAAATTTTT GTAAGGATGT TGTTGCGGGA TTGTACGACC  14880
14881  AGTGTTACCT CCCATTTACC GTAAGATTTC CACATTATTT TCCAAATTCT GTTTTGAGTT  14940
14941  TGGCAGCCAC CTTGCCTTAC TCCGGCTTCT TGGACGATAG AGCTATTCAG GGTTACTTTT  15000
15001  GGTCATAATC TGGGTGTAGA ATAATTAACA TAGAACATTC CTGATTGTAT TCCCTGTTCT  15060
15061  TATTTTAATA AATTGTCAGT TTCTCTCTTT GGGCAAGTTC TCACATTAAC TGAACAAATT  15120
15121  GCTTCACTCT AGTCTCATTC CTTTTGTGTA AAAAAGGGAC CTCTATAGTG TCTTTCAAAT  15180
15181  TGAATATTCT ATTACAGGCA TTTTTAAATA TTTTTAATGA AATATTTAAG GGAAAAAAGT  15240
15241  GAAACTGTAG AGTAATAATT ACATATGGGA GACTCTGTGA TGTCATCCTA GTTGACCTAG  15300
                                              GSTO1 Exon 6
15301  CTCACACCTT TCATTTTTTC CTCTTCCCAC AGGTGTGTAG ACCACACTCC AAAACTGAAA  15360
15361  CTGTGGATGG CAGCCATGAA GGAAGATCCC ACAGTCTCAG CCCTGCTTAC TAGTGAGAAA  15420
15421  GACTGGCAAG GTTTCCTAGA GCTCTACTTA CAGAACAGCC CTGAGGCCTG TGACTATGGG  15480
           [3'UTR of GSTO1 F(730)]
15481  CTCTGAAGGG GGCAGGAGTC AGCAATAAAG CTATGTCTGA TATTTTCCTT CACTAATATG  15540
15541  AATAATAGCA TGCTTTTATT TTACCAAGGT TCAGGTTGCA TGGGATCATC TTCTCTGACT  15600
15601  GATTTGACAT CAACAGCCAA ACGGTGGGGG TCTCCTTAAC GCCCCCCTAC AGAAATGAAA  15660
15661  ATGCATTTCC TGTCTCAGGA TGCTGAAACG ACTCTGAGGG TTCTATCATA GTCCATGCTG  15720
15721  AAACCCCCA AATTATCATC TTTAGCAAAA TCTGGACTTG AATCTTTTTT TTTTTTTGA  15780
15781  GACGGAGTTT CACTCTTGTT GACCAGGCTG GAGTGCAATG GCCTGATCTC AGCTCACCGC  15840
```

Figure 1 – page 11

```
15841  AACCTCCGCC TCCTGAGTTC AAGCGATTCT CCTGCCTCAG CCTCCTGAGT AGCTGGGATT  15900
15901  ACAGGCATGC GTCACCACGC CTGGCTAATT TTTTTGTATT ATCAGTAGAG AAGGGGTTTC  15960
15961  TCCATGTTGG TCAGGCTGGT CTCCAACTCC CGACCTCAGG TGATGGCGC GCCTCGGCCT   16020
16021  CCCAAAGTGG CATGAGCCAC CGTACCCGTC CACAATCTAA CTTTATAACT GCTCACAGGA  16080
                                                             [5'FR F(-1462)]
16081  AATACCCACT CAGTTACCCT GTTGTGTGAT TTCATGAGAT GCTCTCTTGT TGCTTGTCTT  16140
16141  CTGGTTTCTT AGTTGAGAAG CTTTCAATTC CTCCTTCTTT CATTTCCATC ATCAACTTAA  16200
                      [5'FR R(-1348)]
16201  TTTCACATTC TCTCTATTGT TGGCCTGAA GACCAGACGC ACATTACCCG AAAGCTGGGT   16260
16261  GGCTGGGCAG ACTCCTATTT GGTCTCCCTG TCTCTAACCC CTTCAAATCC TTCCTATCAA  16320
16321  ATCCCATGTT GGGCACATAG GTGGTGTCCC ATTTATGTAA TTAAATACTG TGTAGGCTGC  16380
16381  ATCAGTCAAT TCTGCCTACA AGGTTGATGA GTAATAGGTA AGAGCCCCAC TGAGAAATAG  16440
16441  AAATGCCATC TTCCACACAT TTCCATAGCC CACTGCGTTG CTCACTATTC AATTTTTATT  16500
16501  ATCACATCAC CACCACGAGA AGGTAGGTCG GAGAGCAATC ATTTCATTCT ATAGATGATG  16560
16561  CAACTAAGGT CCCGAGGTTA AGTGAGGCCT TAAGGTGCTG GCAGAAAGAT CACACCCAGC  16620
16621  GCACTGCTCT TACCATTGGA ATCAGGGCTG TCGGTCCGCT CCAATTGTCT GGTTTCCTGA  16680
            [5'FR F(-888)]
16681  ACTTATTTTC AAGTTCGCCA TTGAGAGAAA CCTCCGAATG ACTAATTCTT AAATTTAAGG  16740
                                            [5'FR R (-791)]
16741  GTGCATAATA ATCACCTATG GCTCACCGCT GCATTTCCGA TTCAGCAGGC TGGGGTGGGT  16800
16801  AGCGAAGTCT GTATTTCAAA TGAGCCCCTC AACCCAGGTG ACGCAGGCGG TGTGGGGACC  16860
16861  GCATCCGGAG GGCGACCTGG AGCCGACTGA CTTCACAAAG GCCTCCTGCC GCAAACCTTC  16920
                                           GST-Omega 2    [Exon 1]
16921  AGCGGCCACC AAAGCCCCGG CTGCGGCGG CGGACCACCT CTGCTGCCGC GCGCCTACCG   16980
16981  GAGCCGCTTG GCCCTAGTGC TTTCCAGCGG ATTTCCCCTC AGGTGCGGAG CCGGGTGCCG  17040
17041  GGGTCCCACA GCCAACCACT ACCGGTTCCT CTTTCGTCAG CCACCGGCGC CGGCAGGACC  17100
17101  CGCGAATCCC GATCTCCAGG AGCCTGTAAG CAGGCCGCCC ATTGGCTCAG CCGCACTGCT  17160
                                                             [5'UTR F(-368)]
17161  GGGCAGGTAC TTCCAAAGCT TGAGGATTG GCTGATGCTC TGGGCGCCGG GGCTAGTTGG    17220
17221  CGGGTAGGAT CACGTGCGAG GGGCAGGCCC CGTCTAGGCC CCGCCTCCTT GCTGCTGCTG  17280
```

Figure 1 – page 12

```
17281  CCGCCGCCAA TCCTGGTCCG GTTGCCCGAG TTCCCGGAGG TCTCTCGCGG GACCTCTCTC  17340
                                                    [I1R48]
17341  ACCGCCACCG GTGGGTCCGT TCGGCCTGCG TTGTATTGGA AGGGAAGAGG GGTTTGAGGT  17400
17401  CAATTCTGTT TCCTGGGGTT TTCACGAATT TCGGGGCCCA CAGTAGGCTT GCCAACTTTA  17460
17461  ACTTTTGCCT AACACTTTAC GAGAAATCCT ATTTAGCCTT GGCCACTGTT GCATCAAAGA  17520
17521  ATTTCACATC CAACAAAGTG CAGCCTAAGA ATAAGAACA GGTCTTTAAA CCGCATACCT  17580
17581  TTAATTAAGG TGTTCTTATT TTTCTGATT TGGCTGGAAA CAGGCAGAGA CCACCCCAGA  17640
17641  TAACCAGTTC TCAGCCTTCC GTGGGACACC ACGAGTCCCA CCTGTTTACG TGTTTAAGGC  17700
17701  ACTGGCAAGC AGGGGAATTT GGTTTCTGGG AATGTGCTGT CTTTGTGAAA ACTGTGAAAA  17760
17761  GTCTTCCCTG CTACATTGAA ATAATCATAA AATAATAATA GCTAATGTTG AACACTTACT  17820
                                                    [I1R539]
17821  ATGTATCAGA CACATGCTAA GCATTCAATA TTTCTCATCC AGTTTCTGAA TGAAACCTTC  17880
17881  GCAAACCACA TAATGTACTG GTACTATTAG CTACGAATTA CATATAAGAA CACCCGAAAG  17940
17941  TTGTTGTCAT TTGCCCAAGG TCACCCAGCT AATAAATATT GAAGAGATTC GAATCTAGCC  18000
18001  TGAACTCTTA CAGTAAGACC GTTCGTGAGA TGAATTTATA TGTGCTATTT TTCCAGTCTC  18060
18061  TTTATCCAAC AGCTCTGACA GAGGATAGTA TCTACCTTTT TTTTTTTTT TTGAGACGGA  18120
18121  GTCTCGCTGT TCTGCCCAGG CCGGACTGCA GTGGCGCGAT CTCGGCTCAC TGCAAGCTCC  18180
18181  GCCTCCCGGG TTCACGCCAT TCTCCTGCCT CAGCCTCCCA AGTAGCTGGG ACTACAGGCG  18240
18241  CCCGCCACCG CGCCCGGCTA ATTTTTTGTA TTTTTAGTAG AGACGGGGTT TCACCGTGTT  18300
18301  AGCCAGGATG GTCTCGATCT CTTGACCTCG TGATCCGCCC GCCTCAGCCT CCCAAATCGC  18360
18361  TGGGATTACA GGCGTGAGCC ACCGCGCCCG GCCTGTATCT GCCTTTTTGA CCACACCATT  18420
18421  ATTCGTGGGA TTTAACAGGA GTTAATGAGT TAATAATGTT CCTTTTCCAA ACTCAGTGGT  18480
18481  TTTGATTTTA CAAATTATTT GACTTTTCCT GATTTCAGGA TCTTGACAAT TTGCCTTTAC  18540
18541  TTATTCAAAT GTTATTATAC CAAATATTTA TTTAAAAAGT TTTTTTTTTC TTTGATTCCT  18600
18601  CAAGTTGTAG AGAGAAATAG GGATAGGGAA GCAGAATCAA GTAGTTAAAA AGATAGCCTC  18660
18661  ATTTGACCCT GATTTCCCAA TTGGGAATAT GAAATTTTTC CTGAATATAA GCACATTTGA  18720
18721  GAATAGAACC TTTTACCTAA CGTATCTCAC TTTTTGAACT CATTGGACAA TAAGGGAACA  18780
18781  CCCAGTAATA TAATCTTTCA TATAAATTAG GCTTCTAACT TATTAAGAGG AATGTACTCC  18840
```

Figure 1 – page 13

```
18841  AGTCCAGTTT CTGCTACTAT CAAGAGATGG CGTGACAAAA AATTTTGAAA AGTTGCCGAA  18900
                                                                [I1F(1608)]
18901  TGCAAACCAC AGTTCCTCTT CTCAAAACAA ATGCATGTAA ATAGAGTGTA AGCTATTTCT  18960
18961  TTGGTGGCAT TATTTTCCTA GAAGGCTTAA GTCGTTAATC ACCCATGACC GAAGATCCAA  19020
19021  ACATTTTCAA AGCAGATCCG ATCATATTTC AGGTGGCTGA AAATGGATTT GGAGTAGGTT  19080
19081  TAATATGGTC TACTTACAAT TTGTTTCATG ATTGAGTGGG TCAGTATAAT AAAGGTATAA  19140
19141  ACATGAAATA ACATAGAAGG AAAGTTTGCA AGAGGATTT CAAAGAAGTA CCTGTTGGGT  19200
19201  ATTCAAAAGA AAGTAGGGAT AAGCTTAAGG TTAAAATCTT TCTAGGGAAA GTATAGTGTT  19260
19261  CAGAGGTAAG ATTAAAAACC ACATTACTGA AATGGAGTCT GCAGCATTCA GCCCATTCAA  19320
19321  TTGGCATTAA ACTGGTAACT GGTGAAATAA GTATTGTGAG TTGAACTTTA ATTCTAATAT  19380
19381  GCTTGGCAAA GCCGAATCAC AGTGTGCTTC ATCTTTGTGG ATACAAAATT GGAATGCACT  19440
19441  CTGCTATTTA AAATGTGTTC TTACTCACTA GCGTTTGTCA TTAACTTTGA CGTATACTGA  19500
19501  GCTCTTACTA TACTGACGAT GCCCTGGACT ATTTGATTCG ATACTCACAA TTCATAAAGT  19560
                       [I1R(2265)]
19561  AGGTATTATT GGTGTTCTCA TTTTGCAGGT GAGGAAAGTG AAATCCAAAA AGGTTAGATA  19620
19621  GCTTGCCTAA GTGCCAAAGC TGGGTCTCAA AAAGTCAGCC CATTGGGCTC CAGGGCCTGT  19680
19681  TCTGAGAACC TTGACACTAG ATTGTTTCCC TTTAGAGGAG AACAGCTTCC ATCCCTGTCT  19740
19741  TCTAACTCTA CCAAATTAAC TTGGCATTTC AGAACTTGAT TTCCACATA CAGATACACT  19800
19801  TTTCATGAAC ATTTCCCAAC TCTCAGAGTT AGTTTCTTTT AAAAGGTGGG AATGAAAAAA  19860
19861  CAAAACTTGG AAAATCATCC TCTTCTGGCA AAGTAGAAAG GTGGATCCAG GAACCTTTTA  19920
19921  ATTTACAAAT GGAATTCCCA GTTTGGCCAT TATCCAGAGA CCATGGATGG GCAAATTAAG  19980
19981  GCCATTGGGC TAAATCCAAC CAATTGTTGG TTTTTTTATA GCTCAATATC TAAGAATGAT  20040
20041  TTTTTACATT TTTAAAGGGT TGAAAAGAA AAACCAGTCA CAACGTGATA TGTGAAAATT  20100
20101  ATATGAAATT CACCAAGAGT GAGCCCTAAT ATATTAACTA TGGATGTTGG GTGATAATAT  20160
20161  GTCAATGTGG GTTCATTGAT TGTAATAAAT GTACCTCTCT GATTGGAATA TTGATAGTGG  20220
20221  AAGAGACTGT GCATGTGCGG GGGCACAGGG TATATGGGAA ATGTGTATTT TCTGCTCAAT  20280
20281  TTTGCTGTGA ATCTAAAACT TTTTTTTAAA AAAGGCTAT TAAAATACAT ATATGCAGTT  20340
20341  CAAATTCAGT GTGTCCATAA ATACAGCCAC ACCCATTTGT TTATTTATCA TCGATGGCTG  20400
```

Figure 1 – page 14

```
20401  TTTTTACACT ACAAGTGTAG AACTAAATAG TGGAGACCAG ATGGCCTGAA AAGCCTGAAA  20460
20461  TATTTAATAT ATGTAAAAAC ATTTGCCAAT CATTCAGTTC ATGGCATCTG ATAAAGACTA  20520
20521  AGATACTGGT TGAGATTGTT GCCGCTGGAG TCAAACTTCC AGGGTTCCTA GTCCTCCCTC  20580
20581  TTTCACTTAC TAGTTGAGAA GTGCTTAACT ATGCTAGTCT CAGTTTACTC ATCTTTTAAA  20640
20641  GTGAATCAAA ATAGAACAGT TATGGGACTT TTTTTTTTTT TTTTTTTTT TTTTTTTTT  20700
20701  TTTTTTTTTT TTGAGACGGA GTCTCGCTCT GTCGCCCAGG CTGGAGTGCA GTGGCGCAGT  20760
20761  CTCGGCTCAC AGCAAGCTCC GCCTCCCGGG TTCACGCCGT TCTCCTGCCT CAGCCTCCTG  20820
20821  AGTAGCTGGG ACTACAGGCG CCTGCCACCG CGCCCGGCTA ATTTTGTGT TTTTAGTAGA  20880
20881  GACGGGGTTT CACCACGTTA GCCAGGATGG CCTCAATCTC CTGACCTCGT GATCCGCCCG  20940
20941  CCTCGGCCTC CCAAAGTGCT GGGATTACAG GCATGAGCCA CCGCACCCGG CCCAGTTATT  21000
21001  GGACTATTTT AAGAATTAAC TGGGTCAATA CACATGAAGC ACCAAATATA TATTAGTAAT  21060
21061  AATTTATTTT GATTTTGAGA TTTTGCAACC CTCTTATGGC CTTTTTTAGG CTATGGATAT  21120
21121  ATTTTTCTCA ACTATCTTGA AATCTGCTTT TTTTATATGA GGGATGCATG TGTATGCCCA  21180
21181  GAAGTCATCT TACCTACCAG GAGCTCTAAG ATGACATGGT TGTGTTTCTT GCTTCTATTT  21240
21241  TACCATCCAA TTTGTCCTTC TTGATCAGAA TTAGCTCCAA AGTAGTAGAA GTTACTCTGT  21300
                                                     [I1F(-1423)]
21301  TACTTTCTCT GTCTTCTTAA ATGAAAAGTT GTCAGCGTAG CAAGCCGGGA ACCAATATGT  21360
21361  CTTCTCCAAC ACCAGATTTC TTGCTGACAT ATATGCATTT TATTTTCAGA GAACATTTAT  21420
21421  TCAAACATTT TTGCCATTCC CTGATTCTTA TAAAATGTTA ATACTTTCCA TATTATTATC  21480
21481  TAAGCTTATT TCACATGAAA TCATTGAATG ACAGCAAAAA ATGTAGTTGA GTCACTATTC  21540
21541  TGAAGATTTG CAAAGATTCT TATTCACTAG CAAAAAATGT TAACACTATT ATTAACCAAG  21600
21601  AAGTTCTGGA TAGACTGGAA TTCCAAAGGC CAACAGTAC CCAGTTATAA GCTACATAAT  21660
                                                     [I1R(-1042)]
21661  TAGGCTCTGT CATTTTAATA AAAGATATTT AGATTCAAGT ATTATTTGTT GAGCAGCCAT  21720
21721  TACGTGCTAT ATCTTTTCCT GGACTTAAAA TCCTTTCCTC CTAACACTAT TACCAGTTTT  21780
21781  AAAGGTCAAG ACAACGAGTC AAGCTTTGGA CTTTTAAAGT TCTTCAACCC TACTAGCTGG  21840
21841  TCACTTTGGG CAAATAATTT CATTTTCTG AAGCTGTTTT CTGTTTTGAA AAGTAGAAAT  21900
21901  AATATGAGTT GCCTGACTGA GCAATTGTAG GAATCAAGGT AATCTATGGA ATAATTTAG  21960
```

Figure 1 – page 15

```
21961  TCAGTATGAG TGAGACACAG AAAATATTTT TCTTTCCTTC ATGATCTGTT AATCCTACAA  22020
22021  AATGCATTTA CAAGCAATTC CCACATCAGC TCAATTCTGG AAAATTTAAG GAATTATTTT  22080
22081  TTTACCTGCT GAAATTCAGG ATCTCAGCTT ATCAGCATCA GAGCCAAAGC CACGTCTATT  22140
22141  ATCTCACGTA AACAGAAAAG CTGTGCAAGT CGCCCCTATA TGGCTGGGCT GTTGGCAATG  22200
22201  TATCCTTGGC AACTAGTAAG AGTGTTCTCA AAAATTTATG CTGGGGAACG GGGGAAGCTC  22260
22261  ACAAATTGTT CTTTGCCTCC AGGTATCTTA ATTTTATTCA TTGCCAGTTT TTCAGAGCTT  22320
22321  GGGTAAAATC TCACAAGTAG GGCCAGGACT GGGATGAGGC AACTGAGGTG TCTAGGGTGC  22380
22381  AAAATGTGAG TTGTCTAGAC ACCAAAGTTG TCTAGGTGTC TAGGAGGCAC TCACTCTCTG  22440
22441  GGGTATGTGA GATTTCAACA CCAATGACTT TTTCTTTCCT AGTTGCTGTA TCATGAGAAT  22500
                                   I1F(-242)
22501  GTTTGGCCTT ATTATTTTTT AAAGCTGTAC TTACTTACCA AAGAGTGGCC AGTTTAGTGA  22560
22561  TGCAAGAGAT TCAGAATGGG AAAAAAAAG TCAGCTTTAC CCTAGTCAGT TTTGATTAAA  22620
22621  CTCCTTTGAA ATCCATGTTG GAGTTTAAAT GCCCATTCTT GAGGGATTCT TGATGTAGAG  22680
22681  GAGGCCCCTC CAAAGCTTTA AGCACATGTC CAGAGCAAGG GGGAGCTTTT CTGGTGTTAT  22740
                                        GSTO2 Exon 2
22741  TTTGTCTTGT TTTGTTTTTT GCCAGCTCCT ACTCTCGGGC TTCCAAATCT GGGGCGATGT  22800
22801  CTCCCCAGGT TAAATTACCC TAGCTCCTGC TCCAGATCGC TTCCCCGTGC CCGCCAGAG  22860
22861  CCCAGTAGTT CAAAAATTAA ATTTGGGGCA AGGGGTGCGC GCCAGAGCGC AGCTGTTTCT  22920
                                              [E2F(-34)]
22921  GGAGCCTGCG GCAGCGGTGG CGAGCCACAG GCGGCGACC GTGAGCTCCG GGAGCTGCGC  22980
                      1   2  3   4   5    6  7  8    9  10 11 [I2R21]
22981  AAACCACCTG GAGACCATGT CTGGGGATGC GACCAGGACC CTGGGGAAAG GTGAGTGCTC  23040
                            M   S  G   D  A    T  R  T    L  G  K (SEQ ID NO:2)
23041  TCCATGGGGT CCGCGAGCTG GGGGCGCCGC GTGACAGAAA ATGTTGGCTT CGGCGGAGCT  23100
23101  GCCTGGCCTT GGCCTGCAGA CCGGCGGGGC AGGAAGGGAC TTGGAGGGCT CTCCTGAAGA  23160
23161  AAAGCCACAT GCAGCACTGC CCTCTCTGGG ACTTGGGAGT GGAGCTCCC ACAGCCATCT  23220
23221  TGGGATCTGG GCAAGTGAGC GAGCTCCTTC CTCACCGGGC TGACTAGCCT CTCCTTTCCC  23280
                                         GSTO2 Exon 3
                      12 13    14 15 16   17 18 19   20 21 22 23
23281  TGTCCCCCTC CATCGCTGCT CTGCAGAAG CCAGCCCCCA GGGCCAGTCC CGGAGGGGCT  23340
                            G   S   Q  P  P    G  P  V    P  E  G  L
```

Figure 1 – page 16

```
              24 25 26   27 28 29    30 31 32 33  34 35 36    37 38 39    40 41 42 43
23341    GATCCGCATC TACAGCATGA GGTTCTGCCC CTATTCTCAC AGGACCCGCC TCGTCCTCAA    23400
            I  R  I    Y  S  M    R  F  C  P    Y  S  H    R  T  R    L (V) L  K 44 45 46   47 48                                [I3 R(+54)]
23401    GGCCAAAGAC ATCAGGTGAG AAGCGGGAAC CCAGAGCCCC CGAGCAAACC CAGCGCCTCA    23460
            A  K  D    I  R  (SEQ ID NO:3)

23461    CAGGAGCCCG GGAATGTTTA ACATCTGGGG CGCCCTGCTC AGCTTTTACA AGGGGCTCCC    23520
23521    TGTCCCTTTT TTCGGAGGCA AAGTCAACAA ATAGCAAAGG GCGAGCTTTT TTTTAGCGGG    23580
23581    CCCTACTGAA ATGCGGAGCC CTTTTCCGAG TCACGCCTAT GCATGAAACT TCTAGCCCAG    23640
23641    CGCAGAGTAA TGTGAATGAT GGGGCTGGTG AACTGGTTCC CTCCCAGAAT GTTTAAGGGC    23700
23701    ACAGCCAACA CTACTGAGGC CTTACCTGAC TGCTCCACAG AGGTAGTTCC CCCACCACAC    23760
23761    CCCAGGCATC TTAGGTCACT GTTTCCTTTC TTTATTGAAC TTACTGCATC CAGCATTTTC    23820
23821    TTATTTGTTC ATCCATCTCC CCTCCCCAGT CCCCTTCACC CATGTGCGTT CTCGAGGGTA    23880
23881    GGAACTCTGT CTCTTTTATT CATGAGCTAG GAGAGAGCCT GTCACATAGT GGATGCTCAA    23940
23941    AAAACATCTG TTAAATGAAT GAACAAATCT TTCCAAACAA TGAAATAGAA GGAATTGCTA    24000
24001    TCAAGAGGTG TCTGGAAGTT TTCAAGACAC CTTGAAAACT TGAGAAATGG GTACAGATGC    24060
24061    TTCCAAAAGG AAGTTTGCAA AACCAGCTCC TGCAGGTCTG GATTTGGAGG GCAGAGCAGC    24120
24121    TTTGCTGGGA TGTGGACTGC ATAATGCAGC TGGCCTCCAA GCTAGAGTGT TGAGAATATG    24180
24181    TCACTCCAGG CTCCCGACTC TTGTCTCGGA GAGTCCATCA CAAGGGGGTG ACTTCAGAGT    24240
24241    TTCAGACTCA TGTCAGAGAG ATACAAAGAC TAATACAGAG ATGTTTAAA TAAAATTATG    24300
24301    TAAATCTGCC TTGTTGAGTA TATAGGGCCT GTATTCCAC ATTCTTCCCT TTTGCTCAAA    24360
24361    TTAAGCTGAC CTTAAGGTTA CCTGTTTTTT GAGGAAAATA ACAACAACTG ATGTTTTGC    24420
24421    CCATTTGGTG ATAAATTATC AGCTTAGGAG CTGATGTATT TCCTTAGGTC AGCGTTCTC    24480
24481    AAACTTGGCA CTGTTGACAG TTTAGGCCAG ATAATTCTTT GTTGGAGAGG TGGGATAGAA    24540
24541    GCTGTCCTGT CCATCACTGG ATGTTTAGCA GTATCCTTGG TCTCTACCCA TTCAATGACA    24600
24601    GTAGAGTCCC CCTTCCCTAT GCACTACCTT CAGTTGTGAC AACAAAACCA TGTCTCCAGA    24660
24661    CATAGTGATA TGTCCCTTGG GAAGGAGGCC AAAAATCACT TCTAGTCGAG ACCCATTGCT    24720
24721    TTAGGTTGAG ACCCACTGCT TTAGGTCTTG CTATGTGGCC TATGCTGGTC TCGAAATCTT    24780
24781    GGGCTCAAGC AATCCTCCCA CCCTGGCCTC TCAAAGTGCT GAGATTACAG GTGTGAGCCA    24840
```

Figure 1 – page 17

```
24841 CCTCATCCAG CCTCTGCTGT AGGTTTAAGA CAATCTCCTA GACTAAGCAA TGAACGTTCC 24900
24901 CATTTGTTTC CTTTCATGTT TTTAAACATA CGTTCATGCT TCTGGTAACT ATATAGTTAT 24960
24961 CTAAATAATA ATTGTATTAT GTGAACATTA AATAATAATA GTATTATTTG AACATCTAAT 25020
25021 AATTAGAAGA AGAATTAAAA AAGTTATTGC ATGCTTATGT GCCAGGCACT GTCCTAAACA 25080
25081 CTTTATACAT ATCCCCACCA CAGTACCAAG AGATGGGTGT AATTATTAGC CCCATTTTAT 25140
25141 AATTAAGGAC ACTGAGCACA GAGAGGTTAG GAATTCGGTT AAGGTCCCAA GCTAGACCGT 25200
25201 TTATTCTGAT GCCAAAACTC ATACTCTTAA TTGTTAACAT TTACCATATT CTGTTGTGAC 25260
25261 CTGTTAATAC CAGATTTGTA TTTTCAAGCT GTAGAATGTA CTAAACTCTC TAATGCCATG 25320
25321 GTTAAGTGTG TGAGCTCTGA GTCTGTCTGC CTGGCTGTGA TCTTGGCTCT ACTACTTTT  25380
25381 TTTTTTTTA  GATGGAGTTT CTTGCCCAGG CTGGAGTACA GTGGTGTAAT CTCAGCTCAC 25440
25441 TGCAACCTCC ACCTCCCGGG TTCAAGCAAT TCTCCTGCCT CAGTCTCCCA AGTAGCTGGG 25500
25501 GTTACAGGCG CCCGCCACCA TGCCTGGCTA CTTTTTTGTA TTTTTTAGTA GAGATGGGGT 25560
25561 TTTGCCATGT TGGCCAGGCA GGTCTTGAAT TCCTGACCTC AGATGATCTG CCCGCCCCAG 25620
25621 CCTCCCAAAG TGCTGGGATT ACAGGTGTGA GGCACCGCGC CCGGCCAGCT CTACTACTTC 25680
25681 TTAGTGGGTG GTATTGGGTG TGAGATTCAA CCCCCTTGAG TCTTCTTTCC TATGAGGTGA 25740
25741 GCCTACTTCA GGGGGAATTA TGAGGAACAA CTGAGATAAG GCATGGAAAA CATCCGACAC 25800
25801 ATCTTACTGC AGGAAGGAAG ATGATGATGT TATGTATTTT ATACAAAACT TAAACCTTAA 25860
                                                   I3 F(-85)
25861 AACACTAATT GCAAATTTTA ACTTTTAAAC TGATTGCTTC TGCTTTCAAG AAGAGTGCCT 25920
                                                              GSTO2 Exon 4
                                                                49 50
25921 GCCTGCAGAT GCCTCTCATT TTTGTTCTGT CTTGTTTTCC TTTTGCTTTT TAAGACATGA 25980
                                                                 H  E 51 52 53  54 55 56 57 58 59 60  61 62 63  64 65 66  67 68 69 70
25981 AGTGGTCAAC ATTAACCTGA GAAACAAGCC TGAATGGTAC TATACAAAGC ACCCTTTTGG 26040
       V  V  N    I  N  L  R  N  K  P   E  W  Y   Y  T  K   H  P  F  G 71 72 73  74 75 76 77 78 79 80  81 82 83  84 85 86  87 88 89 90
26041 CCACATTCCT GTCCTGGAGA CCAGCCAATG TCAACTGATC TATGAATCTG TTATTGCTTG 26100
       H  I  P   V  L  E  T  S  Q  C   Q  L  I   Y  E  S   V  I  A  C 91 92 93  94 95 96 97 98 99 100 101 102 103 104 105 106 107 108 109 110
26101 TGAGTACCTG GATGATGCTT ATCCAGGAAG GAAGCTGTTT CCATATGACC CTTATGAACG 26160
       E  Y  L   D  D  A   Y  P  G  R   K  L  F   P  Y  D   P  Y  E  R
```

Figure 1 – page 18

```
              111 112 113 114 115 116  117 118 119 120 121 122
26161   AGCTCGCCAA AAGATGTTAT TGGAGCTATT TTGTAAGGTA TATTCAATTT AAAAAGTCAC   26220
         A   R   Q   K   M   L    L   E   L   F    C   K  (SEQ ID NO:4)

26221   TCACACTGTA TTTTACTTTG CATGTCTTTC CCAAACCTCA ACCCATTTTA AAGCCAAATC   26280
                                                  I4R(+140)
26281   ATTGGTGAAA CTGTTTTGTT TTGATACCAT GTGATCCTCA GGAGATTAGC TAGCATGGAA   26340

26341   TTAGGGTAGA GCATGGCCAC TGATATTAAA GGCTTAACTG CTAGGCGCTT CTCCATTTCA   26400

26401   ACTGGCAGGC TCAGGAGGTA TGGTTATGAC ATGGCAATGA CCGTGTAACT TGAAGCAGGA   26460

26461   ATACTGAAAG AACTGAAAAC TGGTGATCCT TAAAGGGAGT ATTTCTCCAG CTTCAGGTAA   26520

26521   AAAGTAATGG AGTGCGAAGA TTATGCATAG AAGGTGATGC TTTTTTATTA TTTTTTTTTT   26580

26581   GAGACGGAGT CTCGCTCTGT CACCCAGGCT GGAGTGCAGT GGCACCATCT CGGCTCACTG   26640

26641   CAACCTCTGC CACCTGGGTT TAAGCAATTT TCCTGCCTCA GCCTCCTGAG TAGCTGGGAT   26700

26701   TACAGGCGCA TGCCACCACA CCCCCTAATT GTTGTATTTT TAGTAGAGAT GGGGTTTCAC   26760

26761   CATATTGGCC AGGCTGGTCT TGAACTCCTG ACCTCAAGTG ATCTGCCTGC CTCGGCCTCC   26820

26821   CAAAGTGCTA GGATTACAGA CGTGAGCCAC TGTGCCTGGC CAGTGATGCT CTTTAGAAGC   26880

26881   ATAAGAGTGC CTGCTGTCCA GGAAATGTGA AGAATAGATA AATGGTGGCA GCTTTGATAA   26940

26941   TGAAAGAAAA AAGAATGGAG AAATTTTAAG ATGGTGTCTT TGAAAAGGAA TTTTTAAAAA   27000

27001   CCTCAATGAT ATTAACAGCT GACATATATC GAACACTTAT GATGTGCCAG GCACTGTCCT   27060

27061   AGTTACTTTG TAGGAGCTAA CTCATTTAAT CCAACTGCCC TTTGAAGTGG GTACTGCTAT   27120

27121   CGTATCCATT TTTCAGATGA GAACACTGAG GCTTAGAGAG GTTGAGTGTC CCACCTAAGA   27180

27181   ATGTATAGCA TGGAAGCAGC TGATCAAGTA AGGAGCACTG GAGAAACCCT CCTAAAGCAC   27240

27241   CCTGCTTTCC CAGGGTACTA TAAGAAGTAG ATTCCTACTG AGAACCGGAA CCACAGAGAA   27300
                                                                [I4F(-94)]
27301   AACCTAGTGC CTCTCACAGG GAGCTGGGGG GTCTGATGTG GGTGTTGCCC TGTTAGGCTG   27360

27361   GAGTTATAAA GCTTCGCTGC CTTTTCAGGC AGAACAGGAA CTGGAAGTTT CCACAGACTT   27420
                                    GSTO2 Exon 5
                                   123 124 125 126 127 128 129 130 131 132
27421   CTCCACTGAG AACCTGTGTC CTCTGATTAG GTCCACATT TGACCAAGGA GTGCCTGGTA    27480
                                         V   P   H   L   T   K   E   C   L   V 133 134 135 136 137 138 139 140 141 142 143 144 145 146 147 148 149 150 151 152
27481   GCGTTGAGAT GTGGGAGAGA ATGCACTAAT CTGAAGGCAG CCCTGCGTCA GGAATTCAGC   27540
         A   L   R   C   G   R   E   C   T   N   L   K   A   A   L   R   Q   E   F   S
```

Figure 1 – page 19

```
              153  154  155  156
27541 AACCTGGAAG AGGTACAAAA AGGGGTCCCT CTCCTGGTCA GCTACAGTGG AGGAAGCTAG 27600
       N    L    E    E  (SEQ ID NO:5)

27601 GCAGGGTCGC TAACCTGGTC ACTCTAACAC CAGCTTTCAC AGGCTTATTC TTTCTGCCTT 27660

27661 TGATAAGTCA GACTTCTGAT CATCTGATTG CATGTTTGCC CTCCTCTAAC CTGGTCTAGA 27720

[I5R(+227)]
27721 ATTATTCTGG AAAATCTGAT GAGGAGTTGG GGAGGACATG CCATGAATTG CTTCCTTTCC 27780

27781 CAGAGTCACC CCATCTCCCT GAGTAGCTCT GCATGGCTTC TGTAGCTTCT GCCAATGAGG 27840

27841 TCAAGGTCTG TAAAGGTTAG GGGTTGTGTT TGGCTGCTGA AGTCTAACTA CTGTAAATTC 27900

27901 ATGTTGTAAG GGTTTACTCT CTCACATAAC ATTCTTTCTC ACGTATTATA AGGGTTTATT 27960

27961 CTCACACATA CGGTGGCTCA CACCTGTGAT CCCAGCACTT GGGGAGGCTG AAGCAGGAGG 28020

28021 ATCACTTGAG CCTAGAAGTT TAAGACCAGC CTAGGCAACA TAGCAAGACC CCTCCTCTAC 28080

28081 AAAAATAATT TTAAAAATTA GCCAGGCATA ACGATGTATA CCTGTAGTCC CAGCTACTTA 28140

28141 GGAGGCTGAG GCAGGAGGAT TGCTTGAGTC TGGGAGGTCA AAGCTGCAGT GAGCCATGAT 28200

28201 TGCACCACTG CACTCTAGCC TGGGTGACAG AGTAAGTAGG ACTGACAAAA AAAAAAAAA  28260

28261 AAAAAAAAAA AAGCCAGAGG TAGGCAGTTC AGGCCTATCT TGATGGCTTC TTCATGACAT 28320

28321 TATCAGGAAC TGAAGCTTTT TCTCTTTATG GGCTCTGTCA TCCTTAGCAC AACTTAGTAC 28380

28381 AAGGGTATCA TCCTCAAAAT AACAAGATAG CTGCTGTCAC TGCAGCCATC ACATCCAAGT 28440

28441 TCCAGGCTCT GAAAAGGAGA ATATAAAGAA AAAAATGGCA AATGGTCATA CCCCTTTAAA 28500

28501 GGGCTTTAAA TCCTACCAGA AATTCTACTC AATGGCTATT TACATTTCGT TGGCCAGAAC 28560

28561 TTAGTTGTGG GGTCATAACT ATCTTAGAGA AAGCTGGGAA ATACAGTCTT TTAGCTGGGA 28620

28621 TACCCTGAAT AAAATCAGAG GTCTGTAATT AAGGAAGAAG GGGGAAATGG GTGCGGTGGC 28680

28681 AGGAATACTC TTTGCCAGTA GATGCTTCAT TAACCTGGCA GTAATGGAGC TACTTATCCT 28740

28741 GTACTTCTAG AATAATCAGG AAGGCAGTTC TTTTACTTCC TTTATTTTTG CTCCAGAAAC 28800

28801 TGACAAATTC ACCTTATGGG TGGGTGGTTC CTCTATTGGC AGCCAGAGAA TACAATTTTT 28860

28861 TTCCCCTTAA GGGAAGACTG GTTATTAATA CTCTTCCATT TGACCTTTAT CAAGTGGAAA 28920

28921 CAGATTAAAT GTATTGATAT TTCCAGTTGC CTATCTCAAA TTTGTACGAT TAAGTATTTA 28980

28981 TGGATGACGA ATGGTCATGT GTAGGAAATG TCAACCTTTT GTCCTGAGGT CACCAACTGT 29040
```

Figure 1 – page 20

```
29041  GGCCTTGACT CCAAGGAGGC CATATGATGT GGTGGAAAGA ATCTTGGATC TTAGGCTTGG  29100
29101  CTTTACTGAA TTCCAGAACC TTGGGCAATG TTCTGTACCT CTCTGGGCCT TGGTTTTCCC  29160
29161  ATGTGTAAAA TGAGGGATTA TTTTGAAATG TGTGTTCCTC AGAGCCTCTG GGTTCTGCAG  29220
29221  GGGACTGCCC AGTGAGTGGA GGCCTGGTAG ATTGTTCTAG ACACTGCTTT ACTTAGGTCA  29280
29281  GCACTGCCTT CAACCACCAT GTTCAACCTG ACATCTAAGA AGATGGCATT TGGGGAGAGA  29340
29341  GGAGAGCTGC TGCTTTAAAA AAGAAGTTCG AAAATCTTGT GAATAGAGAA TTTATAGTCT  29400
29401  ATTTTAAAGA TCAGCTGAAT GGACCCCATC ATGCCTGGTT ACCTTCTCAC AGATAAACAA  29460
29461  ATACTGGACC AGGGAAAGGA GCTGGGAAAA AAAAAACTCT TTGAATTCAA CGATACAGTA  29520
29521  ATTGAAACAT TTTCATCAGT TTCCCTTCTA CCTCCATTTG GATGATGGAT GAACTTTTTA  29580
29581  AATTACAGAT TGCTAGATGA AAGTATAGGG TTATGATGGA GATACAGTTC TTCTTCAGTC  29640
29641  GGGGGTCTTT TCCAGGGCAA ATGAACCAGT ATTTTGTGCC ATGAATCGTG CTGCAGATAC  29700
29701  TTGCATACAT CATCTCATTC AATCTTTCCA ACAACCTTCT CAGGTACAAA TGGTACTAGT  29760
29761  CCTGTTTTGC AAATTGGAGT GGCCTCTCTG TAAAGGCTCA GAACTAGGTA CTAGGAATAA  29820
29821  AAAGAAATTA AAGACCCTCG AGGGGCTCAA AGCCTGGACA GGGAGATAGG CTGTTAAGCC  29880
29881  CATTTAAAAC CTGGGTGTGT TGAGTGCTAG GCTGGAGACA TGCATACAAG AAGGCTGGTC  29940
29941  TGTGGGGGTA GATAATGCCT CTGTTGACTC TTAGGATGAA TTAGAGGCAC AAGGGTGAGA  30000
30001  GCCTGGTGTG TTCGGCAAAC AATAATCAGT GAGGGGTTGA CAGCGAGGGA GTGATTGGTA  30060
30061  AGAGGTGAAT GTGGAGGGTG GACCAGAGTC AGATGCTAAA AGGCCTTTTC CACTGTGCCC  30120
30121  AGGGATTTGC ACTTTATTTC AGAGTTGATG GTGAGTAATT GAAGCCTGTC AAGCAGGAGA  30180
30181  GTGGTGTACT CCTTCATGCT TTTAAAAGTA TTCAGTCCAT CACTTGAACC CAGGAGGGGG  30240
30241  AGGTTGCTGT GAGCCAAGAC TGCGCCACTG CACTCCAGCC TGGGCAACAG AGTGAGACTC  30300
30301  TGTTTCAAAA AAAAAAAAAA AAAAGAAAAG AAAAGAAAAA GTATTCAGCC CAGCTGAGCA  30360
30361  CAGTGGCTCA TGTCTGTAAT CCCAGCACTT TGAGAAGCCA AGACGGTAGG ATCGCTTGAG  30420
30421  CCCAGAAGTT TGAGAACACC CTGGTCAACA TGGCAAACCT CCATCTCTTT AAAAAATACA  30480
30481  AAATGTTAGC TTGGCATGGT GGCTTATGCC TGTAGTCCTA GGTACTTGGG AGGCTGAGAT  30540
30541  GAGAGGATCA CTGGAGCCTA GGAGGTTGAA GCTGCAGTGA GCTATAATTG CACCACTGCA  30600
30601  CTCCAGCCTG GACAACACAG TGAAACCCTA TCTCAAAAAA AAAAAAAAG AAGAAGAAGA  30660
```

Figure 1 – page 21

| | | | | | | |
|---|---|---|---|---|---|---|
|30661|AGTTCAGCCC|AGCAAGAATG|TAGAGGATGG|ATTAGAGTGT|CCAAGAGGAG|GGACTGGGAA|30720|
|30721|GGGACAAAGA|GGACCCCACT|AACGAGGGTT|GGAGAGGGAG|GTTTAATTAG|AGAGATTTTG|30780|
|30781|AGGAACTAAG|ATGAGATGAA|ATCTGAGGAA|GGAGTAGGAG|TTATGGAGGA|TGGTTTCCAA|30840|
|30841|GTTTGTGGCC|GGTAAATGTG|ATGCTTTTCA|CTAAGAGTTT|GAGGGAAGAC|ACATTTTGTC|30900|
|30901|AAATTTGTGG|TGTTGATGGG|ATATTCATAT|GCGGGCAGAG|CTTAGAAGAA|CAATGTATGG|30960|
|30961|TCTCTACTGG|ACCTTTGGAA|TGGTTTTATG|GGCTAGGAGC|TTTCACCAGA|GAGTTTAGGA|31020|
|31021|ATGTCATTAG|TGGGGTGGTG|ATAAATGTTT|AAGAATCAAT|TTTCTCTTAA|AAGAGAAAGA|31080|
|31081|AAAAGAAAAA|GCACGGATTT|ATAGCATTTG|CTGATTTGGG|TGGTGTAAAC|ACTTCCGTCA|31140|
|31141|AGGTTAATTT|TGAGCTACCA|ATGTGCTATT|TCTAAACTCA|AGAGCTGGCA|AAAGATGTGG|31200|
|31201|GCAGCTCCAG|CATGTCACTG|AATAAGAAAT|TTCACTTTAT|CTTCAATAAC|TGAGCCCCAG|31260|
|31261|GAACACTGTT|GTTAACCAGC|CTCTATATAG|GTAGCTTTCA|CTAACCAGCC|TCGGTGTAGG|31320|
|31321|TAGCTTTCAC|TGATGCTATT|TAAGGACCAC|TGAGTACTCC|ACATTGTCCT|AACAGGTTTG|31380|
|31381|AATGTGGTTT|TGTCCCATAG|AATGTTAGCA|AGAATTGTAG|CTATGGCTGG|GCGTGGTGGC|31440|
|31441|TCACACTTGT|AATCCAGGCA|CTTTGGGAGG|CCAAGGAGGG|AGGATCACCT|GAGGCCAGGA|31500|
|31501|GTTCAAGACC|AGCCTGGGCA|ACACAGTGAG|ACTATGTTTC|TACTAAAAAT|TAAAACATGA|31560|
|31561|ACTGGTCATG|GCAGTGCGGG|TCTGTAGTCC|CACCTTCTCT|GGAGGCTGAG|GCGGGAGCAT|31620|
|31621|CTTTTGAACC|CAGGAGTTTG|AGCTTGCAAT|GAGCTATGAT|CGTGCCACTG|TACTCCAGCC|31680|
|31681|TGGGTGACAC|AGCAAGACTC|TGTCTCAAAA|ACAAATAAAC|AAAGAATTAT|AACTACAATG|31740|
|31741|TAGGAAATAT|TGAAATCTGA|AAACATGACC|AATGTACTTG|AATTATGCGA|TCTGTTCCTT|31800|
|31801|TAAATGCCAA|AATATTTATT|CCAGGAGATT|CTAGTGAAAT|TGAAATTTAT|CAGAATAATT|31860|
|31861|CTAATGGAGA|GGATCCCCTG|ATTTATGTAA|CTCTTTCACA|TGGTTTTGCA|CAATCAGGAT|31920|
|31921|TTTTTGTGAG|CTAAAAATAT|ATTAAATACT|CATTGTCTTT|CTGAGTGATA|AGCAAGCCAA|31980|
|31981|GATTTCATGC|ATAATCTTCT|GCTATGTTAT|CCTGAAACAG|AAGGCTCAGT|TAACCTTTTG|32040|
|32041|TGGCCTTAAA|CTCTGACACT|TTCTTCTTTT|GAAATAACTG|CCTTGTCTAA|CTTTTTAAGT|32100|
|32101|TTTTTTTTTT|TTTGGCTTG|TTTTTTTGTT|TGCTTGTTAG|TTTTTTAAAT|CTAGTTTCAG|32160|
|32161|GTGGGTTCAG|TGGCTCATGC|CTGCAATCCC|AGCACTTTGG|GAGGCCGAGG|CGGGCAGATC|32220|
|32221|ATTTTAATCC|AGGAGTCCGA|GACAAGACTG|TACAACATGG|CAAAACCTTA|TCTCTACAAA|32280|

Figure 1 – page 22

```
32281  AAATACAAAA ATTAGTTGGA TGTGGTGATG CATACCCGTG GTCCCTGCTA CTTGGGAGGC  32340
32341  TGAGGTGGGA GGATCACTTG AGTCCAGGAG GTCAAGGCTG CAGTGAGCTA TGATCATGCC  32400
32401  ACTGTACTCC AGCCTGGGTG ACAGAGTGAG ACTTTGTCTC AAGAAAAAA AAAATTAAGT  32460
32461  TCCATCAAAA TCAAAGATTT ATTGTGCTTG TTATATAACC ACATTTTTCT CTAATATCTT  32520
32521  TTACAATTCT TTGAGATATA TTACTGCCAC TTTTATTATC AAACTAGCAG CCTGCTCACT  32580
32581  GGCTTTCCTG TTCTGAACAT TGGCATGAGT TTTAAAACTA TGACACTTGT CTTGTCTTGC  32640
32641  TGCACTTTAT GTCTTCAAGC AGATTTTCTA GCCCTTACTG AATCATTACT CTAAGCAGCA  32700
32701  CACATTTTTT AGTTTTATTC TTTTTCAGGT ATTGACTTTC CCATTTCAGA ATGGGACTTG  32760
32761  AGCCAGGCTT CATTTGATCT TTGTGGATTT GAATGTGGCA GGACCTCTTG GTGTCACTTT  32820
32821  TTATCTGTGC CTTCCAAAAA TATTTTCATT ATGGAAGTAG TCAAATCAAG TCCAAGTGCA  32880
32881  GTGAAAGGTG GATTTGGTCA GATTTCCTTG AGGCTTTGGA GTTTTGCTTT AAATCTAGAA  32940
32941  AGTGTTCGTG GCTTCTGAAT TGGTTCTGCA CTCTGACTAT TGCTTGGTCC TTTCTTCGTC  33000
33001  ATCATCAGAG CTCCATAAAA GAGAGCGGGG AGGGGATAAC ATAAATAATG CTGAAATAGC  33060
33061  CCTGAGGGAT GAGACATGGC CCAGCAACTG AAGCCTTCGT CTGCCCGTGG CCACAGGGCA  33120
33121  CTTTATGGTT TTGCTTCTTG TCATTCAACC ACCTGCCTTG GGGTGCTTCA CTTTGCATTT  33180
33181  CCACGCAGAG TTTCCCGCAT TGCCAAACTT GATCATGTGC CTTATGTGTA GCAGTTTGCA  33240
33241  TGAGGTGGAA TTTGCATAAA TTATGTGTGC ATCACCCAGG AGCATCTGTA GTTAAATACT  33300
33301  TTATTGATTC TAAATTTTGC CCATAATCTT AATTTTTTAA TTATTTTATT TTCTTTTCCT  33360
33361  CTTTTAGAGA TTGGGGTCTC TCTCTATTGC CCAGGTTGGA GTGCAGTGGC ACAGTCATGG  33420
33421  CTCACTGTCG TCTTGAGCTC CTGGGCTCAA GCAGTACTTC CACCTCAGCC TCCCGAGTAG  33480
33481  CTGGGATTAC AGGCTGAAGC CACCGAGCCT GCCTCCGTTA TCTTAATTAT TATTATAATT  33540
33541  ATTTTTTTGA GTCAGGGTCG CACTCTGTCA CCCACATTGG AGTGCAGTGA CACAATCACG  33600
33601  GCTCACTGCA GCCTCAGCCT CCTGGGCTCA AGTGATTCTC TCACCTCAAC CTCCTGAGTA  33660
33661  GCTGGGACCA CAGGTTCAGG CCACCATGCC CAACTGTTTT GTTTTTGTTT TTATTTGTTT  33720
33721  TAATTTTTTG TGGAGACGAG GTCTCACTAT GTTGCTCAGG CTGGTCTTGA ACTCCTAGGC  33780
33781  TCAAGTGATT CTCCCACTTC AGCCTCCCAA AGTGCTATGA TTACAGGCAT GAGCCACTGC  33840
33841  ACCTGGTAAT CTTAATTTTT AAACTGTTCT TCTTCTCAT CAAAAAAGAC ATTTATTCAA  33900
```

Figure 1 – page 23

```
33901  GTTAGATTAT ATTGTCTTGG TTTAGTTTTG CTTTTGCTCT TTCTTAATTT TTATTAATTT  33960
33961  CCAGTGATGA AATTATTTAT ATATTGTTTA ATTGTTTCTC CTTTGATATC ACCAGGATAG  34020
34021  GAAGAAAAGA AAGTTTATAC CTGGTTAATT CGTCACTGAA AACAATTTTC TGTATCCTTT  34080
34081  TATATATAGT AGACTACAAG CTAAATTTTT TATCATCTAA GTTAACATGT CTATAAACTA  34140
34141  AATTCATTAT TACTAGCTAT TTTTAATAAG TTATTGAGAT ATAATTCATA TGCCACAAAA  34200
34201  TTCACCCTTT TCCAGTGTAC AATTCACTGG CTTTTAGTAT ATTAAGTGAG TTGTGCAACT  34260
34261  ATCACCAGTA TTTAATTTCA GAGCGTTTTT TTTATCATCC CCAGAAAAA CTGCTCACTT  34320
34321  GTAAGCTGTC ATTTTCCATT TCTTCTCAAT CCCTGTGGCT GTACGCAGCC ACTGATCTGC  34380
34381  TTTCTGTCTC TATGGATTGA CTTATTCTAG ACACTTCATA TAAGTGGAAT CATACAACAT  34440
34441  GTAGCATTTC ATGAGCTATT TTCACATACC ATAATGTTCT TAAGGTTCAT CCTTCATTCT  34500
34501  TTTTTATGGC TAAATAATAT TCCATGTGTG AATACGCACA TTTTGTTTAT CCACATCTGG  34560
34561  GAAGGTTCCA CTCTTGGAAC TAATATGGAT AATGTTGCTG TGAACACCAT GCAGGTTTTT  34620
34621  GCATGAATAT ACGTTGTTAT TTCTCTTGGA TTTGCTAGCT GATTTAGCAT GTTTACTAAC  34680
34681  ATGCCATTTT AGTTGTAACC ACCATTCTTT CACACTTGGG AACTGATTAT CCCTGACTCA  34740
34741  GGATGCCTCG TTAAGTGTAT TAGTGCTGTT GCTAGTTGGG TTACTTCCTT CATCATCCAA  34800
34801  TTCTGACAGC TGCTAATATT TGCTGTACTT CTTTCAATAG CTTTCTGATA TACCCTTTCC  34860
34861  CATCACATAA ATAATAGAAT AATAATTATT CTTATTATTT AAAAATTAAT TTTACTCTTC  34920
34921  TCCAATTATA AAGTAATACT TGTTCATTAG AGAGAATTTG GAAAATACAG GAAAACATAG  34980
34981  AAACTAAGGA AAAAAAATTA TAATCCCACT ACCCAGAAAC AACCACTGTT ATTATCTTGG  35040
35041  GGACTTTTTT GTTTTTGTTT TCTGTCCTTT TCTGCTATGT ATATTTTATG TAGTTGAAAC  35100
35101  TTGGTTACTA TTATGATGTA AATATTCCCC ACACCCCTG CCATTTTATT TTGAGACAGG  35160
35161  GTTTTACTCT GTTGCCCAGG CTGGAATGCA GGGTGCAATC ACGCCTCACT GCAACCTTGA  35220
35221  ACTCCTGAGC TCAAGGGAGC CTCCCAACTC AGTCTCCTGA GTAGCTGGGA CTACAGGCAT  35280
35281  GTGCCACCAT GCCTAGCTAG TTTTCTTTTT AACTTTGTA GAGACAGGGT CTCCCTCTGT  35340
35341  TGCCCAGGCT GGTGTCGAAC TCCTGGGCTC AAGTGACCCA CTTGTCTTTG CCTTCCAAAA  35400
35401  TGTTGGCATT ACAGGTGTGA GCCACCACAC CTGGCCAATT TTTATAAACT CTGTAAATGC  35460
35461  TTATTTACAT ATATAAGAGT GTTCCTTAGA GCAGCAGCAT TATTTGTGAT GATGACAAAT  35520
```

Figure 1 – page 24

```
35521  TAGGAAACAA TATTCATTAG ATGGTGAGTG GTTAAGTAAA TCATGTCTGT CTTGTGGAAT  35580
35581  TCTGTGGAAC GGCTGAAAAT GAATGAGGTA AATCTATGTG TACTGACATT AAAAGATTGC  35640
35641  CTAGAAATAT TAAATGAATC ACACAGTAAT ACAGGTGGTA TGATCCCATT TTAGCAGAAG  35700
35701  AAAACAAAAC TGAACCATGC AGGTGTGCAC ATACATGTAA ATAAGTGGCT AGAAAAGTAT  35760
35761  CTAGAGAGAA ACACATCCAC CTCCTAGTAA TGTCTCACAC TGGGAAGGGG GCTGATTAGA  35820
35821  ATTAGGGTGG GTAAGAAAAG TGGTTAAGGG CAGGGACCGG GAGGGAAGAT TTTGTCTTTT  35880
35881  ACATTATTTT CTGTGTTTGA TTTTTTTTTT AATGATGGGA ATGTATTTCT GTATTAAATA  35940
35941  TGTAAGTTTT AAAAGTAGAA AAAAACACTT TTTTTTTTTT TTTTTGGGA CGGAGTCTCG  36000
36001  CTCTGTCGCC CAGGCTGGAG TGTAGTGGTG CTATCTCGGC TCACTGCGAG CTCCACCTCC  36060
36061  CAGGTTCATG CCATTCTCCT GCCTCAGCCT CCCAAGTAGC TGGGACTACA GGCACCCGCC  36120
36121  ACCACGCCCG GCTAATTTCT TTTGTATTT TTAGTAGAGA TGGGGTTTCA CTGTGTTAGC  36180
36181  CAGGATGGTC TCCATCTCCT GACCTTGTGA TCCATCTGCC TCGGCCTCCC AAAGTGCTGG  36240
36241  GATTACAGGC GTGAGCCACC TCACCCGGCC GAAAACACTT TTAATGTCTG CATACTTTGC  36300
36301  CATGTTTATA AACCATAAAG TTATTTATCC AGCACACTAA TTAGGAGTGT TTAGATGGTT  36360
36361  TTCAGTCCTT TACTGTTTTG AATGGTGCTG CAGGGAACAT CAGCTTCTTT GCATAAAAAG  36420
36421  CATTTCTCT ATTTTAGAAT ATGTTCTTAA GCTGGACTCT CAGGAATGGA ATTACCAGAT  36480
36481  CAAAGGGTAT AATGAGCACA TTGGAGGCTT GGACTGTATT TCACTAAATT GCTTCCCAAA  36540
36541  AGACTTGTGT TGTTTGCCCC TCACCAGCAG TATGTGAAAA TGCTCTTTGC CCTATATCCT  36600
36601  TTTCACTGGT GGGAGACTTC ATTCAAAAAG ATATTTGTTT GTTGAATAAT ATTTGCTGTG  36660
36661  GAGATACACT GTAGTTCCTC ATTGTTGACT TAATGCATAT TTCTTTGATG GCCAGGGAAG  36720
36721  TGGAAGGTTT TCCCGGAAGT ATGTCATCCC TTGCTCCTGG TCTTGCAAAA TTTGTCTGTT  36780
36781  CAGTTCAGGG GCTTTGCCTA TCTGGCCATC AGAGTCTTAC TAATTTTCTT TGTTGATTTG  36840
36841  TAAAAGTTCC TTTTAAAGCG TTCCTTGTAT AGAAAAGATA TTTGACTGGT TTTAAAACAC  36900
36901  ATTTTGTTT TCTTTTGACT TTTAATTTGG CTTATATATT TTTGCATATG GAAGTACAGC  36960
36961  ATTTGAAAGT ATTGTGCTAT AAGGCTTTCC TTATATGTGC TATGATTTCC TCCACTGTTT  37020
37021  TATGTGTAGG AAGTCCTCTC CCCACTTCAG AGACTTGATA AATATTCATT TATATTTTCA  37080
37081  TCTACCACCA ATCACTTTAC AGACATTTGA CTGGTCAAGC ATTACCCTCC TAGCTTTTCC  37140
```

Figure 1 – page 25

| | | | | | | |
|---|---|---|---|---|---|---|
| 37141 | CCCCACACTA | TCTTACAAAT | ATATTGTGAT | TTGTTTTAGT | TTTTGTTTTT | TGTTTTTGAG | 37200 |
| 37201 | ACAGGGTCTC | ACTCTGTCAC | TCAGGCTGGA | GTGCAGTGGC | ATGATCATGG | CTCACTGCAG | 37260 |
| 37261 | CCTCGACCTC | TCAGGCTCAG | GTGATCTTCC | TACCTTAGCC | TCCTGAGTGT | CTAGGACTAC | 37320 |
| 37321 | AGGCACCACT | ATGCCTGGCT | AATTTTGTGT | ATTTTTTGTA | GAGATGGGAT | TTTGCCATGT | 37380 |
| 37381 | TGCCCAGACT | GGTCTCGAAC | TTCTGGGCTG | AAGCGATCCT | TCCACCTTGG | TCTCCCAAAG | 37440 |
| 37441 | TACTAGGATA | AAAGGTGTGA | GCCACCACAC | CCAGCCCTAC | AAATATATTT | TGAAGATACG | 37500 |
| 37501 | AATTAAGCTC | ATTAAAAGGA | TGCCAGCATA | GAATTTTCAG | AGTGGTCCTT | TAATCCCCAA | 37560 |
| 37561 | ATTTTGACAG | TTGTATTCTG | CACCTTCATG | GAGAATCTAG | GTCATAACTG | ATGGGCAGCA | 37620 |
| 37621 | GGAGGGGCAT | GTTCTGCTGC | AGGTCCTCCC | TCTAAGGCTC | CTTCCCAGAG | GAGAAAATGG | 37680 |
| 37681 | TCTTAAATAT | GCCCTAGGTT | TGTTCCACAC | CCTAGGTTTG | TTTTACAGGG | AACTGGGTCA | 37740 |
| 37741 | TCACATGGTT | AGCTCAGCCT | CAGCTATATC | ATTTTAGCAG | GGATCTGAGA | TTTGAAATCT | 37800 |
| 37801 | TAAGAACCTC | CATTTATCTT | TTATGAGCTC | AAAACATTTC | TGCCCTCCAA | AAGACTTGAA | 37860 |
| 37861 | TAGACATTTC | TCAAAAGAAG | ACACACAAAT | GGCAAACAGA | CATATGAAAA | GGTGCTCAGC | 37920 |
| 37921 | ATCATTGATC | ATCAGAGAAA | GGCAAATCAA | AACTACAATG | AGATATCATC | TCACCCCAGT | 37980 |
| 37981 | TAAAATGGCT | TACATCCAAA | AGACAGGCAA | TAACGAATAC | TGGTGAGGAT | GTGGAGAAAA | 38040 |
| 38041 | GGGAACCCTC | GTTCACTGGG | GCGGGAATGT | TAATTAGTAT | AACCATTGTG | GAGAACAGTT | 38100 |
| 38101 | TGGAGGTTCC | TCAAAACACT | AAAAATTGAG | CTACCATATG | ATCCAGCAAT | CCCACTGCTG | 38160 |
| 38161 | GGTACACACC | CAAAAGAAAG | GAAATCAGTA | TATCAAAGAG | ATACCTGGAC | CCTTATGTTT | 38220 |
| 38221 | GTTGCAGCAC | TGTTTACAAT | AGCTAAGATT | TGAAAGCAAC | CTAAGTGTGC | ACGAATAAGG | 38280 |
| 38281 | AATGGATAAA | GAAAATGTGA | TACAGGCCGG | GTGTGGTGGC | TCACTCCTGT | AATCCCAGTA | 38340 |
| 38341 | CTTTGGGAGG | CCAAGGCTAG | CGGATCACTT | AAGGTCAGGA | GTTCGAGACC | AGCCTGGCCA | 38400 |
| 38401 | ACATGGTGAA | ACCCTGTCTC | TACTGAAAAT | ACAAAAATTA | GCTGGCATGG | TAGTGCATGC | 38460 |
| 38461 | CTGGAATCCC | AGCTACTCAG | GAGGCTGAGG | CAGGAGAATT | GCTTGAATCT | GGGAGGCAGA | 38520 |
| 38521 | GGTTGCAGTG | AGCTGAGATC | ACACCACTGC | ACTCCAACTT | GGGTGACAGA | GTCACACTCT | 38580 |
| 38581 | GTCTCAAAAA | AAAAAAGAA | AAAGAAAAT | ATAGTACATA | TACACAATGG | AGTACTATTT | 38640 |
| 38641 | GGCCATGAAA | AGAATGAGAT | CCTGTCATTT | GCAGCAACAT | GGATGGAACT | GGAGATCATG | 38700 |
| 38701 | TTAAGTGAAA | CAAGCCAGGC | ACAGAAAGAC | AAACATCACA | TGTTCTCACT | TATTTGTGGA | 38760 |

Figure 1 – page 26

```
38761  ATCTAAAAAT CAAAACAATT GAACTCATGA ACACAGAGAG TAGAAGGATA GTTTGCAGAG  38820
38821  GCTAGGAAGG GTAGTGTGAG CTGGCAGGGA GGTGGGGATG GTTAATGGGT ACAAAAAACA  38880
38881  GAAAGAATGA ATAAGACCTA CTATCTGATA GCACCACATG GTGACTATAG TAAATAATAA  38940
38941  CTTAATTGCA CATTTAAAAA TAACTTAAAC AGTGTAATTG GGTTGTTTGT AATTGAAAGG  39000
39001  ATAAATGCTT GGGGGAGTGG ATACCCCATT CTCCATGATG TGCTTATTGC ATACTGCATG  39060
39061  CCTGGACCAA AATATGTACC CCATAAATAT ATACACCTAC TATGTGCCCA CGAAAAATAA  39120
39121  AATTAATAAA AGATTTCTGC CCTGGAGTTG AGTACTTTTC CACTGCTTCT GGAAAAGGGC  39180
39181  CAGTATTGCT GATGTACTGG CATGTTGCTT TGTGTCTTTT TAGGGGCCAC AGAGGGTGGA  39240
39241  GGATGGCTTC TGCTTTTTTG GGGGGCAGAG AGTAGGGGAT GACCTCTGCA TTTTCAGAAC  39300
39301  GATTTTCATG AGGAAAAACT TTCTTCCTCC TCCAGCAAGT ACAGCAGCCC CCACTGGGAG  39360
39361  CCACCACACT GTTTCGAGAT TGGGGGCTTG GGATTTCTTG GCAATGGTGT AGAGGATGGT  39420
39421  GAAGGTGAGC TGGCCTCTTC AAGGTTTGAA GCTCAATTAT TGAGGCTGAA CCAAAGAGTT  39480
39481  GAAGACTGGA GCTCTCTCGA ATGCCTGGTT TGGAGATGTC TGGGATTCGC TTCTCCTAAT  39540
39541  GATCTTGCTT CTCTCGCGAA AACTGCAGAT TTCTTCATCC TCCGGTTGAA CGTTCTTGGG  39600
39601  GAGCCGCGGC CGACGCGCCT CGCACTGATG GCCACCAGGG GGAGCCCCGC GCGCTTCCTC  39660
39661  CTTCCCCTTG TGTTCCAGGG CGCACTTCAA AACGCTGACG TTCTCCTTCG TCCCTCTGGG  39720
39721  GGCGCCCGAG GGGCCCTCGC AGAAGATGAG GTGCCTTTCC AGCCAGGCTT CTCGCGTGCA  39780
39781  GGGCTTGGGA ACAGTGCATC CCCATCCTAC CAAGCAGTCC CTTCCTCTTC ATTTGCATCG  39840
39841  CGTCCGTAGT CTTATTTTTC AGTGAACTGG AGAACAGAAA ATTTTAAAAT AGATTTTTCT  39900
39901  AATATTCCAG AAGGTCAAAC ACCTTTCTGC AAAGTATCTA GCATACTAAA GGGGAAGTAA  39960
39961  TTTTACATGT CTGGAAGGTA CCATGTTTGC ATTAGAAAGG AGCTCTTCTA TTGTACTAAA  40020
40021  GTCTCCAACA AACCTCTTGA ACTCTTAAGC CTGAATTGAA AATGTGTCAA TGTTTTCAGA  40080
40081  AAATCTGAGG CCTAGAAGCT AGAGCCTCAG TTCCCTCCCC TGCCATTGT AGAAGCCTTA  40140
40141  TAGGGGATAT CTGGGGTTTT TGAAGAAAAA CACTTTCTAA GTAGGCTATT TGCTTTGCT  40200
40201  TGTTCATACA AAAGACAGGG GTTCTGAAAG TGAGGGATGC CATTGTGAGG GAAGCTATTC  40260
40261  AACATTAAGA ATGGCCAATA TCTTTTTTTT TTTTTTTGT CTTTGAGAG GGGGTCTTGC  40320
40321  TGTGTTTGTT GCCCAGGCTG GAGGGCAGTG ATGTGATCAT AGCTCACTAC AGCCTCGAAC  40380
```

Figure 1 – page 27

```
40381  TCCTGGGCAC CACTACACCC AGCTAACTTT TTTTATTTTT TGTAGACACG GTCTCACTAT  40440
40441  GTGCTCTAGG CTGGTCTCGA ACTCCTGGCC TCAAGAGATC CTTCCACTTT GACCTTCCAA  40500
40501  AGCACTGGGA TTACAGGCGT AAGGCACAGT GTCTGACCAC CAATATCTTT TTTTTTTTTT  40560
40561  TGAGACAGGA TCTCACTCTG TCACCTAGGC TGGAGTGCAG TGGCGTGATC ACTGCTCACT  40620
40621  TCAGCCTCTA CCTCCCAGGC TCAGGTGGTC CTCCCACCTC AGCCTCCCAA GTAGCTGGGA  40680
40681  CTGCAGGCAC AGACCACAAT GCCCAGTTAG TTTTTTTGTA GAGACAGGGT TTTGCTATGT  40740
40741  TGCCCACGCT AGTCTCGAAC TCCTGGGCTC AAGCAGTCTG TCCACCTCAG CCTCCCAAAG  40800
40801  TGCTGGGATT ACAGGCATGA GCCACCATGC CTGGCTGTAT CTTTATATGT GATATATAAT  40860
40861  CAGGTGGAAG AACTCAACAT AGAATTCTTT AAAAGGATGG ATTGGATATT AACATAACTA  40920
40921  CTGCTAAGTG GATCTAGATC TAACACCCAT TTTTCATTCC ATTTCTGATG ATAAAACACT  40980
40981  TAAGAAAGAC AAGACATTGG ATGTTAAGTC TGTCAGTTTA TTTTGCCTCT GCCTCTATCC  41040
41041  TAAAATTTTT TCAGAGGGGT AAATGCAAGG GACTTGTTTT AAATTGAGTA CAAGAAAGAA  41100
41101  CTATTTAGT AAAGTTGCCT GAAGATCTGC TCATCAGTGG AATAAAACAG GAAGGACAGA  41160
41161  ATTCTGATAA GCTCTTTCAT AATGACTATG TTGGAATGTC TCATCCCTCT GTCAGTTGCT  41220
41221  TTGGCTTGAG CTTCTGATTC AGAGAGCATG AAAAGGTGAG ACTAAGGAGG AAATTCTTTT  41280
41281  CACAGAGAAG CTCAGAGCCG AACCAATCCT TGGCTGTAGA GAAGGAGGAG CTTTCAGAGT  41340
41341  TTGCTGGTTC CAAGCTTTTT TCTGTTACTT AAATTTAAAG CTGGAACAGA AGGTCAAGAA  41400
41401  ACAGGAAGGA AAACCGTATC AAGATATCAA GTCATGGTAT TCTTTTTCAT TCTTACAGAA  41460
41461  AAGAATTCAC AAGAGACTTG AGGAAGCTTT TTTATTTTA TTTTGTTCTG TTTATTTATT  41520
41521  TATTTTAAGA TGGGGTCTCA CCCTGTTGCC CAGGTTGGTC TCAAACTTCT GGGCTCAAGT  41580
41581  GATCTGCCCA CTTCGGCCTC CCAAATTGCT GTGATTACAG GCATGAGCCA CTGCGCCTGG  41640
41641  CCAATTTTTT TTTTTTTTT TTTTTGCGA CAAGGTCTTT CTCTAGAGTG CAGTGGCATG  41700
41701  TTCACAGCTT AGTGCAGCCT TGACCTCCCA GCCTCAAGTG ATCCTTCCAC CTCAGCCTCC  41760
41761  TTAGTAGCTA GGACTACAGG CATCACTAGG ACTACAGGTG CCACCACCAC GTCCAGCTAA  41820
41821  TTTTCGTATT GTTTGTAGAG ACGGGGTTTC ACCGTGTTTC TCAGGCTGGT CTCAAACTCC  41880
41881  TTGGCTCAAG CAATTTAAGG AAGCTTTTCA TTAGAGTCTA AAAATACATA TTTGAATTGA  41940
41941  ATGACACAGG GTTGACACTA GTCAGAGAAT TAGGAAAATG TGATATGCGT GTTAGTTCCA  42000
```

Figure 1 – page 28

```
42001  GTGCAAACCG GAGAGCCCGT TAACCTCCCT GGGACTGGGT TTCCTCCTCT GCACAGCAAG  42060
42061  GCTCCCCTGT CCTTCCCCAT GGGAGACAAG AATCACATCA CCAGCATGTT TTCCTCTCCC  42120
42121  CTTTGGCTGC CAGGAAACTC AAGAGTCAAA TTCAAGGCTT TATTGAAGGA ACTCTGCAGG  42180
42181  ACCCAGGACG TGATATCTTG ATACTGTTTT CCTTCCTGGT TTTTGACCTT CTGTTCCAAC  42240
42241  TTGCGTTTTC CCTGATTATA GCATTTATT  ATTTTTCATA TTTAGTATGT AGTGCACATT  42300
42301  TTTACACTAC ACTTCTAATC CTTTGTGTAA TGATCATGGT AGAAATAAAT GGTGAAATGA  42360
42361  GGAGGTCCCA CTTAGATGAG TTTCAGGGGT CCTTCCAGTC CCAATTTTCC AGGATTCTTA  42420
42421  AGGGGAAAAA GTAATTTTAC ATGTCTGGAA GGTTCCAGGT TTGCACAGAA GGGAACTCTC  42480
42481  CTATCGAGAG TCCTGAGGAC TTCAGCAGAC CTCCAGGGAG GCCTGTCCAG GATGTTCTCC  42540
42541  TACGTCTGTA AAGGAGTGAG CACTTTGTGC TAGTTTAGGG AAAGACAGCT TTTCTGTTGG  42600
42601  GATTTTAGAC TTACCCTGCT TGAAATTGGT GGAAAAATAC CTGTCTGGGA TGGGGCTCAA  42660
42661  TAATCTGCAG CTGTATTAGG AAATGCAAGT AGTTTTGATG TGGGTGGTTT CAAGACATAT  42720
42721  TTGGAAAATG TGAGGGAAAT GTGTATGTGC ATTTGCTGAG CGGGGGACTG GTGAAGGATC  42780
42781  ACCGATCCAT TTATTCCTAA TGCTCATCTC AGCTTTTTAT TGTGCCGAGT ACCTTGATAA  42840
42841  GGCTTGGGTT ATTTTATGAG CGTTTATATA TAAATTGATA GTGTCCATCA GATCATGTAT  42900
42901  ATTTAGAGGC ATGCTCCTAC TTTGAGTAAA TGGAAAGCTT TAGAGATATA CACTAAATAA  42960
42961  ACATCAGTTA CTAATTAAAA ATTCCCTCCT CACTTTACCA AAGGACCCAC CATGGGTTCC  43020
43021  ATTAAATGTC TATTTATGGT TTGTTTTGAC AAAGACTTTT CCAAGAACAC CTCTGTTCTG  43080
43081  TAAAGCAGAA GAGCTGTGTA GATGTTCCAG AGTCGCTTGG TGTAAATTTG GTTCTGATTT  43140
43141  GTGCCGTGAA GCCCAATAAC AAACTGGAGG CACACATTTC AAAGCCAGTG GTAAGAGTTT  43200
43201  GAGTAGTGAT CATCTATTCC TGAACATAAA GTCTGGAGCC TTCTGGAATC CATAAAAATG  43260
43261  GAATGATTTG TTCCTTTCCC CTCTAACCAA ATTTTATTCA TACCTGGCTA TAAATAGCTT  43320
43321  CTGTTTTGAG TTTTCACTGG TCAGACCCTG CTGTTTTAGT GCCATCCTGT TAGCTTCCTT  43380
43381  GAACAAGGTA ATGCCACCTA ACATGTTTTT TCAGACTTCC AGGACAATGA TCAGGGGAC   43440
43441  TTCTCTATGC CACACTGGGA GGTGTGAAGG TGTAGGCTTT AGGGCAACCC CTCTGAGAAG  43500
43501  GGGTGGCAGG TGGAGGAGCC CATTGATCCT TTCTATCAGG GATGGATTTG CTTTCTGTGG  43560
43561  GTGTCACCTT CAGGGGCCTG TGTTCCCACT CATCACAGGA GCTCATATTT ACTCAGTGGG  43620
```

Figure 1 – page 29

```
43621  GCCAGAGTGT TCTTCATACA TGGTGATTTT ACTCCTCACC ATAACCTCCG TGGTGCGTGC  43680
43681  TAACATGACC ACCATTTTGC AGATGAGAAC ATGGAGGCTT GCAGGGGAGG TAAGTTGCCC  43740
43741  CAGGTTCCAT GCTGAATCAG AGGTCAAGCT CAGCACACAG CACAGGACCA AGTCTGCTGG  43800
43801  TTCCCAAGCT CACATCCTTA CCTACAACTC TGAATCACCC CACAGCAGAG TCAACAAGCT  43860
43861  GGCCTGGCAT GTGAAGAAGC AAGCCTGGGT GTCTCCTGGC TGCCAGTGCC ATCCCTGCCC  43920
43921  CGGGACCCTA ATCCACAGTT TGATTCTGGT CCTTTTGCCC TCTGTCCCTC ACCAGAACCC  43980
43981  TGATATTTCC AGATGAAAAC ACGAGTATAG CTTATTTCCA CAACTCACCT GGGCCCAGCA  44040
44041  ATCAAGATCT ATAGCTATAG GGAAGTATTG AGTTGATTAT GAGTTATATA GGTCAAAATG  44100
44101  AGTAGCTTGC TTGATTGAAG CAGGTAATTC GTGCCATACT TTTCTCTTTG GAAGACCTG   44160
44161  TACCAACAAT AACCTCTGCT AAACACTTTC GCTTTTTTAA ATTTGCAGGT ACTTTTTGG   44220
44221  GGCTGTCTTT GGCTGCCTGT CTGTTGAGAG TTTGTTTTCT TTACAGTCCA TCTGATTTAC  44280
44281  AGTCCCTCCG GGTTGATTTG TCTCATTTGG GAATGAGAAA TTTTATTTTA ATGCATTAAG  44340
44341  TAATAGTGTT GAGTGGCCAA CAAATGTGAA GTTTGAAAAG CTCAAATGAA AAAAAAGTG   44400
44401  TGATAGAAAC ACAGAGTTGG GGGCCGGGTG CAGTGGCTCA CACCTGTATT TCCGGCACTG  44460
44461  TGGGAGGCCA AGACAGGAGG ATCCCTTGAG CTCAGGAGTT TGAGACCCCT GGGCAACATG  44520
44521  GCAAGACCCC AAGACCCCAT CTCTACAAAA AAAATGTAAA AATCAGCCAG GGGTAATCCC  44580
44581  AGCTACTTGG GAGGCTGAGG TGGAAGGATT GCTTGAGCCC GGGAGGTTGA GGCTGCAGTG  44640
44641  AGCTGTGATC GATCTACTGG ACTCCAGCCT GAGTGACAGA GCAAGACCCT ATCTAAAAAA  44700
44701  AAAAAAAAAA AAAAAAAAG AAGAAGAAGA ACACAGGTTG GAATTTGAGG GGGCCTGTTA  44760
44761  AATAGGATGC TCTTTCCTGC CTTAGTTTTG AATTAATTGA GAAGATAAAA TAATAAGGCA  44820
44821  TGGAGATTAG AGCATCCCCT TTCTTTTTTT CTTTTTCTTT TCTTTTTTCT TTTTTTCTTT  44880
44881  TTTACTTTTT GCTCTTCTTG GCCAGGCTGG AGTGCAATGG CACAATCTTG GCTCACCACA  44940
44941  ACCTCCGCCT CGCGGGTTCA AGCAATTCTC TTGCCTCAGC TTCCCCAGTA GCTGGGGTTA  45000
45001  CAGCCACGTG CCATGATGCC CAGCTAATTT TGTATTTTCA GTAGAGACGG GGTTTCTCCA  45060
45061  TGTTGGTCAG GCTGGTCTCG AACTCCCCAC CTCAGGTAAT CCACCCGCCT CGGCCTCCCA  45120
45121  AAGTGCTGGG AATACAGGCA TGAGCCACCA GGCCGGCAG CATCCCCTTT CTTATTGATA  45180
45181  AAGCAGATCT TGGAGAATGG GAGATCCTGA GCGGGGTTCC TAATGCTAGC CTTCAACATC  45240
```

Figure 1 – page 30

```
45241  AGGCTGAGGC TCACCTTGTC TTCAAGTAAT GGGCAGTGCT GGCCTGAAGG GGAGCCTCCT  45300
45301  CTGTCCAGGG CTCAGCTTAT CCTTGGAAGG CTTAGCACAT TGAGGAGCTG CTCCAGGCTA  45360
45361  AGAGGGAGGG ACTGGGGTAC TCTGTAGAGG TTGTTCTTCC AGTTTCTTCA ATCAGATGAG  45420
45421  CCACACTGTC ACTCTAGTGT TGAAAGGAGG GAAGGGACAG AGGTGGCCAG GAGTGTGACC  45480
                                            [I5F(-148)]
45481  CTAAAAGAGG CAGAGGAGAC CTCAGAGAAA GAGAAGAAGC ATTCTCCTAA CCAGAGGGAG  45540
45541  AAGGAGAGAG GCCTCAGTTC TCCCTCTCTG GAATTAATT TGAGATTTAC ATTTAGTGTC  45600
                                                           GSTO2 Exon 6
                                                              157
45601  TATAAACATG TCAGCAGATA TATAAACTTA TTTGCTTTTG CTTTGTTTCC ATTTTAGAT  45660
                                                                     I
         158 159 160 161 162 163  164 165 166 167 168 169 170 171 172 173  174 175 176 177
45661  TCTTGAGTAT CAGAACACCA CCTTCTTTGG TGGAACCTGT ATATCCATGA TTGATTACCT  45720
        L  E   Y   Q  N  T   T  F  F  G   T  C   I  S  M   I  D  Y  L 178 179 180 181 182 183  184 185 186 187 188 189 190 191 192
45721  CCTCTGGCCC TGGTTTGAGC GGCTGGATGT GTATGGGATA CTGGAGTAAG ACATTTGACA  45780
        L  W  P   W  F  E   R  L  D  V   Y  G  I   L  D (SEQ ID NO:6)

45781  TTGTGGTGTT AAATTCCCGG AGTCACACTG AGTAACAATG GTTAAGATGG TCTGCATGCC  45840
                      [I6R115]
45841  CCCTGTAGAC ATGTTTCAGG ATGTCTGTGA AGTGAATCAG GTTTCTAAAC CGCAGTGTGT  45900
45901  GCTTCCTTGT TAAAAACATA TGTGCTTTTC CACTGCTAAC TTCAGACCCA CACTTTGCCC  45960
45961  GCATTTCTGC AGATCAGACC CCTAGCCCAG GAGCCTCCCG CAGACTTCAG AGCCTGCTGT  46020
46021  CCTCACCAGC GCCCCACAT GGCCGGTCTG AGAGCAAGTG GAGAGTCACA GTCACAGTCA  46080
46081  CAGTGCCCAA CGCCTCCACC TGGTCCTGAC GGGTCCCCAG GGACACCAT ATAACCTTAG  46140
46141  TCATGTCTCA TTGCCCGGAG GAATCTTCCC CCAGATAGGA ATAACCTTAT AAAAAAGATT  46200
46201  TGTGTAGTAA TATATGCTTG ATATTGGAAC ATACAAACAA AATGGCAGTG ACACACTATG  46260
46261  GAAGTATGGA AGTGCAGGGA CATTAAAGGA GAAGAAATAG CTGTGTAGGC TCCTGGGCAG  46320
46321  AGCAGTGCTG TGTTACTTCA AAGCTCAGTG AAGCTGGACG TGTGCGGACG TCCACCCTAA  46380
46381  TCCAAGCCAC CCTCATGGTG GGTGCTGGAC ATTTCTGGCA CTTGGAAATC CGGCCCTGCT  46440
46441  GAAGCAGAAC TGTGTCTGCA CCTTCATAAC CCGTGGGCTG GAGCCCAACC AGCCACTGTC  46500
46501  TCCTGCACTT CCGACTTCAG CTCTCTTTGT CAGGATATTT AAAACTCAAT ATCAAACATA  46560
46561  AAATTTACAA AAGGCTGTAT CCTCTGAAGA CAGAGCATGG AGTCACAGGT TAGGAAACCT  46620
```

Figure 1 – page 31

```
46621  CACTTCTAGT CCTGGATTCC CGACAACCCA TTCATATTAT CTTCAGCTTA TTGCTTTATA  46680

46681  AACCCCAGAA CTAAATATCC TGGTTGAGCT TTGAAAGAGC CCTGTCGGCT CCATGACTTC  46740

46741  AAGGTTTCAT CCTTGTTTTA TTCATTTAAA AAATGTTTTA GAATTATTT GTCTTTATTT  46800

46801  TTTTATATCT CCTAAAGTAA AATCTGAGAA TGACCCAAGA ATATTTGTTT CAGAGGGTTG  46860

46861  TCTTTTTGTT GGCAAGCAGT GAAGCACATG TAAGTTTCTC AAGCTTTAGA ATATATATAT  46920

46921  ATTAAAAAAC AAAACAAAAA AAATGAAGCA CAGACATGTT ATTTTCCCAG AGCCATCAGT  46980

46981  CCAAAGTATT TCACTGTATT ATTAGAAGCA ACAACTTCTA AACATTCAAC TATTCCAAAA  47040

47041  ATAAGATTTT CCTCCAGTAA GTTATCATTC TCACTTGATA ATAAGATAAC TAAGATAACT  47100

I6F(-97)
47101  TCCCAAATAA ACTCATTCTT CATATCTTGC AAATCTAAAA AGCAACGTGC ATCCCTTTC   47160
                                                            GSTO2 Exon 7
                     [I6F(-15)]             193 194 195 196
47161  CTGATGCCTA CCCCTGCACT GTGCTGAGGC TTCTTTCCTG TCTTGCAGCT GTGTGAGCCA  47220
                                                            C   V   S   H 197 198 199 200 201 202 203 204 205 206 207 208 209 210 211 212 213 214 215 216
47221  CAGCCAGCC CTGCGGCTCT GGATATCAGC ATGAAGTGG GACCCACAG TCTGTGCTCT  47280
        T  P   A   L   R   L   W   I   S   A   M   K   W   D   P   T   V   C   A   L 217 218 219 220 221 222 223 224 225 226 227 228 229 230 231 232 233 234 235 236
47281  TCTCATGGAT AAGAGCATTT TCCAGGGCTT CTTGAATCTC TATTTTCAGA ACAACCCTAA  47340
        L   M   D   K   S   I   F   Q   G   F   L   N   L   Y   F   Q   N   N   P   N 237 238 239 240 241 242 243                         [3'UTR R775]
47341  TGCCTTTGAC TTTGGGCTGT GCTGAGTCTC ACTGTCCACC CCTTCGCTGT CCAGAATTCC  47400
        A   F   D   F   G   L   C  (SEQ ID NO:7)

47401  CCAGCTTGTT GGGAGTCTAC GTCACGGCTT GTCTTGGGAA CCAATCCGTC TCTCTTTCTT  47460

47461  TTCTTTGAAG TTCCCAATAA AATGAAAACA GGAAATGTAT TCTTCTGATA ATCATTTGTC  47520

47521  TGACTCCTCT AGCCTGTAGC TGCTGCTACT GCTGCTTTTT TTTCCTTTTT TTTTTTGAGG  47580

47581  CAAGATCTTG CTTCGTTACT CAGGCTGGAG TGCAGTGGGA CAGTCGGCTC ACTGCAGCCT  47640

47641  TGAACTCCTG GGCTCAGTTG ATTCTCCCGC CTCAGCCTCC TGAGAAGCTA GGACTACAGG  47700

47701  TATGTGTCAC CACCCCAGC TAATTTTTAA AAAATGTTG TTGAGACAGG GTCTCACTAT  47760

47761  GTTGCTCAGG CTGGTCTCCA TCTCCTGGCC GCAAGCCATC CACCCAACTT GGTCTCCAAA  47820

[3'FR F(1218)]
47821  GTGTTGAGAT TACAGGCATG AGCCACCTGG CCTGCCTAGC CTGTAGCTTC TAACTATTTT  47880
```

Figure 1 – page 32

```
                              [3'FR R1228]
47881   CTAGAAAGTG CCTGGTGCTA ATGTCAGAGC ACATTTTGGG AGCCTGTGTG CCTCCTAACT   47940
47941   CCTTGGCCTT CAGCCTAGTT TGATCTCCAG ATTAT(T)GGTG CAGATGCTGA TGCTGAGGTT   48000
48001   CAGGGTCAAC CTATGACTGA TGCTTGTCAC TACAGAATGG CACCCTCCAA AGACCTCCCT   48060
48061   GGTGAAAGCT TAAGAAGAGG GAGAAGGAAG AAGAAAACAC TCCAAACCTA AATACCTTCC   48120
48121   ATTTGGCAAA TGAATGTCGC TGTCCACGTG GGCGAGTATG AGTGTAATTC TCCAAACTTT   48180
48181   GGCCATGGGC CTGGAGACAC CGAGGGTCTT GTGACTGGAA AGAATTCCAA AGCAGGAAAT   48240
48241   GAAACAC(C)GG TTTATCACCC AGGACTAACT ACGTCAGAAT T(T)CACTGGTG CTGTCAGGGC   48300
48301   TCAGGATGTC TCACAAAATG TTCTATAGCC GGCATCCTGC CTTAAAAAAA TACAC(A)CGCC   48360
48361   CCAAACCCAG CCACAAGCAA AGGTCATTCC GTTGGATTTG CGTCACACTC TCTTCCAATT   48420
                                                          [3'FR R1855]
48421   CATCTCAACA AATGCCTCTG GTTGCCTGTT GTGTACCAAG CCCAGGGGCA CACTGGGGAT   48480
48481   AAAGTTGAAA AAGACATTGG CTCTGTCCCT GGGAGCCCCC ATCTCTCCAC TTATCTTGGT   48540
48541   TGAGGTTTTA AACCTAGCGC TTTGGAGCTG CTTGTCTGTT GTAGGGATGC TTGTCTCTGA   48600
48601   TGTGGCCCCT CTGCCAGCTT CGCCAGGCAG TACCACCCCA CTGAAGACAG CAAAGAGCTG   48660
48661   AGGATGGCTG GTGCCAACAG GTCCCTTGGG CTGGGAGCAT CTACTGCCTG CACTATGGGA   48720
48721   GGGGGACCAA GTTTGTCCAA TGCTGTTTCA TCTCAGTGTC TGAGGATCAG CCTGTGATCA   48780
48781   TTTCAGCTTT GCTCATGCTG GATCCTTTCC CATCCTCCTA GCTGTGCTGA GACACCAGGC   48840
48841   AGCAACAGGA GCGATGTTTT GCCTTGTCTG TGCTCCCTAA GGAGCTGTCT GCCACCTCTG   48900
48901   CCTCTGAGAC AGCCCAAATC AGCCCTCCTC TCTCCCCACG TCTCAGTCTG GCCCTGCCAT   48960
48961   CTGCTGGCTC TGGGTATATT TTGACCCATG TAAATAGTTA CCAGGTGTTA CTCTGTGCCA   49020
49021   GCTGGACAGA AACAAGCCTG CTTGGTGAGG TGGCCAGAAC TTCCAGAAGA GGCAGCGCAT   49080
49081   GACAGGGCA GTCTGCCGCA CCATCTGCTC CGGATGTGGA GCCCTGTTGC CATGGCACCC   49140
49141   TAGTTAATGC TGAGTGAGGT CTGTGAATCA CCGTTTTCCT GGGATCTTTG CTCCAAGAAG   49200
49201   AGGGGAATCT TCTCCTGTGG CCTCTCATAG GACTTAGGAG ATTGATCAGC CTTTTGCCGG   49260
49261   TACAAATCCT GCATGCTAGT GAGTGCTTGT CATAAGACCA AAGTTACCAC TGATGCAACA   49320
49321   GGAAATGGCA TGCCTCTGGC TCACCAAAAT GAAGGTGTTC TCTTTTGGGG CTCCGCACAC   49380
49381   TAATTTAGAA AGCTTGAAGA ACCAGGAATT ATAGAATGGA GAAAAGCACT CATGGGGGAG   49440
```

Figure 1 – page 33

```
49441  GTTTGCAGCC TGGTGGCCTA TAGCCCAGTT TGGGATTTGA GTGCCTCTTG GCCAGGCATG  49500
49501  CTCCCTGCTG TTTACCAGGG TCCTGGTCAC CT    49560
```

Figure 2

```
1    ATGTCTGGGG ATGCGACCAG GACCCTGGGG AAAGGAAGCC AGCCCCCAGG GCCAGTCCCG    60
     M  S  G    D  A  T  R  T  L  G    K  G  S    Q  P  P  G  P  V  P

61   GAGGGGCTGA TCCGCATCTA CAGCATGAGG TTCTGCCCCT ATTCTCACAG GACCCGCCTC   120
     E  G  L    I  R  I  Y  S  M  R    F  C  P    Y  S  H  R  T  R  L

121  GTCCTCAAGG CCAAAGACAT CAGACATGAA GTGGTCAACA TTAACCTGAG AAACAAGCCT   180
     V  L  K    A  K  D  I  R  H  E    V  V  N    I  N  L  R  N  K  P

181  GAATGGTACT ATACAAAGCA CCCTTTTGGC CACATTCCTG TCCTGGAGAC CAGCCAATGT   240
     E  W  Y    Y  T  K  H  P  F  G    H  I  P    V  L  E  T  S  Q  C

241  CAACTGATCT ATGAATCTGT TATTGCTTGT GAGTACCTGG ATGATGCTTA TCCAGGAAGG   300
     Q  L  I    Y  E  S  V  I  A  C    E  Y  L    D  D  A  Y  P  G  R

301  AAGCTGTTTC CATATGACCC TTATGAACGA GCTCGCCAAA AGATGTTATT GGAGCTATTT   360
     K  L  F    P  Y  D  P  Y  E  R    A  R  Q    K  M  L  L  E  L  F

361  TGTAAGGTCC CACATTTGAC CAAGGAGTGC CTGGTAGCGT TGAGATGTGG GAGAGAATGC   420
     C  K  V    P  H  L  T  K  E  C    L  V  A    L  R  C  G  R  E  C

421  ACTAATCTGA AGGCAGCCCT GCGTCAGGAA TTCAGCAACC TGGAAGAGAT TCTTGAGTAT   480
     T  N  L    K  A  A  L  R  Q  E    F  S  N    L  E  E  I  L  E  Y

481  CAGAACACCA CCTTCTTTGG TGGAACCTGT ATATCCATGA TTGATTACCT CCTCTGGCCC   540
     Q  N  T    T  F  F  G  G  T  C    I  S  M    I  D  Y  L  L  W  P

541  TGGTTTGAGC GGCTGGATGT GTATGGGATA CTGGACTGTG TGAGCCACAC GCCAGCCCTG   600
     W  F  E    R  L  D  V  Y  G  I    L  D  C    V  S  H  T  P  A  L

601  CGGCTCTGGA TATCAGCCAT GAAGTGGGAC CCCACAGTCT GTGCTCTTCT CATGGATAAG   660
     R  L  W    I  S  A  M  K  W  D    P  T  V    C  A  L  L  M  D  K

661  AGCATTTTCC AGGGCTTCTT GAATCTCTAT TTTCAGAACA ACCCTAATGC CTTTGACTTT   720
     S  I  F    Q  G  F  L  N  L  Y    F  Q  N    N  P  N  A  F  D  F

721  GGGCTGTGCT GA   732  (SEQ ID NO:8)
     G  L  C   (SEQ ID NO:9)
```

SEQUENCE LISTING

```
<160> NUMBER OF SEQ ID NOS: 47

<210> SEQ ID NO 1
<211> LENGTH: 30639
<212> TYPE: DNA
<213> ORGANISM: Homo sapien

<400> SEQUENCE: 1
cacaaaggcc tcctgccgca aaccttcagc ggccaccaaa gccccggctg ccggcggcgg      60
accacctctg ctgccgcgcg cctaccggag ccgcttggcc ctagtgcttt ccagcggatt     120 tccccteagg tgcggagccg ggtgccgggg tcccacagcc aaccactacc ggttcctctt     180
tcgtcagcca ccggcgccgg caggacccgc gaatcccgat ctccaggagc ctgtaaggag     240
gccgcccatt ggctcagccg cactgctggg caggtacttc caaagctttg aggattggct     300
```

```
gatgctctgg gcgccggggc tagttggcgg gtaggatcac gtgcgagggg caggccccgt    360
ctaggccccg cctccttgct gctgctgccg ccgccaatcc tggtccggtt gcccgagttc    420
ccggaggtct ctcgcgggac ctctctcacc gccaccggtg ggtccgttcg gcctgcgttg    480
tattggaagg gaagaggggt ttgaggtcaa ttctgtttcc tggggttttc acgaatttcg    540
gggcccacag taggcttgcc aactttaact tttgcctaac actttacgag aaatcctatt    600
tagccttggc cactgttgca tcaaagaatt tcacatccaa caaagtgcag cctaagaata    660
aagaacaggt cttttaaaccg catacctttta attaaggtgt tcttattttt tctgatttgg    720
ctggaaacag gcagagacca ccccagataa ccagttctca gccttgcgtg ggacaccacg    780
agtcccacgt gtttacgtgt ttaaggcact ggcaagcagg ggaatttggt ttctgggaat    840
gtgctgtctt tgtgaaaact gtgaaaagtc ttccctgcta cattgaaata atcataaaat    900
aataatagct aatgttgaac acttactatg tatcagacac atgctaagca ttcaatattt    960
ctcatccagt ttctgaatga aaccttcgca aaccacataa tgtactggta ctattagcta   1020
cgaattacat ataagaacac ccgaaagttg ttgtcatttg cccaaggtca cccagctaat   1080
aaatattgaa gagattcgaa tctagcctga actcttacag taagaccgtt cgtgagatga   1140
atttatatgt gctatttttc cagtctcttt atccaacagc tctgacagag gatagtatct   1200
accttttttt ttttttttg agacggagtc tcgctgttct gcccaggccg gactgcagtg   1260
gcgcgatctc ggctcactgc aagctccgcc tcccgggttc acgccattct cctgcctcag   1320
cctcccaagt agctgggact acaggcgccc gccaccgcgc ccggctaatt ttttgtattt   1380
ttagtagaga cggggtttca ccgtgttagc caggatggtc tcgatctctt gacctcgtga   1440
tccgcccgcc tcagcctccc aaatcgctgg gattacaggc gtgagccacc gcgcccggcc   1500
tgtatctgcc tttttgacca caccattatt cgtgggattt aacaggagtt aatgagttaa   1560
taatgttcct tttccaaact cagtggtttt gattttacaa attatttgac ttttcctgat   1620
ttcaggatct tgacaatttg cctttactta ttcaaatgtt attataccaa atatttattt   1680
aaaaagtttt ttttttcttt gattcctcaa gttgtagaga gaaatagggga tagggaagca   1740 gaatcaagta gttaaaaaga tagcctcatt tgaccctgat ttcccaattg ggaatatgaa   1800 attttcctg aatataagca catttgagaa tagaacctttt tacctaacgt atctcacttt   1860
ttgaactcat tggacaataa gggaacaccc agtaatataa tctttcatat aaattaggct   1920
tctaacttat taagaggaat gtactccagt ccagtttctg ctactatcaa gagatggcgt   1980
gacaaaaaat tttgaaaagt tgccgaatgc aaaccacagt tcctcttctc aaaacaaatg   2040
catgtaaata gagtgtaagc tatttctttg gtggcattat tttcctagaa ggcttaagtc   2100
gttaatcacc catgaccgaa gatccaaaca ttttcaaagc agatccgatc atatttcagg   2160
tggctgaaaa tggatttgga gtaggtttaa tatggtctac ttacaatttg tttcatgatt   2220
gagtgggtca gtataataaa ggtataaaca tgaaataaca tagaaggaaa gtttgcaaag   2280
aggatttcaa agaagtacct gttgggtatt caaaagaaag tagggataag cttaaggtta   2340
aaatctttct agggaaagta tagtgttcag aggtaagatt aaaaaccaca ttactgaaat   2400
ggagtctgca gcattcagcc cattcaattg gcattaaact ggtaactggt gaaataagta   2460
ttgtgagttg aactttaatt ctaatatgct tggcaaagcc gaatcacagt gtgcttcatc   2520
tttgtggata caaaattgga atgcactctg ctatttaaaa tgtgttctta ctcactagcg   2580
tttgtcatta acttttgacgt atactgagct cttactatac tgacgatgcc ctggactatt   2640
```

```
tgattcgata ctcacaattc ataaagtagg tattattggt gttctcattt tgcaggtgag    2700
gaaagtgaaa tccaaaaagg ttagatagct tgcctaagtg ccaaagctgg gtctcaaaaa    2760
gtcagcccat tgggctccag ggcctgttct gagaaccttg acactagatt gtttcccttt    2820
agaggagaac agcttccatc cctgtcttct aactctacca aattaacttg gcatttcaga    2880
acttgatttc ccacatacag atacactttt catgaacatt tcccaactct cagagttagt    2940
ttcttttaaa aggtgggaat gaaaaaacaa aacttggaaa atcatcctct tctggcaaag    3000
tagaaaggtg gatccaggaa cctttttaatt tacaaatgga attcccagtt tggccattat    3060
ccagagacca tggatgggca aattaaggcc attgggctaa atccaaccaa ttgttggttt    3120
ttttatagct caatatctaa gaatgatttt ttacatttt aaagggttga aaagaaaaa     3180 ccagtcacaa cgtgatatgt gaaaattata tgaaattcac caagagtgag ccctaatata    3240
ttaactatgg atgttgggtg ataatatgtc aatgtgggtt cattgattgt aataaatgta    3300
cctctctgat tggaatattg atagtggaag agactgtgca tgtgcgggg cacagggtat    3360 atgggaaatg tgtatttct gctcaatttt gctgtgaatc taaaactttt ttttaaaaaa    3420
aggctattaa aatacatata tgcagttcaa attcagtgtg tccataaata cagccacacc    3480
catttgttta tttatcatcg atggctgttt ttacactaca agtgtagaac taaatagtgg    3540
agaccagatg gcctgaaaag cctgaaatat ttaatatatg taaaaacatt tgccaatcat    3600
tcagttcatg gcatctgata aagactaaga tactggttga gattgttgcc gctggagtca    3660
aacttccagg gttcctagtc ctccctcttt cacttactag ttgagaagtg cttaactatg    3720
ctagtctcag tttactcatc ttttaaagtg aatcaaaata gaacagttat gggactttt     3780 tttttttttt tttttttttt tttttttttt ttttttttg agacggagtc tcgctctgtc     3840
gcccaggctg gagtgcagtg gcgcagtctc ggctcacagc aagctccgcc tcccgggttc    3900
acgccgttct cctgcctcag cctcctgagt agctgggact acaggcgcct gccaccgcgc    3960
ccggctaatt tttgtgtttt tagtagagac ggggtttcac cacgttagcc aggatggcct    4020
caatctcctg acctcgtgat ccgcccgcct cggcctccca aagtgctggg attacaggca    4080
tgagccaccg cacccggccc agttattgga ctattttaag aattaactgg gtcaatacac    4140
atgaagcacc aaatatatat tagtaataat ttattttgat tttgagattt tgcaaccctc    4200
ttatggcctt ttttaggcta tggatatatt tttctcaact atcttgaaat ctgcttttt     4260 tatatgaggg atgcatgtgt atgcccagaa gtcatcttac ctaccaggag ctctaagatg    4320
acatggttgt gtttcttgct tctatttac catccaattt gtccttcttg atcagaatta    4380
gctccaaagt agtagaagtt actctgttac tttctctgtc ttcttaaatg aaaagttgtc    4440
agcgtagcaa gccgggaacc aatatgtctt ctccaacacc agatttcttg ctgacatata    4500
tgcattttat tttcagagaa catttattca aacattttg ccattccctg attcttataa     4560
aatgttaata ctttccatat tattatctaa gcttatttca catgaaatca ttgaatgaca    4620
gcaaaaaatg tagttgagtc actattctga agatttgcaa agattcttat tcactagcaa    4680
aaaatgttaa cactattatt aaccaagaag ttctggatag actggaattc caaaggccaa    4740
acagtaccca gttataagct acataattag gctctgtcat tttaataaaa gatatttaga    4800
ttcaagtatt atttgttgag cagccattac gtgctatatc ttttcctgga cttaaaatcc    4860
tttcctccta acactattac cagttttaaa ggtcaagaca acgagtcaag ctttggactt    4920
ttaaagttct tcaaccctac tagctggtca ctttgggcaa ataatttcat ttttctgaag    4980
ctgttttctg ttttgaaaag tagaaataat atgagttgcc tgactgagca attgtaggaa    5040
```

```
tcaaggtaat ctatggaaat aatttagtca gtatgagtga gacacagaaa atatttttct    5100
ttccttcatg atctgttaat cctacaaaat gcatttacaa gcaattccca catcagctca    5160
attctggaaa atttaaggaa ttatttttt acctgctgaa attcaggatc tcagcttatc     5220
agcatcagag ccaaagccac gtctattatc tcacgtaaac agaaaagctg tgcaagtcgc    5280
ccctatatgg ctgggctgtt ggcaatgtat ccttggcaac tagtaagagt gttctcaaaa    5340
atttatgctg gggaacgggg gaagctcaca aattgttctt tgcctccagg tatcttaatt    5400
ttattcattg ccagttttc agagcttggg taaaatctca caagtagggc caggactggg     5460
atgaggcaac tgaggtgtct agggtgcaaa atgtgagttg tctagacacc aaagttgtct    5520
aggtgtctag gaggcactca ctctctgggg tatgtgagat ttcaacacca atgacttttt    5580
cttttcctagt tgctgtatca tgagaatgtt tggccttatt atttttttaaa gctgtactta   5640
cttaccaaag agtggccagt ttagtgatgc aagagattca gaatgggaaa aaaaaagtca    5700
gctttacccct agtcagttt gattaaactc ctttgaaatc catgttggag tttaaatgcc     5760
cattcttgag ggattcttga tgtagaggag gcccctccaa agctttaagc acatgtccag    5820
agcaaggggg agcttttctg gtgttatttt gtcttgtttt gttttttgcc agctcctact    5880
ctcgggcttc caaatctggg gcgatgtctc cccaggttaa attaccctag ctcctgctcc    5940
agatcgcttc cccgtgcccc gccagagccc agtagttcaa aaattaaatt tggggcaagg    6000
ggtgcgcgcc agagcgcagc tgtttctgga gcctgcggca gcggtggcga gccacagggc    6060
ggcgaccgtg agctccggga gctgcgcaaa ccacctggag accatgtctg gggatgcgac    6120
caggaccctg ggaaaggtg agtgctctcc atggggtccg cgagctgggg gcgccgcgtg     6180
acagaaaatg ttggcttcgg cggagctgcc tggccttggc ctgcagaccg gcggggcagg    6240
aagggacttg gagggctctc ctgaagaaaa gccacatgca gcactgccct ctctgggact    6300
tgggagttgg agctcccaca gccatcttgg gatctgggca agtgagcgag ctccttcctc    6360
accgggctga ctagcctctc ctttccctgt cccctccat cgctgctctg caggaagcca    6420
gcccccaggg ccagtcccgg aggggctgat ccgcatctac agcatgaggt ctgcccccta    6480
ttctcacagg acccgcctcg tcctcaaggc caaagacatc aggtgagaag cgggaaccca    6540
gagcccccga gcaaacccag cgcctcacag gagcccggga atgtttaaca tctggggcgc    6600
cctgctcagc ttttacaagg ggctccctgt cccttttttc ggaggcaaag tcaacaaata    6660
gcaaagggcg agcttttttt tagcgggccc tactgaaatg cggagccctt ttccgagtca    6720
cgcctatgca tgaaacttct agcccagcgc agagtaatgt gaatgatggg gctggtgaac    6780
tggttccctc ccagaatgtt taagggcaca gccaacacta ctgaggcctt acctgactgc    6840
tccacagagg tagttccccc accacacccc aggcatctta ggtcactgtt cctttctttt   6900
attgaactta ctgcatccag catttttctta tttgttcatc catctcccct ccccagtccc    6960
cttcacccat gtgcgttctc gagggtagga actctgtctc ttttattcat gagctaggag    7020
agagcctgtc acatagtgga tgctcaaaaa acatctgtta aatgaatgaa caaatctttc    7080
caaacaatga aatagaagga attgctatca agaggtgtct ggaagttttc aagacacctt    7140
gaaaacttga gaaatgggta cagatgcttc caaaaggaag tttgcaaaac cagctcctgc    7200
aggtctggat ttggagggca gagcagcttt gctgggatgt ggactgcata atgcagctgg    7260
cctccaagct agagtgttga gaatatgtca ctccaggctc ccgactcttg tctcggagag    7320
tccatcacaa gggggtgact tcagagtttc agactcatgt cagagagata caaagactaa    7380
```

```
tacagagatg tttaaaataa aattatgtaa atctgccttg ttgagtatat agggcctgta    7440
tttccacatt cttccctttt gctcaaatta agctgacctt aaggttacct gttttttgag    7500
gaaaataaca acaactggat gttttgccca tttggtgata aattatcagc ttaggagctg    7560
atgtatttcc ttaggtcagc gtttctcaaa cttggcactg ttgacagttt aggccagata    7620
attctttgtt ggagaggtgg gatagaagct gtcctgtcca tcactggatg tttagcagta    7680
tccttggtct ctacccattc aatgacagta gagtccccct tccctatgca ctaccttcag    7740
ttgtgacaac aaaaccatgt ctccagacat agtgatatgt cccttgggaa ggaggccaaa    7800
aatcacttct agtcgagacc cattgcttta ggttgagacc cactgcttta ggtcttgcta    7860
tgtggcctat gctggtctcg aaatcttggg ctcaagcaat cctcccaccc tggcctctca    7920
aagtgctgag attacaggtg tgagccacct catccagcct ctgctgtagg tttaagacaa    7980
tctcctagac taagcaatga acgttcccat ttgtttcctt tcatgttttt aaacatacgt    8040
tcatgcttct ggtaactata tagttatcta aataataatt gtattatgtg aacattaaat    8100
aataatagta ttatttgaac atctaataat tagaagaaga attaaaaaag ttattgcatg    8160
cttatgtgcc aggcactgtc ctaaacactt tatacatatc cccaccacag taccaagaga    8220
tgggtgtaat tattagcccc attttataat taaggacact gagcacagag aggttaggaa    8280
ttcggttaag gtcccaagct agaccgttta ttctgatgcc aaaactcata ctcttaattg    8340
ttaacattta ccatattctg ttgtgacctg ttaataccag atttgtattt tcaagctgta    8400
gaatgtacta aactctctaa tgccatggtt aagtgtgtga gctctgagtc tgtctgcctg    8460
gctgtgatct tggctctact actttttttt tttttagat ggagtttctt gcccaggctg    8520
gagtacagtg gtgtaatctc agctcactgc aacctccacc tcccgggttc aagcaattct    8580
cctgcctcag tctcccaagt agctggggtt acaggcgccc gccaccatgc ctggctactt    8640
ttttgtattt tttagtagag atggggtttt gccatgttgg ccaggcaggt cttgaattcc    8700
tgacctcaga tgatctgccc gccccagcct cccaaagtgc tgggattaca ggtgtgaggc    8760
accgcgcccg gccagctcta ctacttctta gtgggtggta ttgggtgtga gattcaaccc    8820
ccttgagtct tctttcctat gaggtgagcc tacttcaggg ggaattatga ggaacaactg    8880
agataaggca tggaaaacat ccgacacatc ttactgcagg aaggaagatg atgatgttat    8940
gtatttata caaaacttaa accttaaaac actaattgca aatttaact tttaaactga    9000
ttgcttctgc tttcaagaag agtgcctgcc tgcagatgcc tctcattttt gttctgtctt    9060
gttttccttt tgcttttaa gacatgaagt ggtcaacatt aacctgagaa acaagcctga    9120
atggtactat acaaagcacc cttttggcca cattcctgtc ctggagacca gccaatgtca    9180
actgatctat gaatctgtta ttgcttgtga gtacctggat gatgcttatc caggaaggaa    9240
gctgtttcca tatgaccctt atgaacgagc tcgccaaaag atgttattgg agctattttg    9300
taaggtatat tcaatttaaa aagtcactca cactgtattt tactttgcat gtctttccca    9360
aacctcaacc cattttaaag ccaaatcatt ggtgaaactg ttttgttttg ataccatgtg    9420
atcctcagga gattagctag catggaatta gggtagagca tggccactga tattaaaggc    9480
ttaactgcta ggcgcttctc catttcaact ggcaggctca ggaggtatgg ttatgacatg    9540
gcaatgaccg tgtaacttga agcaggaata ctgaaagaac tgaaaactgg tgatccttaa    9600
agggagtatt tctccagctt caggtaaaaa gtaatggagt gcgaagatta tgcatagaag    9660
gtgatgcttt ttattatttt tttttttgag acggagtctc gctctgtcac ccaggctgga    9720
gtgcagtggc accatctcgg ctcactgcaa cctctgccac ctgggtttaa gcaattttcc    9780
```

```
tgcctcagcc tcctgagtag ctgggattac aggcgcatgc caccacaccc cctaattgtt    9840 gtattttag tagagatggg gtttcaccat attggccagg ctggtcttga actcctgacc     9900
tcaagtgatc tgcctgcctc ggcctcccaa agtgctagga ttacagacgt gagccactgt    9960
gcctggccag tgatgctctt tagaagcata agagtgcctg ctgtccagga aatgtgaaga   10020
atagataaat ggtggcagct ttgataatga aagaaaaaag aatggagaaa ttttaagatg   10080
gtgtctttga aaaggaattt ttaaaaacct caatgatatt aacagctgac atatatcgaa   10140
cacttatgat gtgccaggca ctgtcctagt tactttgtag gagctaactc atttaatcca   10200
actgcccttt gaagtgggta ctgctatcgt atccattttt cagatgagaa cactgaggct   10260
tagagaggtt gagtgtccca cctaagaatg tatagcatgg aagcagctga tcaagtaagg   10320
agcactggag aaaccctcct aaagcaccct gctttcccag ggtactataa aagtagatt   10380 cctactgaga accggaacca cagagaaaac ctagtgcctc tcacagggag ctgggggggtc   10440 tgatgtgggt gttgccctgt taggctggag ttataaagct tcgctgcctt ttcaggcaga    10500
acaggaactg gaagtttcca cagacttctc cactgagaac ctgtgtcctc tgattaggtc    10560
ccacatttga ccaaggagtg cctggtagcg ttgagatgtg ggagagaatg cactaatctg    10620
aaggcagccc tgcgtcagga attcagcaac ctggaagagg tacaaaaagg ggtccctctc    10680
ctggtcagct acagtggagg aagctaggca gggtcgctaa cctggtcact ctaacaccag    10740
ctttcacagg cttattcttt ctgcctttga taagtcagac ttctgatcat ctgattgcat    10800
gtttgccctc ctctaacctg gtctagaatt attctggaaa atctgatgag gagttgggga    10860
ggacatgcca tgaattgctt cctttcccag agtcaccca tctccctgag tagctctgca    10920
tggcttctgt agcttctgcc aatgaggtca aggtctgtaa aggttagggg ttgtgtttgg    10980
ctgctgaagt ctaactactg taaattcatg ttgtaagggt ttactctctc acataacatt    11040 cttctcacg tattataagg gtttattctc acacatacgg tggctcacac ctgtgatccc    11100
agcacttggg gaggctgaag caggaggatc acttgagcct agaagtttaa gaccagccta    11160
ggcaacatag caagacccct cctctacaaa aataatttta aaaattagcc aggcataacg    11220 atgtataacct gtagtcccag ctacttagga ggctgaggca ggaggattgc ttgagtctgg    11280
gaggtcaaag ctgcagtgag ccatgattgc accactgcac tctagcctgg gtgacagagt    11340
aagtaggact gacaaaaaaa aaaaaaaaa aaaaaaaag ccagaggtag gcagttcagg    11400
cctatcttga tggcttcttc atgacattat caggaactga agcttttttct ctttatgggc    11460 tctgtcatcc ttagcacaac ttagtacaag ggtatcatcc tcaaaataac aagatagctg    11520
ctgtcactgc agccatcaca tccaagttcc aggctctgaa aaggagaata taagaaaaa    11580 aatggcaaat ggtcataccc ctttaagggg ctttaaatcc taccagaaat tctactcaat    11640
ggctatttac atttcgttgg ccagaactta gttgtggggt cataactatc ttagagaaag    11700
ctgggaaata cagtctttta gctgggatac cctgaataaa atcagaggtc tgtaattaag    11760
gaagaagggg gaaatgggtg cggtggcagg aatactcttt gccagtagat gcttcattaa    11820
cctggcagta atggagctac ttatcctgta cttctagaat aatcaggaag gcagttcttt    11880
tacttccttt attttgctc cagaaactga caaattcacc ttatgggtgg gtggttcctc    11940
tattggcagc cagagaatac aatttttttc cccttaaggg aagactggtt attaatactc    12000
ttccatttga cctttatcaa gtggaaacag attaaatgta ttgatatttc cagttgccta    12060
tctcaaattt gtacgattaa gtatttatgg atgacgaatg gtcatgtgta ggaaatgtca    12120
```

```
accttttgtc ctgaggtcac caactgtggc cttgactcca aggaggccat atgatgtggt   12180
ggaaagaatc ttggatctta ggcttggctt tactgaattc cagaaccttg ggcaatgttc   12240
tgtacctctc tgggccttgg ttttcccatg tgtaaaatga gggattattt tgaaatgtgt   12300
gttcctcaga gcctctgggt tctgcagggg actgcccagt gagtggaggc ctggtagatt   12360
gttctagaca ctgctttact taggtcagca ctgccttcaa ccaccatgtt caacctgaca   12420
tctaagaaga tggcatttgg ggagagagga gagctgctgc tttaaaaaag aagttcgaaa   12480
atcttgtgaa tagagaattt atagtctatt ttaaagatca gctgaatgga ccccatcatg   12540
cctggttacc ttctcacaga taaacaaata ctggaccagg gaaggagct gggaaaaaaa   12600 aaactctttg aattcaacga tacagtaatt gaaacatttt catcagtttc ccttctacct   12660
ccatttggat gatggatgaa cttttttaaat tacagattgc tagatgaaag tatagggtta   12720
tgatggagat acagttcttc ttcagtcggg ggtcttttcc agggcaaatg aaccagtatt   12780
ttgtgccatg aatcgtgctg cagatacttg catacatcat ctcattcaat ctttccaaca   12840
accttctcag gtacaaatgg tactagtcct gttttgcaaa ttggagtggc ctctctgtaa   12900
aggctcagaa ctaggtacta ggaataaaaa gaaattaaag accctcgagg ggctcaaagc   12960
ctggacaggg agataggctg ttaagcccat ttaaaacctg ggtgtgttga gtgctaggct   13020
ggagacatgc atacaagaag gctggtctgt ggggtagta aatgcctctg ttgactctta   13080
ggatgaatta gaggcacaag ggtgagagcc tggtgtgttc ggcaaacaat aatcagtgag   13140
gggttgacag cgagggagtg attggtaaga ggtgaatgtg gagggtggac cagagtcaga   13200
tgctaaaagg cctttccac tgtgcccagg gatttgcact ttatttcaga gttgatggtg   13260
agtaattgaa gcctgtcaag caggagagtg gtgtactcct tcatgctttt aaaagtattc   13320
agtccatcac ttgaacccag gaggggagg ttgctgtgag ccaagactgc gccactgcac   13380
tccagcctgg gcaacagagt gagactctgt ttcaaaaaaa aaaaaaaaaa agaaaagaaa   13440
agaaaaagta ttcagcccag ctgagcacag tggctcatgt ctgtaatccc agcactttga   13500
gaagccaaga cggtaggatc gcttgagccc agaagtttga gaacacctg gtcaacatgg   13560 caaacctcca tctctttaaa aaatacaaaa tgttagcttg gcatggtggc ttatgcctgt   13620
agtcctaggt acttgggagg ctgagatgag aggatcactg gagcctagga ggttgaagct   13680
gcagtgagct ataattgcac cactgcactc cagcctggac aacacagtga aaccctatct   13740
caaaaaaaaa aaaaagaag aagaagaagt tcagcccagc aagaatgtag aggatggatt   13800
agagtgtcca agaggaggga ctgggaaggg acaaagagga ccccactaac gagggttgga   13860
gagggaggtt taattagaga gattttgagg aactaagatg agatgaaatc tgaggaagga   13920
gtaggagtta tggaggatgg tttccaagtt tgtggccggt aaatgtgatg cttttcacta   13980
agagtttgag ggaagacaca ttttgtcaaa tttgtggtgt tgatgggata ttcatatgcg   14040
ggcagagctt agaagaacaa tgtatggtct ctactgacc tttggaatgg ttttatgggc   14100
taggagcttt caccagagag tttaggaatg tcattagtgg ggtggtgata aatgtttaag   14160
aatcaatttt ctcttaaaag agaagaaaa agaaaaagca cggatttata gcatttgctg   14220
atttgggtgg tgtaaacact tccgtcaagg ttaattttga gctaccaatg tgctatttct   14280
aaactcaaga gctggcaaaa gatgtgggca gctccagcat gtcactgaat aagaaatttc   14340
actttatctt caataactga gccccaggaa cactgttgtt aaccagcctc tatataggta   14400
gctttcacta accagcctcg gtgtaggtag ctttcactga tgctatttaa ggaccactga   14460
gtactccaca ttgtcctaac aggtttgaat gtggttttgt cccatagaat gttagcaaga   14520
```

-continued

```
attgtagcta tggctgggcg tggtggctca cacttgtaat ccaggcactt tgggaggcca    14580
aggagggagg atcacctgag gccaggagtt caagaccagc ctgggcaaca cagtgagact    14640
atgtttctac taaaaattaa aacatgaact ggtcatggca gtgcgggtct gtagtcccac    14700
cttctctgga ggctgaggcg ggagcatctt ttgaacccag gagtttgagc ttgcaatgag    14760
ctatgatcgt gccactgtac tccagcctgg gtgacacagc aagactctgt ctcaaaaaca    14820
aataaacaaa gaattataac tacaatgtag gaaatattga aatctgaaaa catgaccaat    14880
gtacttgaat tatgcgatct gttcctttaa atgccaaaat attattcca ggagattcta    14940
gtgaaattga aatttatcag aataattcta atggagagga tccctgatt tatgtaactc    15000
tttcacatgg ttttgcacaa tcaggatttt ttgtgagcta aaaatatatt aaatactcat    15060
tgtctttctg agtgataagc aagccaagat tcatgcata atcttctgct atgttatcct    15120
gaaacagaag gctcagttaa ccttttgtgg ccttaaactc tgacactttc ttcttttgaa    15180
ataactgcct tgtctaactt tttaagtttt ttttttttt tggcttgttt tttgtttgc     15240
ttgttagttt tttaaatcta gtttcaggtg ggttcagtgg ctcatgcctg caatcccagc    15300
actttgggag gccgaggcgg gcagatcatt ttaatccagg agtccgagac aagactgtac    15360
aacatggcaa aaccttatct ctacaaaaaa tacaaaaatt agttggatgt ggtgatgcat    15420
acccgtggtc cctgctactt gggaggctga ggtgggagga tcacttgagt ccaggaggtc    15480
aaggctgcag tgagctatga tcatgccact gtactccagc ctgggtgaca gagtgagact    15540
ttgtctccaa gaaaaaaaaa attaagttcc atcaaaatca aagatttatt gtgcttgtta    15600
tataaccaca ttttctcta atatctttta caattctttg agatatatta ctgccactt    15660
tattatcaaa ctagcagcct gctcactggc tttcctgttc tgaacattgg catgagtttt    15720
aaaactatga cacttgtctt gtcttgctgc actttatgtc ttcaagcaga ttttctagcc    15780
cttactgaat cattactcta agcagcacac attttttagt tttattcttt ttcaggtatt    15840
gactttccca tttcagaatg ggacttgagc caggcttcat ttgatctttg tggatttgaa    15900
tgtggcagga cctcttggtg tcactttta tctgtgcctt ccaaaaatat tttcattatg    15960
gaagtagtca aatcaagtcc aagtgcagtg aaaggtggat ttggtcagat ttccttgagg    16020
ctttggagtt ttgcttttaa tctagaaagt gttcgtggct tctgaattgg ttctgcactc    16080
tgactattgc ttggtccttt cttcgtcatc atcagagctc cataaaagag agcggggagg    16140
ggataacata aataatgctg aaatagccct gagggatgag acatggccca gcaactgaag    16200
ccttcgtctg cccgtggcca cagggcactt tatggttttg cttcttgtca ttcaaccacc    16260
tgccttgggg tgcttcactt tgcatttcca cgcagagttt cccgcattgc caaacttgat    16320
catgtgcctt atgtgtagca gttttgcatga ggtggaattt gcataaatta tgtgtgcatc    16380
acccaggagc atctgtagtt aaatacttta ttgattctaa attttgccca taatcttaat    16440
ttttaatta tttattttc ttttcctctt ttagagattg gggtctctct ctattgccca    16500
ggttggagtg cagtggcaca gtcatggctc actgtcgtct tgagctcctg ggctcaagca    16560
gtacttccac ctcagcctcc cgagtagctg ggattacagg ctgaagccac cgagcctgcc    16620
tccgttatct taattattat tataattatt ttttgagtc agggtcgcac tctgtcaccc    16680
acattggagt gcagtgacac aatcacggct cactgcagcc tcagcctcct gggctcaagt    16740
gattctctca cctcaacctc ctgagtagct gggaccacag gttcaggcca ccatgcccaa    16800
ctgttttgtt tttgtttta tttgtttaa ttttttgtgg agacgaggtc tcactatgtt    16860
```

```
gctcaggctg gtcttgaact cctaggctca agtgattctc ccacttcagc ctcccaaagt  16920
gctatgatta caggcatgag ccactgcacc tggtaatctt aattttaaa ctgttctttc   16980
ttctcatcaa aaagacatt tattcaagtt agattatatt gtcttggttt agttttgctt   17040
ttgctctttc ttaatttta ttaatttcca gtgatgaaat tatttatata ttgtttaatt   17100
gtttctcctt tgatatcacc aggataggaa gaaaagaaag tttatacctg gttaattcgt   17160
cactgaaaac aattttctgt atcctttat atatagtaga ctacaagcta aatttttat   17220
catctaagtt aacatgtcta taaactaaat tcattattac tagctatttt taataagtta  17280
ttgagatata attcatatgc cacaaaattc acccttttcc agtgtacaat tcactggctt   17340
ttagtatatt aagtgagttg tgcaactatc accagtattt aatttcagag cgttttttt   17400
atcatccccc agaaaaactg ctcacttgta agctgtcatt ttccatttct tctcaatccc   17460
tgtggctgta cgcagccact gatctgcttt ctgtctctat ggattgactt attctagaca   17520
cttcatataa gtggaatcat acaacatgta gcatttcatg agctattttc acataccata   17580
atgttcttaa ggttcatcct tcattctttt ttatggctaa ataatattcc atgtgtgaat   17640
acgcacattt tgtttatcca catctgggaa ggttccactc ttggaactaa tatggataat   17700
gttgctgtga acaccatgca ggttttgca tgaatatacg ttgttatttc tcttggattt    17760
gctagctgat ttagcatgtt tactaacatg ccatttagt tgtaaccacc attcttcac     17820
acttgggaac tgattatccc tgactcagga tgcctcgtta agtgtattag tgctgttgct   17880
agttgggtta cttccttcat catccaattc tgacagctgc taatatttgc tgtacttctt   17940
tcaatagctt tctgatatac cctttcccat cacataaata atagaataat aattattctt   18000
attatttaaa aattaatttt actcttctcc aattataaag taatacttgt tcattagaga   18060
gaatttggaa aatacaggaa aacatagaaa ctaaggaaaa aaaattataa tcccactacc   18120
cagaaacaac cactgttatt atcttgggga cttttttgtt tttgttttct gtcctttct    18180
gctatgtata ttttatgtag ttgaaacttg gttactatta tgatgtaaat attccccaca   18240
ccccctgcca ttttattttg agacagggtt ttactctgtt gcccaggctg gaatgcaggg   18300
tgcaatcacg cctcactgca accttgaact cctgagctca agggagcctc ccaactcagt   18360
ctcctgagta gctgggacta caggcatgtg ccaccatgcc tagctagttt tcttttaac    18420
ttttgtagag acagggtctc cctctgttgc ccaggctggt gtcgaactcc tgggctcaag   18480
tgacccactt gtctttgcct tccaaaatgt tggcattaca ggtgtgagcc accacctg     18540
gccaattttt ataaactctg taaatgctta tttacatata taagagtgtt ccttagcaa    18600
gcagcattat ttgtgatgat gacaaattag gaaacaatat tcattagatg gtgagtggtt   18660
aagtaaatca tgtctgtctt gtggaattct gtggaacggc tgaaaatgaa tgaggtaaat   18720
ctatgtgtac tgacattaaa agattgccta gaaatattaa atgaatcaca cagtaataca   18780
ggtggtatga tccattttta gcagaagaaa acaaaactga accatgcagg tgtgcacata   18840
catgtaaata agtggctaga aaagtatcta gagagaaaca catccacctc ctagtaatgt   18900
ctcacactgg gaagggggct gattagaatt agggtgggta agaaaagtgg ttaagggcag   18960
ggaccgggag ggaagatttt gtcttttaca ttattttctg tgtttgattt ttttttttaat  19020
gatgggaatg tatttctgta ttaaatatgt aagttttaaa agtagaaaaa aacacttttt   19080
tttttttttt tttgggacgg agtctcgctc tgtcgcccag gctggagtgt agtggtgcta   19140
tctcggctca ctgcgagctc cacctcccag gttcatgcca ttctcctgcc tcagcctccc   19200
aagtagctgg gactacaggc acccgccacc acgcccggct aatttctttt tgtattttta   19260
```

```
gtagagatgg ggtttcactg tgttagccag gatggtctcc atctcctgac cttgtgatcc     19320
atctgcctcg gcctcccaaa gtgctgggat tacaggcgtg agccacctca cccggccgaa     19380 aacacttttta atgtctgcat actttgccat gtttataaac cataaagtta tttatccagc     19440
acactaatta ggagtgttta gatggttttc agtcctttac tgttttgaat ggtgctgcag     19500
ggaacatcag cttctttgca taaaaagcat tttctctatt ttagaatatg ttcttaagct     19560
ggactctcag gaatggaatt accagatcaa agggtataat gagcacattg gaggcttgga     19620
ctgtatttca ctaaattgct tcccaaaaga cttgtgttgt ttgcccctca ccagcagtat     19680
gtgaaaatgc tctttgccct atatccttt cactggtggg agacttcatt caaaaagata     19740
tttgtttgtt gaataatatt tgctgtggag atacactgta gttcctcatt gttgacttaa     19800
tgcatatttc tttgatggcc agggaagtgg aaggttttcc cggaagtatg tcatcccttg     19860
ctcctggtct tgcaaaattt gtctgttcag ttcaggggct ttgcctatct ggccatcaga     19920
gtcttactaa ttttctttgt tgatttgtaa aagttccttt taaagcgttc cttgtataga     19980
aaagatattt gactggtttt aaaacacatt tttgtttcct tttgacttt aatttggctt     20040 atatatttt gcatatggaa gtacagcatt tgaaagtatt gtgctataag gctttcctta     20100
tatgtgctat gatttcctcc actgttttat gtgtaggaag tcctctcccc acttcagaga     20160
cttgataaat attcatttat atttcatct accaccaatc actttacaga catttgactg     20220
gtcaagcatt accctcctag cttttcccccc cacactatct tacaaatata ttgtgatttg     20280
ttttagtttt tgtttttttgt tttgagaca gggtctcact ctgtcactca ggctggagtg     20340
cagtggcatg atcatggctc actgcagcct cgacctctca ggctcaggtg atcttcctac     20400
cttagcctcc tgagtgtcta ggactacagg caccactatg cctggctaat tttgtgtatt     20460
ttttgtagag atgggatttt gccatgttgc ccagactggt ctcgaacttc tgggctgaag     20520
cgatccttcc accttggtct cccaaagtac taggataaaa ggtgtgagcc accacaccca     20580
gccctacaaa tatattttga agatacgaat taagctcatt aaaaggatgc cagcatagaa     20640
ttttcagagt ggtcctttaa tcccaaaatt ttgacagttg tattctgcac cttcatggag     20700
aatctaggtc ataactgatg ggcagcagga ggggcatgtt ctgctgcagg tcctccctct     20760
aaggctcctt cccagaggag aaaatggtct taaatatgcc ctaggtttgt tccacaccct     20820
aggtttgttt tacagggaac tgggtcatca catggttagc tcagcctcag ctatatcatt     20880
ttagcaggga tctgagattt gaaatcttaa gaacctccat ttatcttta tgagctcaaa     20940 acatttctgc cctccaaaag acttgaatag acatttctca aaagaagaca cacaaatggc     21000
aaacagacat atgaaaaggt gctcagcatc attgatcatc agagaaaggc aaatcaaaac     21060
tacaatgaga tatcatctca ccccagttaa aatggcttac atccaaaaga caggcaataa     21120
cgaatactgg tgaggatgtg gagaaaaggg aaccctcgtt cactggggcg ggaatgttaa     21180
ttagtataac cattgtggag aacagtttgg aggttcctca aaacactaaa aattgagcta     21240
ccatatgatc cagcaatccc actgctgggt acacacccaa agaaaggaa atcagtatat     21300 caaagagata cctggaccct tatgtttgtt gcagcactgt ttacaatagc taagatttga     21360
aagcaaccta agtgtgcacg aataaggaat ggataaagaa aatgtgatac aggccgggtg     21420
tggtggctca ctcctgtaat cccagtactt tgggaggcca aggctagcgg atcacttaag     21480
gtcaggagtt cgagaccagc ctggccaaca tggtgaaacc ctgtctctac tgaaaataca     21540
aaaattagct ggcatggtag tgcatgcctg gaatcccagc tactcaggag gctgaggcag     21600
```

-continued

```
gagaattgct tgaatctggg aggcagaggt tgcagtgagc tgagatcaca ccactgcact   21660
ccaacttggg tgacagagtc acactctgtc tcaaaaaaaa aaagaaaaa agaaaatata    21720
gtacatatac acaatggagt actatttggc catgaaaaga atgagatcct gtcatttgca   21780
gcaacatgga tggaactgga gatcatgtta agtgaaacaa gccaggcaca gaaagacaaa   21840
catcacatgt tctcacttat ttgtggaatc taaaaatcaa aacaattgaa ctcatgaaca   21900
cagagagtag aaggatagtt tgcagaggct aggaagggta gtgtgagctg gcagggaggt   21960
ggggatggtt aatgggtaca aaaaacagaa agaatgaata agacctacta tctgatagca   22020
ccacatggtg actatagtaa ataataactt aattgcacat ttaaaaataa cttaaacagt   22080
gtaattgggt tgtttgtaat tgaaaggata aatgcttggg ggagtggata ccccattctc   22140
catgatgtgc ttattgcata ctgcatgcct ggaccaaaat atgtacccca taaatatata   22200
cacctactat gtgcccacga aaaataaaat taataaaaga tttctgccct ggagttgagt   22260
actttttccac tgcttctgga aaagggccag tattgctgat gtactggcat gttgctttgt   22320
gtcttttttag gggccacaga gggtggagga tggcttctgc ttttttgggg ggcagagagt   22380
aggggatgac ctctgcattt tcagaacgat tttcatgagg aaaaacttc ttcctcctcc    22440
agcaagtaca gcagccccca ctgggagcca ccacactgtt tcgagattgg gggcttggga   22500
tttcttggca atggtgtaga ggatggtgaa ggtgagctgg cctcttcaag gtttgaagct   22560
caattattga ggctgaacca aagagttgaa gactggagct ctctcgaatg cctggtttgg   22620
agatgtctgg gattcgcttc tcctaatgat cttgcttctc tcgcgaaaac tgcagatttc   22680
ttcatcctcc ggttgaacgt tcttggggag ccgcggccga cgcgcctcgc actgatggcc   22740
accagggggga gccccgcgcg cttcctcctt cccttgtgt tccagggcgc acttcaaaac    22800
gctgacgttc tccttcgtcc ctctggggggc gcccgagggg ccctcgcaga agatgaggtg   22860
cctttccagc caggcttctc gcgtgcaggg cttgggaaca gtgcatcccc atcctaccaa   22920
gcagtccctt cctcttcatt tgcatcgcgt ccgtagtctt attttttcagt gaactggaga   22980
acagaaaatt ttaaaataga ttttttctaat attccagaag gtcaaacacc tttctgcaaa   23040
gtatctagca tactaaaggg gaagtaattt tacatgtctg gaaggtacca tgtttgcatt   23100
agaaaggagc tcttctattg tactaaagtc tccaacaaac ctcttgaact cttaagcctg   23160
aattgaaaat gtgtcaatgt tttcagaaaa tctgaggcct agaagctaga gcctcagttc   23220
cctcccctgc catttgtaga agccttatag gggatatctg gggttttga agaaaaacac    23280
tttctaagta ggctattttg ctttgcttgt tcatacaaaa gacaggggtt ctgaaagtga   23340
gggatgccat tgtgagggaa gctattcaac attaagaatg gccaatatct tttttttttt   23400
tttttgtctt ttgagagggg gtcttgctgt gtttgttgcc caggctggag ggcagtgatg   23460
tgatcatagc tcactacagc ctcgaactcc tgggcaccac tacacccagc taactttttt   23520
tatttttgt agacacggtc tcactatgtg ctctaggctg gtctcgaact cctgccctca   23580
agagatcctt ccactttgac cttccaaagc actgggatta caggcgtaag gcacagtgtc   23640
tgaccaccaa tatctttttt tttttttga gacaggatct cactctgtca cctaggctgg   23700
agtgcagtgg cgtgatcact gctcacttca gcctctacct cccaggctca ggtggtcctc   23760
ccacctcagc ctcccaagta gctgggactg caggcacaga ccacaatgcc cagttagttt   23820
ttttgtagag acagggtttt gctatgttgc ccacgctagt ctcgaactcc tgggctcaag   23880
cagtctgtcc acctcagcct cccaaagtgc tgggattaca ggcatgagcc accatgcctg   23940
gctgtatctt tatatgtgat atataatcag gtggaagaac tcaacataga attctttaaa   24000
```

```
aggatggatt ggatattaac ataactactg ctaagtggat ctagatctaa cacccatttt   24060
tcattccatt tctgatgata aaacacttaa gaaagacaag acattggatg ttaagtctgt   24120
cagtttattt tgcctctgcc tctatcctaa aattttttca gaggggtaaa tgcaagggac   24180 ttgtttaaa ttgagtacaa gaaagaacta ttttagtaaa gttgcctgaa gatctgctca   24240
tcagtggaat aaaacaggaa ggacagaatt ctgataagct ctttcataat gactatgttg   24300
gaatgtctca tccctctgtc agttgctttg gcttgagctt ctgattcaga gagcatgaaa   24360
aggtgagact aaggaggaaa ttcttttcac agagaagctc agagccgaac caatccttgg   24420
ctgtagagaa ggaggagctt tcagagtttg ctggttccaa gctttttct gttacttaaa   24480 tttaaagctg gaacagaagg tcaagaaaca ggaaggaaaa ccgtatcaag atatcaagtc   24540
atggtattct ttttcattct tacagaaaag aattcacaag agacttgagg aagctttttt   24600 attttatt tgttctgttt atttatttat tttaagatgg ggtctcaccc tgttgcccag   24660
gttggtctca aacttctggg ctcaagtgat ctgcccactt cggcctccca aattgctgtg   24720
attacaggca tgagccactg cgcctggcca atttttttt ttttttttt tttgcgacaa   24780 ggtctttctc tagagtgcag tggcatgttc acagcttagt gcagccttga cctcccagcc   24840
tcaagtgatc cttccacctc agcctcctta gtagctagga ctacaggcat cactaggact   24900
acaggtgcca ccaccacgtc cagctaattt tcgtattgtt tgtagagacg gggtttcacc   24960
gtgtttctca ggctggtctc aaactccttg gctcaagcaa tttaaggaag cttttcatta   25020
gagtctaaaa atacatattt gaattgaatg acacaggggt gacactagtc agagaattag   25080
gaaaatgtga tatgcgtgtt agttccagtg caaaccggag agcccgttaa cctccctggg   25140 actgggttc ctcctctgca cagcaaggct cccctgtcct tccccatggg agacaagaat   25200
cacatcacca gcatgttttc ctctccccctt tggctgccag gaaactcaag agtcaaattc   25260
aaggctttat tgaaggaact ctgcaggacc caggacgtga tatcttgata ctgtttttcct   25320 tcctggtttt tgaccttctg ttccaacttg cgttttccct gattatagca ttttattat   25380 tttcatattt agtatgtagt gcacattttt acactacact tctaatcctt tgtgtaatga   25440
tcatggtaga aataaatggt gaaatgagga ggtcccactt agatgagttt caggggtcct   25500
tccagtccca attttccagg attcttaagg ggaaaaagta attttacatg tctgaaggt   25560 tccaggtttg cacagaaggg aactctccta tcgagagtcc tgaggacttc agcagacctc   25620
cagggaggcc tgtccaggat gttctcctac gtctgtaaag gagtgagcac tttgtgctag   25680
tttagggaaa gacagctttt ctgttgggat tttagactta ccctgcttga aattggtgga   25740
aaaatacctg tctgggatgg ggctcaataa tctgcagctg tattaggaaa tgcaagtagt   25800
tttgatgtgg gtggtttcaa gacatatttg gaaaatgtga gggaaatgtg tatgtgcatt   25860
tgctgagcgg gggactggtg aaggatcacc gatccattta ttcctaatgc tcatctcagc   25920
tttttattgt gccgagtacc ttgataaggc ttgggttatt ttatgagcgt ttatatataa   25980
attgatagtg tccatcagat catgtatatt tagaggcatg ctcctactt gagtaaatgg   26040 aaagctttag agatatacac taaataaaca tcagttacta attaaaaatt ccctcctcac   26100
tttaccaaag gacccaccat gggttccatt aaatgtctat ttatggtttg ttttgacaaa   26160
gacttttcca agaacacctc tgttctgtaa agcagaagag ctgtgtagat gttccagagt   26220
cgcttggtgt aaatttggtt ctgatttgtg ccgtgaagcc caataacaaa ctggaggcac   26280
acatttcaaa gccagtggta agagtttgag tagtgatcat ctattcctga acataaagtc   26340
```

```
tggagccttc tggaatccat aaaaatggaa tgatttgttc ctttcccctc taaccaaatt   26400
ttattcatac ctggctataa atagcttctg ttttgagttt tcactggtca gaccctgctg   26460
ttttagtgcc atcctgttag cttccttgaa caaggtaatg ccacctaaca tgttttttca   26520
gacttccagg acaatgatca gggggacttc tctatgccac actgggaggt gtgaaggtgt   26580
aggcttaggg caaccccctc tgagaagggg tggcaggtgg aggagcccat tgatcctttc   26640
tatcagggat ggatttgctt tctgtgggtg tcaccttcag gggcctgtgt tcccactcat   26700
cacaggagct catatttact cagtggggcc agagtgttct tcatacatgg tgattttact   26760
cctcaccata acctccgtgg tgcgtgctaa catgaccacc attttgcaga tgagaacatg   26820
gaggcttgca ggggaggtaa gttgccccag gttccatgct gaatcagagg tcaagctcag   26880
cacacagcac aggaccaagt ctgctggttc ccaagctcac atccttacct acaactctga   26940
atcaccccac agcagagtca acaagctggc ctggcatgtg aagaagcaag cctgggtgtc   27000
tcctggctgc cagtgccatc cctgccccgg gaccctaatc cacagtttga ttctggtcct   27060
tttgccctct gtccctcacc agaaccctga tatttccaga tgaaaacacg agtatagctt   27120
atttccacaa ctcacctggg cccagcaatc aagatctata gctataggga agtattgagt   27180
tgattatgag ttatataggt caaaatgagt agcttgcttg attgaagcag gtaattcgtg   27240
ccatacttt ctctttggga agacctgtac caacaataac ctctgctaaa cactttcgct   27300
tttttaaatt tgcaggtact tttttggggc tgtctttggc tgcctgtctg ttgagagttt   27360
gttttcttta cagtccatct gatttacagt ccctccgggt tgatttgtct catttgggaa   27420
tgagaaattt tattttaatg cattaagtaa tagtgttgag tggccaacaa atgtgaagtt   27480
tgaaaagctc aaatgaaaaa aaagtgtga tagaaacaca gagttggggg ccgggtgcag   27540
tggctcacac ctgtatttcc ggcactgtgg gaggccaaga caggaggatc ccttgagctc   27600
aggagtttga gacccctggg caacatggca agacccaag accccatctc tacaaaaaaa   27660
atgtaaaaat cagccagggg taatcccagc tacttgggag gctgaggtgg aaggattgct   27720
tgagcccggg aggttgaggc tgcagtgagc tgtgatcgat ctactggact ccagcctgag   27780
tgacagagca agaccctatc taaaaaaaaa aaaaaaaaa aaaaagaag aagaagaaca   27840
caggttggaa tttgaggggg cctgttaaat aggatgctct ttcctgcctt agttttgaat   27900
taattgagaa gataaaataa taaggcatgg agattagagc atcccctttc ttttttttctt   27960
tttctttttct tttttctttt tttctttttt acttttgct cttcttggcc aggctggagt   28020
gcaatggcac aatcttggct caccacaacc tccgcctcgc gggttcaagc aattctcttg   28080
cctcagcttc cccagtagct ggggttacag ccacgtgcca tgatgcccag ctaatttgt   28140
attttcagta gagacgggt ttctccatgt tggtcaggct ggtctcgaac tcccacctc   28200
aggtaatcca cccgcctcgg cctcccaaag tgctgggaat acaggcatga gccaccaggc   28260
ccggcagcat cccctttctt attgataaag cagatcttgg agaatgggag atcctgagcg   28320
gggttcctaa tgctagcctt caacatcagg ctgaggctca ccttgtcttc aagtaatggg   28380
cagtgctggc ctgaagggga gcctcctctg tccaggctc agcttatcct tggaaggctt   28440
agcacattga ggagctgctc caggctaaga gggagggact ggggtactct gtagaggttg   28500
ttcttccagt ttcttcaatc agatgagcca cactgtcact ctagtgttga aaggaggaa   28560
gggacagagg tggccaggag tgtgacccta aagaggcag aggagacctc agagaaagag   28620
aagaagcatt ctcctaacca gagggagaag gagagaggcc tcagttctcc ctctctggga   28680
attaatttga gatttacatt tagtgtctat aaacatgtca gcagatatat aaacttatt   28740
```

```
gcttttgctt tgtttccatt tttagattct tgagtatcag aacaccacct tctttggtgg   28800
aacctgtata tccatgattg attacctcct ctggccctgg tttgagcggc tggatgtgta   28860
tgggatactg gagtaagaca tttgacattg tggtgttaaa ttcccggagt cacactgagt   28920
aacaatggtt aagatggtct gcatgccccc tgtagacatg tttcaggatg tctgtgaagt   28980
gaatcaggtt tctaaaccgc agtgtgtgct tccttgttaa aaacatatgt gcttttccac   29040
tgctaacttc agacccacac tttgcccgca tttctgcaga tcagacccct agcccaggag   29100
cctcccgcag acttcagagc ctgctgtcct caccagcgcc cccacatggc cggtctgaga   29160
gcaagtggag agtcacagtc acagtcacag tgcccaacgc ctccacctgg tcctgacggg   29220
tccccagggg acaccatata accttagtca tgtctcattg cccggaggaa tcttccccca   29280
gataggaata accttataaa aaagatttgt gtagtaatat atgcttgata ttggaacata   29340
caaacaaaat ggcagtgaca cactatggaa gtatggaagt gcagggacat taaaggagaa   29400
gaaatagctg tgtaggctcc tgggcagagc agtgctgtgt tacttcaaag ctcagtgaag   29460
ctggacgtgt gcggacgtcc accctaatcc aagccaccct catggtgggt gctggacatt   29520
tctggcactt ggaaatccgg ccctgctgaa gcagaactgt gtctgcacct tcataacccg   29580
tgggctggag cccaaccagc cactgtctcc tgcacttccg acttcagctc tctttgtcag   29640
gatatttaaa actcaatatc aaacataaaa tttacaaaag gctgtatcct ctgaagacag   29700
agcatggagt cacaggttag gaaacctcac ttctagtcct ggattcccga caacccattc   29760
atattatctt cagcttattg ctttataaac cccagaacta aatatcctgg ttgagctttg   29820
aaagagccct gtcggctcca tgacttcaag gtttcatcct tgttttattc atttaaaaaa   29880
tgttttagaa attatttgtc tttatttttt tatatctcct aaagtaaaat ctgagaatga   29940
cccaagaata tttgtttcag agggttgtct ttttgttggc aagcagtgaa gcacatgtaa   30000
gtttctcaag ctttagaata tatatatatt aaaaaacaaa acaaaaaaaa tgaagcacag   30060
acatgttatt ttcccagagc catcagtcca agtatttca ctgtattatt agaagcaaca   30120
acttctaaac attcaactat tccaaaaata agattttcct ccagtaagtt atcattctca   30180
cttgataata agataactaa gataacttcc caaataaact cattcttcat atcttgcaaa   30240
tctaaaaagc aacgtgcatc ccctttcctg atgcctaccc ctgcactgtg ctgacgcttc   30300
tttcctgtct tgcagctgtg tgagccacac gccagccctg cggctctgga tatcagccat   30360
gaagtgggac cccacagtct gtgctcttct catggataag agcatttcc agggcttctt   30420 gaatctctat tttcagaaca accctaatgc ctttgacttt gggctgtgct gagtctcact   30480
gtccacccct tcgctgtcca gaattcccca gcttgttggg agtctacgtc acggcttgtc   30540
ttgggaacca atccgtctct ctttcttttc tttgaagttc ccaataaaat gaaaacagga   30600
aatgtattct tctgataatc atttgtctga ctcctctag                         30639
```

<210> SEQ ID NO 2
<211> LENGTH: 11
<212> TYPE: PRT
<213> ORGANISM: Homo sapien

<400> SEQUENCE: 2

Met Ser Gly Asp Ala Thr Arg Thr Leu Gly Lys
 1               5                   10

<210> SEQ ID NO 3
<211> LENGTH: 37

```
<212> TYPE: PRT
<213> ORGANISM: Homo sapien

<400> SEQUENCE: 3

Gly Ser Gln Pro Pro Gly Pro Val Pro Glu Gly Leu Ile Arg Ile Tyr
 1               5                  10                  15

Ser Met Arg Phe Cys Pro Tyr Ser His Arg Thr Arg Leu Val Leu Lys
                20                  25                  30

Ala Lys Asp Ile Arg
            35

<210> SEQ ID NO 4
<211> LENGTH: 74
<212> TYPE: PRT
<213> ORGANISM: Homo sapien

<400> SEQUENCE: 4

His Glu Val Val Asn Ile Asn Leu Arg Asn Lys Pro Glu Trp Tyr Tyr
 1               5                  10                  15

Thr Lys His Pro Phe Gly His Ile Pro Val Leu Glu Thr Ser Gln Cys
                20                  25                  30

Gln Leu Ile Tyr Glu Ser Val Ile Ala Cys Glu Tyr Leu Asp Asp Ala
            35                  40                  45

Tyr Pro Gly Arg Lys Leu Phe Pro Tyr Asp Pro Tyr Leu Arg Ala Arg
        50                  55                  60

Gln Lys Met Leu Leu Glu Leu Phe Cys Lys
65                  70

<210> SEQ ID NO 5
<211> LENGTH: 34
<212> TYPE: PRT
<213> ORGANISM: Homo sapien

<400> SEQUENCE: 5

Val Pro His Leu Thr Lys Glu Cys Leu Val Ala Leu Arg Cys Gly Arg
 1               5                  10                  15

Glu Cys Thr Asn Leu Lys Ala Ala Leu Arg Gln Glu Phe Ser Asn Leu
                20                  25                  30

Glu Glu

<210> SEQ ID NO 6
<211> LENGTH: 36
<212> TYPE: PRT
<213> ORGANISM: Homo sapien

<400> SEQUENCE: 6

Ile Leu Glu Tyr Gln Asn Thr Thr Phe Phe Gly Gly Thr Cys Ile Ser
 1               5                  10                  15

Met Ile Asp Tyr Leu Leu Trp Pro Trp Phe Glu Arg Leu Asp Val Tyr
                20                  25                  30

Gly Ile Leu Asp
            35

<210> SEQ ID NO 7
<211> LENGTH: 51
<212> TYPE: PRT
<213> ORGANISM: Homo sapien

<400> SEQUENCE: 7

Cys Val Ser His Thr Pro Ala Leu Arg Leu Trp Ile Ser Ala Met Lys
```

```
                      1               5                  10                 15
Trp Asp Pro Thr Val Cys Ala Leu Leu Met Asp Lys Ser Ile Phe Gln
                20                  25                  30

Gly Phe Leu Asn Leu Tyr Phe Gln Asn Asn Pro Asn Ala Phe Asp Phe
                35                  40                  45

Gly Leu Cys
        50

<210> SEQ ID NO 8
<211> LENGTH: 732
<212> TYPE: DNA
<213> ORGANISM: Homo sapien

<400> SEQUENCE: 8
atgtctgggg atgcgaccag gaccctgggg aaaggaagcc agcccccagg gccagtcccg      60
gaggggctga tccgcatcta cagcatgagg ttctgcccct attctcacag gacccgcctc     120
gtcctcaagg ccaaagacat cagacatgaa gtggtcaaca ttaacctgag aaacaagcct     180
gaatggtact atacaaagca ccctttggc cacattcctg tcctggagac cagccaatgt      240
caactgatct atgaatctgt tattgcttgt gagtacctgg atgatgctta tccaggaagg     300
aagctgtttc catatgaccc ttatgaacga gctcgccaaa agatgttatt ggagctattt     360
tgtaaggtcc cacatttgac caaggagtgc ctggtagcgt tgagatgtgg gagagaatgc     420
actaatctga aggcagccct gcgtcaggaa ttcagcaacc tggaagagat tcttgagtat     480
cagaacacca ccttctttgg tggaacctgt atatccatga ttgattacct cctctggccc     540
tggtttgagc ggctggatgt gtatgggata ctggactgtg tgagccacac gccagccctg     600
cggctctgga tatcagccat gaagtgggac cccacagtct gtgctcttct catggataag     660 agcatttttcc agggcttctt gaatctctat tttcagaaca accctaatgc ctttgacttt     720
gggctgtgct ga                                                         732

<210> SEQ ID NO 9
<211> LENGTH: 243
<212> TYPE: PRT
<213> ORGANISM: Homo sapien

<400> SEQUENCE: 9

Met Ser Gly Asp Ala Thr Arg Thr Leu Gly Lys Gly Ser Gln Pro Pro
 1               5                  10                  15

Gly Pro Val Pro Glu Gly Leu Ile Arg Ile Tyr Ser Met Arg Phe Cys
                20                  25                  30

Pro Tyr Ser His Arg Thr Arg Leu Val Leu Lys Ala Lys Asp Ile Arg
            35                  40                  45

His Glu Val Val Asn Ile Asn Leu Arg Asn Lys Pro Glu Trp Tyr Tyr
        50                  55                  60

Thr Lys His Pro Phe Gly His Ile Pro Val Leu Glu Thr Ser Gln Cys
65                  70                  75                  80

Gln Leu Ile Tyr Glu Ser Val Ile Ala Cys Glu Tyr Leu Asp Asp Ala
                85                  90                  95

Tyr Pro Gly Arg Lys Leu Phe Pro Tyr Asp Pro Tyr Glu Arg Ala Arg
            100                 105                 110

Gln Lys Met Leu Leu Glu Leu Phe Cys Lys Val Pro His Leu Thr Lys
        115                 120                 125

Glu Cys Leu Val Ala Leu Arg Cys Gly Arg Glu Cys Thr Asn Leu Lys
    130                 135                 140
```

```
Ala Ala Leu Arg Gln Glu Phe Ser Asn Leu Glu Glu Ile Leu Glu Tyr
145                 150                 155                 160

Gln Asn Thr Thr Phe Phe Gly Gly Thr Cys Ile Ser Met Ile Asp Tyr
                165                 170                 175

Leu Leu Trp Pro Trp Phe Glu Arg Leu Asp Val Tyr Gly Ile Leu Asp
            180                 185                 190

Cys Val Ser His Thr Pro Ala Leu Arg Leu Trp Ile Ser Ala Met Lys
                195                 200                 205

Trp Asp Pro Thr Val Cys Ala Leu Leu Met Asp Lys Ser Ile Phe Gln
        210                 215                 220

Gly Phe Leu Asn Leu Tyr Phe Gln Asn Asn Pro Asn Ala Phe Asp Phe
225                 230                 235                 240

Gly Leu Cys

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tgtaaaacga cggccagt                                                 18

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
caggaaacag ctatgacc                                                 18

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
tgtaaaacga cggccagtgg gcaggagtca gcaataaa                           38

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
caggaaacag ctatgaccgg tcttcagggc aacaata                            38

<210> SEQ ID NO 14
<211> LENGTH: 40
<212> TYPE: DNA
<213> ORGANISM: Artificial Sequence
<220> FEATURE:
<223> OTHER INFORMATION: Primer

<400> SEQUENCE: 14
```
tgtaaaacga cggccagttg ctctcttgtt gcttgtcttc                40

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
caggaaacag ctatgaccag cctgctgaat cggaaat                  37

<210> SEQ ID NO 16
<211> LENGTH: 38
<212> TYPE: DNA
<213> ORGANISM: Artificial Sequence
<220> FEATURE:
<223> OTHER INFORMATION: Primer

<400> SEQUENCE: 16
tgtaaaacga cggccagttt cgccattgag agaaacct                 38

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
caggaaacag ctatgaccct caaacccctc ttcccttc                 38

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
tgtaaaacga cggccagtta gttggcgggt aggatcac                 38

<210> SEQ ID NO 19
<211> LENGTH: 38
<212> TYPE: DNA
<213> ORGANISM: Artificial Sequence
<220> FEATURE:
<223> OTHER INFORMATION: Primer

<400> SEQUENCE: 19
caggaaacag ctatgaccgt ggtttgcgaa ggtttcat                 38

<210> SEQ ID NO 20
<211> LENGTH: 41
<212> TYPE: DNA
<213> ORGANISM: Artificial Sequence
<220> FEATURE:
<223> OTHER INFORMATION: Primer

<400> SEQUENCE: 20
tgtaaaacga cggccagttc tttggtggca ttattttcct a             41

<210> SEQ ID NO 21
<211> LENGTH: 41
<212> TYPE: DNA
<213> ORGANISM: Artificial Sequence

```
<220> FEATURE:
<223> OTHER INFORMATION: Primer

<400> SEQUENCE: 21
caggaaacag ctatgaccaa ccttttgga tttcactttc c                              41

<210> SEQ ID NO 22
<211> LENGTH: 38
<212> TYPE: DNA
<213> ORGANISM: Artificial Sequence
<220> FEATURE:
<223> OTHER INFORMATION: Primer

<400> SEQUENCE: 22
tgtaaaacga cggccagtag ccgggaacca atatgtct                                 38

<210> SEQ ID NO 23
<211> LENGTH: 38
<212> TYPE: DNA
<213> ORGANISM: Artificial Sequence
<220> FEATURE:
<223> OTHER INFORMATION: Primer

<400> SEQUENCE: 23
caggaaacag ctatgacccg taatggctgc tcaacaaa                                 38

<210> SEQ ID NO 24
<211> LENGTH: 41
<212> TYPE: DNA
<213> ORGANISM: Artificial Sequence
<220> FEATURE:
<223> OTHER INFORMATION: Primer

<400> SEQUENCE: 24
tgtaaaacga cggccagtgc tgtacttact taccaaagag t                             41

<210> SEQ ID NO 25
<211> LENGTH: 41
<212> TYPE: DNA
<213> ORGANISM: Artificial Sequence
<220> FEATURE:
<223> OTHER INFORMATION: Primer

<400> SEQUENCE: 25
caggaaacag ctatgaccga ccccatggag agcactcacc t                             41

<210> SEQ ID NO 26
<211> LENGTH: 42
<212> TYPE: DNA
<213> ORGANISM: Artificial Sequence
<220> FEATURE:
<223> OTHER INFORMATION: Primer

<400> SEQUENCE: 26
tgtaaaacga cggccagtga gctccgggag ctgcgcaaac ca                            42

<210> SEQ ID NO 27
<211> LENGTH: 45
<212> TYPE: DNA
<213> ORGANISM: Artificial Sequence
<220> FEATURE:
<223> OTHER INFORMATION: Primer

<400> SEQUENCE: 27
caggaaacag ctatgaccgg gctcctgtga ggcgctgggt ttgct                         45
```

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
tgtaaaacga cggccagtct gattgcttct gctttcaaga aga        43

<210> SEQ ID NO 29
<211> LENGTH: 42
<212> TYPE: DNA
<213> ORGANISM: Artificial Sequence
<220> FEATURE:
<223> OTHER INFORMATION: Primer

<400> SEQUENCE: 29
caggaaacag ctatgaccca tgctagctaa tctcctgagg at        42

<210> SEQ ID NO 30
<211> LENGTH: 44
<212> TYPE: DNA
<213> ORGANISM: Artificial Sequence
<220> FEATURE:
<223> OTHER INFORMATION: Primer

<400> SEQUENCE: 30
tgtaaaacga cggccagtgc tggagttata aagcttcgct gcct        44

<210> SEQ ID NO 31
<211> LENGTH: 42
<212> TYPE: DNA
<213> ORGANISM: Artificial Sequence
<220> FEATURE:
<223> OTHER INFORMATION: Primer

<400> SEQUENCE: 31
tgtaaaacga cggccagtga aaggaagcaa ttcatggcat gt        42

<210> SEQ ID NO 32
<211> LENGTH: 43
<212> TYPE: DNA
<213> ORGANISM: Artificial Sequence
<220> FEATURE:
<223> OTHER INFORMATION: Primer

<400> SEQUENCE: 32
caggaaacag ctatgaccga gaagaagcat tctcctaacc aga        43

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
tgtaaaacga cggccagtct gattcacttc acagacatcc tga        43

<210> SEQ ID NO 34
<211> LENGTH: 44
<212> TYPE: DNA
<213> ORGANISM: Artificial Sequence
<220> FEATURE:
<223> OTHER INFORMATION: Primer
<210> SEQ ID NO 34
<211> LENGTH: 44
<212> TYPE: DNA
<213> ORGANISM: Artificial Sequence
<220> FEATURE:
<223> OTHER INFORMATION: Primer

<400> SEQUENCE: 34
caggaaacag ctatgaccct cattcttcat atcttgcaaa tcta                         44

<210> SEQ ID NO 35
<211> LENGTH: 43
<212> TYPE: DNA
<213> ORGANISM: Artificial Sequence
<220> FEATURE:
<223> OTHER INFORMATION: Primer

<400> SEQUENCE: 35
caggaaacag ctatgaccca agctggggaa ttctggacag cga                          43

<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36
tgtaaaacga cggccagttt tcctgtcttg cagctgtg                                38

<210> SEQ ID NO 37
<211> LENGTH: 38
<212> TYPE: DNA
<213> ORGANISM: Artificial Sequence
<220> FEATURE:
<223> OTHER INFORMATION: Primer

<400> SEQUENCE: 37
caggaaacag ctatgacctc ccaaaatgtg ctctgaca                                38

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
tgtaaaacga cggccagtcc tgcctagcct gtagcttct                               39

<210> SEQ ID NO 39
<211> LENGTH: 39
<212> TYPE: DNA
<213> ORGANISM: Artificial Sequence
<220> FEATURE:
<223> OTHER INFORMATION: Primer

<400> SEQUENCE: 39
caggaaacag ctatgacctc aactttatcc ccagtgtgc                               39

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
aggacccgcc tcatcctcaa g                                                  21

<210> SEQ ID NO 41
<211> LENGTH: 21

```
<212> TYPE: DNA
<213> ORGANISM: Artificial Sequence
<220> FEATURE:
<223> OTHER INFORMATION: Primer

<400> SEQUENCE: 41
cttgaggatg aggcgggtcc t                                              21

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
accaaggagt acctggtagc gttg                                           24

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
caacgctacc aggtactcct tggt                                           24

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
gaatgcacta atctgaaggc a                                              21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
tgccttcaga ttagtgcatt c                                              21

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
gaagagatta ttgagtatca g                                              21

<210> SEQ ID NO 47
<211> LENGTH: 21
<212> TYPE: DNA
<213> ORGANISM: Artificial Sequence
<220> FEATURE:
<223> OTHER INFORMATION: Primer
```

```
-continued

<400> SEQUENCE: 47
ctgatactca ataatctctt c                                              21
```

US 7,390,894 B2

GLUTATHIONE S-TRANSFERASE SEQUENCE VARIANTS

CROSS-REFERENCE TO RELATED APPLICATIONS

This application claims priority to U.S. Provisional Patent Application Ser. No. 60/697,128, filed on Jul. 7, 2005, the entire contents of which are hereby incorporated by reference.

STATEMENT AS TO FEDERALLY SPONSORED RESEARCH

This invention was made with government support under grant nos. GM28157, GM35720, and GM61388, awarded by the National Institutes of Health. The government has certain rights in the invention.

TECHNICAL FIELD

This document relates to GSTO2 nucleic acid and amino acid sequence variants.

BACKGROUND

The Omega class of glutathione transferases (GSTs) have been identified in organisms including human, mouse, rat, pig, *Caenorhabditis elegans,* and *Drosophila melanogaster.* These GSTs, which include glutathione S-transferase omega 2 (GSTO2) have poor activity with common GST substrates, but exhibit novel glutathione-dependent thioltransferase, dehydroascorbate reductase, and monomethylarsonate reductase activities, and also modulate calcium release by ryanodine receptors. The GSTO2 gene contains seven exons, the first of which does not contain GSTO2 coding sequence. The GSTO2 gene is separated from the GSTO1 gene by 7.5 kb on chromosome 10q24.3. GSTO2 is expressed at high levels in the testes, and also is expressed in liver, kidney, skeletal muscle, heart, and lung, with low level expression in the cervix, ovary, and prostate. Substrates for GSTO2 include monomethylarsonic acid (MMV), which is reduced from the $^+$V form to the $^+$III form, as well as dehydroascorbate (DHA) and glutathione (GSH), which can be reacted to give ascorbate and glutathione disulfate.

SUMMARY

This document is based on the discovery of sequence variants that occur in both coding and non-coding regions of GSTO2 nucleic acids. Certain GSTO2 nucleotide sequence variants encode GSTO2 enzymes that are associated with individual differences in enzymatic activity. Other GSTO2 sequence variants in non-coding regions of the GSTO2 nucleic acid may alter regulation of transcription and/or splicing of the GSTO2 nucleic acid. Discovery of these sequence variants allows individual differences in the metabolism of drugs and other xenobiotics in humans to be assessed such that particular treatment regimens can be tailored to an individual based on the presence or absence of one or more sequence variants. For example, the presence of absence of a particular variant may indicate an individual's ability to metabolize arsenic, which is a contaminant in drinking water, and which can cause skin, bladder, kidney, liver, and lung cancer in individuals subjected to chronic arsenic exposure. The presence of absence of a particular variant also may indicate an individual's ability to metabolize arsenic trioxide, an agent that can be used to treat acute promyelocytic leukemia. Identification of GSTO2 sequence variants also may allow predisposition to cancer or conditions such as Alzheimer's or Parkinson's disease to be assessed in individuals.

In one aspect, this document features an isolated nucleic acid molecule consisting essentially of a variant GSTO2 nucleic acid sequence, wherein the variant GSTO2 nucleic acid sequence is selected from the group consisting of: a) at least ten contiguous nucleotides of SEQ ID NO:8, wherein said sequence includes nucleotide 121, 389, or 472 of SEQ ID NO:5, with the proviso that the nucleotide at position 121 is adenine, the nucleotide at position 389 is adenine, or the nucleotide at position 472 is adenine; b) at least ten contiguous nucleotides of SEQ ID NO:1, wherein said sequence includes nucleotide 15569, 15811, 15918, 15984, 16006, 16016, 16041, 16403, 16477, 16801, 16851, 16945, or 16948 of SEQ ID NO:1, with the proviso that a guanine is inserted after the nucleotide at position 15569, the nucleotide at position 15811 is cytosine, the nucleotide at position 15918 is thymine, the nucleotide at position 15984 is guanine, the nucleotide at position 16006 is cytosine, the nucleotide at position 16016 is adenine, the nucleotide at position 16041 is thymine, the nucleotide at position 16403 is thymine, the nucleotide at position 16477 is adenine, the nucleotide at position 16801 is cytosine, a thymine is inserted after the nucleotide at position 16851, the nucleotide at position 16945 is thymine, or the nucleotide at position 16948 is guanine; c) at least ten contiguous nucleotides of SEQ ID NO:1, wherein said sequence includes nucleotide 16957, 17056, 17119, 17132, 17158, 17172, or 17348 of SEQ ID NO:1, with the proviso that the nucleotide at position 16957 is guanine, the nucleotide at position 17056 is adenine, the nucleotide at position 17119 is adenine, the nucleotide at position 17132 is cytosine, the nucleotide at position 17158 is adenine, the nucleotide at position 17172 is guanine, or the nucleotide at position 17348 is thymine; d) at least ten contiguous nucleotides of SEQ ID NO:1, wherein said sequence includes nucleotide 17402, 17502, 17659 and 17662, 17683, 17752, 17785, 17827, 19044, 19496, 21635, 22747, or 22754 of SEQ ID NO:1, with the proviso that the nucleotide at position 17402 is guanine, the nucleotide at position 17502 is thymine, the nucleotides at positions 17660 and 17661 are deleted, the nucleotide at position 17683 is cytosine, the nucleotide at position 17752 is thymine, the nucleotide at position 17785 is adenine, a thymine is inserted after the nucleotide at position 17827, the nucleotide at position 19044 is guanine, the nucleotide at position 19496 is guanine, the nucleotide at position 21635 is thymine, the nucleotide at position 22747 is adenine, or the nucleotide at position 22754 is adenine; e) at least ten contiguous nucleotides of SEQ ID NO:1, wherein said sequence includes nucleotide 23291, 26236, 27722, 47154, or 47188 of SEQ ID NO:1, with the proviso that the nucleotide at position 23291 is thymine, the nucleotide at position 26236 is thymine, the nucleotide at position 27722 is cytosine, the nucleotide at position 47154 is guanine, or the nucleotide at position 47188 is thymine; f) at least ten contiguous nucleotides of SEQ ID NO:1, wherein said sequence includes nucleotide 47713, 47876, 48248, 48282, or 48357 of SEQ ID NO:1, with the proviso that the nucleotide at position 47713 is thymine, the nucleotide at position 47876 is guanine, the nucleotide at position 48248 is thymine, the nucleotide at position 48282 is cytosine, or the nucleotide at position 48357 is thymine; and g) the complement of a), b), c), d), e), or f). The isolated nucleic acid can be from 10 to 100 nucleotides in length or from 20 to 50 nucleotides in length.

This document also features a vector comprising the nucleic acid molecule described herein. The nucleic acid molecule can be from 20 to 50 nucleotides in length.

In another aspect, this document features an isolated nucleic acid encoding a GSTO2 polypeptide, wherein the polypeptide contains a GSTO2 amino acid sequence variant relative to the amino acid sequence of SEQ ID NO:9, and wherein the amino acid sequence variant is at a residue selected from the group consisting of 41, 130, and 158. The amino acid sequence variant can be an isoleucine at residue 41, a tyrosine at residue 130, or an isoleucine at residue 158.

In another aspect, this document features an isolated GSTO2 polypeptide, wherein the polypeptide contains a GSTO2 amino acid sequence variant relative to the amino acid sequence of SEQ ID NO:9, and wherein the amino acid sequence variant is at a residue selected from the group consisting of 41, 130, and 158. The amino acid sequence variant can be an isoleucine at residue 41, a tyrosine at residue 130, or an isoleucine at residue 158.

In still another aspect, this document features an article of manufacture comprising a substrate, wherein the substrate comprises a population of isolated variant GSTO2 nucleic acid molecules as disclosed herein. The article of manufacture can comprises a plurality of discrete regions, wherein each region comprises a different population of isolated variant GSTO2 nucleic acid molecules, and wherein each population of molecules comprises a different GSTO2 nucleotide sequence variant.

This document also features a method for determining a GSTO2 genotype. The method can comprise: a) providing a nucleic acid sample from a subject, and b) screening the nucleic acid sample for one or more genetic markers in linkage disequilibrium with a GSTO2 allele. The GSTO2 allele can be selected from the group consisting of a G121A allele, a G389A allele, an A424G allele, or a C472A allele.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 1 shows the nucleotide sequence of the reference GSTO1 and GSTO2 genes (SEQ ID NO:1), and the amino acid sequence of the reference GSTO2 polypeptide (SEQ ID NOs:2, 3, 4, 5, 6, and 7). Exons are depicted in bold type and non-coding sequences are in regular type. Positions of single nucleotide polymorphisms (SNPs) are circled, as are the positions of amino acid changes that result from the SNPs. Primers are underlined, and start and stop codons are double-underlined. Exon 1 contains nucleotides 16954 to 17312 of SEQ ID NO:1. Intron 1 contains nucleotides 17313 to 22765 of SEQ ID NO:1. Exon 2 contains nucleotides 22766 to 23051 of SEQ ID NO:1. The translation initiation codon begins at nucleotide 22997 of SEQ ID NO:1, within exon 2. Intron 2 contains nucleotides 23052 to 23306 of SEQ ID NO:1. Exon 3 contains nucleotides 23307 to 23415 of SEQ ID NO:1. Intron 3 contains nucleotides 23416 to 25974 of SEQ ID NO:1. Exon 4 contains nucleotides 25975 to 26197 of SEQ ID NO:1. Intron 4 contains nucleotides 26198 to 27450 of SEQ ID NO:1. Exon 5 contains nucleotides 27451 to 27552 of SEQ ID NO:1. Intron 5 contains nucleotides 27553 to 45658 of SEQ ID NO:1. Exon 6 contains nucleotides 45659 to 45765 of SEQ ID NO:1. Intron 6 contains nucleotides 45766 to 47208 of SEQ ID NO:1. Exon 7 contains nucleotides 47209 to 47496 of SEQ ID NO:1.

FIG. 2 shows the open reading frame (SEQ ID NO:8) of the reference GSTO2, and also shows the reference amino acid sequence (SEQ ID NO:9) of the encoded GSTO2. Positions of cSNPs are circled, as are the positions of amino acid changes that result from the cSNPs. Start and stop codons are double-underlined.

DETAILED DESCRIPTION

Figure 3:
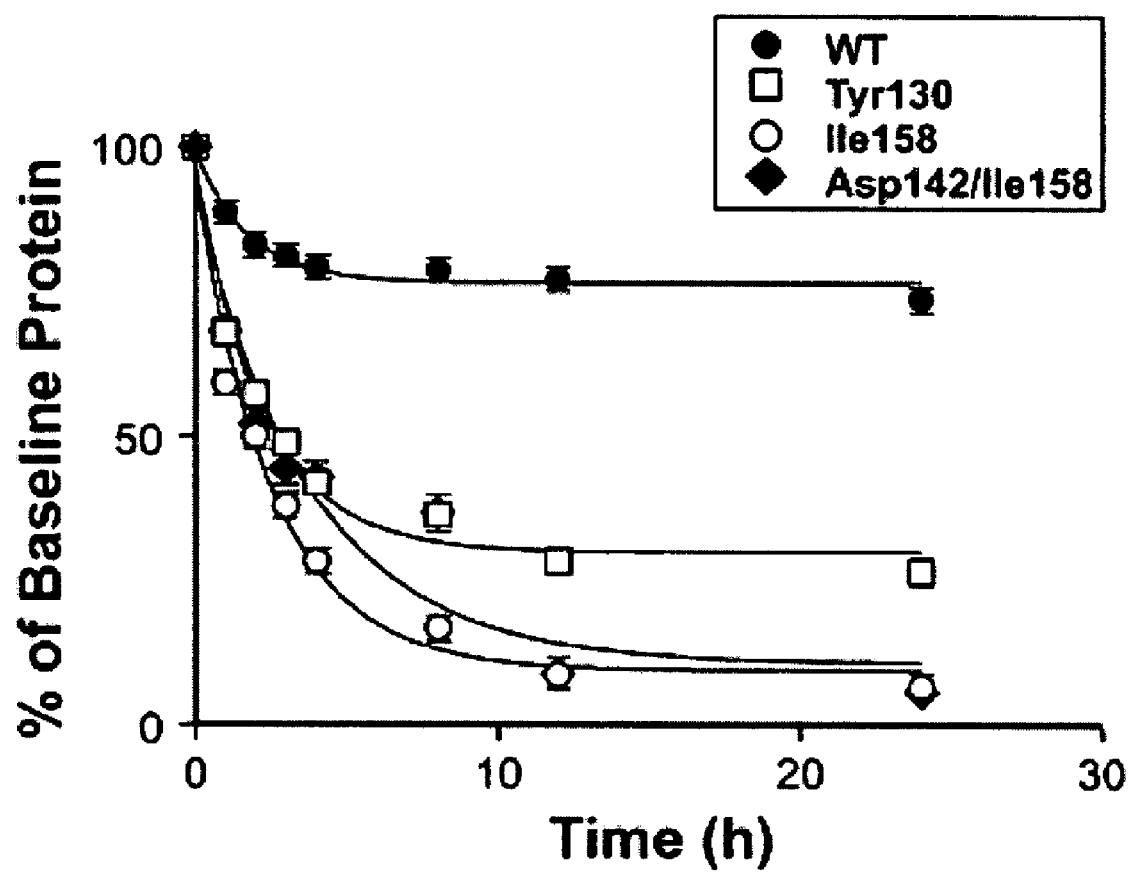
FIG. 3 is a graph plotting protein degradation data for the indicated GSTO2 allozymes.

This document features GSTO2 nucleotide and amino acid sequence variants. GSTO2 is thought to be a cytoplasmic enzyme that has glutathione transferase and glutathione dehydrogenase activity. For example, GSTO2 can catalyze the transfer of glutathione to an aliphatic, aromatic, or heterocyclic molecule, wherein the linkage is via a thiol group. GSTO2 also can catalyze the dehydrogenation of DHA, which can be reacted with GSH to give ascorbate and glutathione disulfate. Genetically-based variations in GSTO2 activity that lead to altered levels of GSTO2 or altered GSTO2 activity may be important in particular diseases or clinical conditions.

Nucleic Acid Molecules

Provided herein are isolated nucleic acids that include a GSTO2 nucleic acid sequence. The GSTO2 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-GSTO2 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids provided herein are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids can be in a sense or antisense orientation, can be complementary to the GSTO2 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in a GSTO2 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference GSTO2 nucleic acid sequence is provided in FIG. 1 (SEQ ID NO:1) and in GenBank (Accession No. NT_030059). The reference GSTO2 ORF is provided in FIG. 2 (SEQ ID NO:8), as is the corresponding reference GSTO2 amino acid sequence (SEQ ID NO:9). The mRNA and amino acid reference sequences also are found in GenBank (Accession No. NM_183239). The nucleic acid and amino acid reference sequences also are referred to herein as "wild type."

As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences can be designated as "−X" relative to the "A" in the translation initiation codon; positions of nucleotide sequence variants in the coding sequence and 3' untranslated sequence can be designated as "+X" or "X" relative to the "A" in the translation initiation codon. Nucleotide sequence variants that occur in introns can be designated as "+X" or "X" relative to the "G" in the splice donor site (GT) or as "−X" relative to the "G" in the splice acceptor site (AG).

In some embodiments, a GSTO2 nucleotide sequence variant encodes a GSTO2 polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-225 residues, or a full-length GSTO2 polypeptide). GSTO2 polypeptides may or may not have GSTO2 catalytic activity, or may have altered activity relative to the reference GSTO2 polypeptide. Polypeptides that do not have activity or have altered activity can be useful for diagnostic purposes (e.g., for producing antibodies having specific binding affinity for variant GSTO2 polypeptides).

Corresponding GSTO2 polypeptides, irrespective of length, that differ in amino acid sequence are herein referred to as allozymes. For example, a GSTO2 nucleic acid sequence that includes an adenine at position 121 relative to the adenine in the translation initiation codon (i.e., nucleotide 23393 of SEQ ID NO:1 or nucleotide 121 of SEQ ID NO:8) encodes a GSTO2 polypeptide having an isoleucine at amino acid residue 41. This polypeptide (Val4IIle) would be considered an allozyme with respect to the reference GSTO2 polypeptide that contains a valine at amino acid residue 41. Additional non-limiting examples of GSTO2 sequence variants that alter amino acid sequence include variants at nucleotides 389, 424, and 472 relative to the adenine in the translation initiation codon (i.e., positions 27473, 27508, and 45662, respectively, of SEQ ID NO:1, or positions 389, 424, and 472, respectively, of SEQ ID NO:8). For example, a GSTO2 nucleic acid molecule can include an adenine at nucleotide 389 and encode a GSTO2 polypeptide having a tyrosine at amino acid residue 130 in place of a cysteine residue (Cys130Tyr); a guanine at nucleotide 424 and encode a GSTO2 polypeptide having an aspartic acid at amino acid residue 142 in place of an asparagine residue (Asn142Asp), or an adenine at nucleotide 472 and encode a GSTO2 polypeptide having an isoleucine at amino acid 158 in place of a leucine residue (Leu158Ile).

GSTO2 allozymes as described above are encoded by a series of GSTO2 alleles. These alleles represent nucleic acid sequences containing sequence variants, typically multiple sequence variants, within coding and non-coding sequences. Representative examples of single nucleotide variants are described herein. Table 2 sets out a series of GSTO2 alleles that encode GSTO2. Some alleles are commonly observed, i.e., have allele frequencies >1%, such as the allele having a guanine at nucleotide 424 place of an adenine. The relatively large number of alleles and allozymes for GSTO2 indicates the potential complexity of GSTO2 pharmacogenetics. Such complexity emphasizes the need for determining single nucleotide variants, (i.e., single nucleotide polymorphisms, SNPs) as well as complete GSTO2 haplotypes (i.e., the set of alleles on one chromosome or a part of a chromosome) of patients.

Certain GSTO2 nucleotide sequence variants do not alter the amino acid sequence. Such variants, however, could alter regulation of transcription as well as mRNA stability. GSTO2 variants can occur in intron sequences, for example, within introns 1, 2, 4, 5, or 6. For example, nucleotide sequence variants in the first intron can include a guanine substitution at nucleotide 52 (i.e., nucleotide 17402 of SEQ ID NO:1), a thymine substitution at nucleotide 152 (i.e., nucleotide 17502 of SEQ ID NO:1), deletion of cytosine and guanine residues at nucleotides 310 and 311 (i.e., nucleotides 17660 and 17661 of SEQ ID NO:1), an adenine substitution at nucleotide 311 (i.e., nucleotide 17661 of SEQ ID NO:1), a cytosine substitution at nucleotide 333 (i.e., nucleotide 17683 of SEQ ID NO:1), a thymine substitution at nucleotide 402 (i.e., nucleotide 17752 of SEQ ID NO:1), a cytosine substitution at nucleotide 426 (i.e., nucleotide 17776 of SEQ ID NO:1), an adenine substitution at nucleotide 435 (i.e., nucleotide 17785 of SEQ ID NO:1), insertion of a thymine after nucleotide 477 (i.e., nucleotide 17827 of SEQ ID NO:1), a guanine substitution at nucleotide 1694 (i.e., nucleotide 19044 of SEQ ID NO:1), a guanine substitution at nucleotide 2003 (i.e., nucleotide 19353 of SEQ ID NO:1), a guanine substitution at nucleotide 2146 (i.e., nucleotide 19496 of SEQ ID NO:1), an adenine substitution at nucleotide 2168 (i.e., nucleotide 19518 of SEQ ID NO:1), a thymine substitution at nucleotide −1131 (i.e., nucleotide 21635 of SEQ ID NO:1), a guanine substitution at nucleotide −185 (i.e., nucleotide 22581 of SEQ ID NO:1), an adenine substitution at nucleotide −19 (i.e., nucleotide 22747 of SEQ ID NO:1), or an adenine substitution at nucleotide −12 (i.e., nucleotide 22754 of SEQ ID NO:1). Other examples of sequence variants within introns include a thymine substitution at nucleotide −16 of intron 2 (i.e., nucleotide 23291 of SEQ ID NO:1), a cytosine substitution at nucleotide 20 of intron 4 (i.e., nucleotide 26217 of SEQ ID NO:1), a thymine substitution at nucleotide 39 of intron 4 (i.e., nucleotide 26236 of SEQ ID NO:1), a cytosine substitution at nucleotide −38 of intron 4 (i.e., nucleotide 27413 of SEQ ID NO:1), a guanine substitution at nucleotide 74 of intron 5 (i.e., nucleotide 27626 of SEQ ID NO:1), a cytosine substitution at nucleotide 170 of intron 5 (i.e., nucleotide 27722 of SEQ ID NO:1), a guanine substitution at nucleotide −55 of intron 6 (i.e., nucleotide 47154 of SEQ ID NO:1), or a thymine substitution at nucleotide −21 of intron 6 (i.e., nucleotide 47188 of SEQ ID NO:1).

GSTO2 nucleotide sequence variants that do not change the amino acid sequence also can be within an exon or in 5' or 3' untranslated sequences. For example, a GSTO2 nucleotide sequence variant within exon 2 can be a guanine substitution at nucleotide −183 relative to the adenine in the translation initiation codon. Exon 7 sequence variants can include, for example, a thymine substitution at nucleotide 591 (i.e., nucleotide 47224 of SEQ ID NO:1 or nucleotide 591 of SEQ ID NO:8), or a thymine substitution at nucleotide 630 (i.e., nucleotide 47263 of SEQ ID NO:1 or nucleotide 630 of SEQ ID NO:8).

GSTO2 variants within the 5' FR (including the first exon) can be, for example, insertion of a guanine after nucleotide −2012 (i.e., nucleotide 15569 of SEQ ID NO:1) relative to the adenine in the translation initiation codon, a cytosine substitution at nucleotide −1785 (i.e., nucleotide 15797 of SEQ ID NO:1), a cytosine substitution at nucleotide −1771 (i.e., nucleotide 15811 of SEQ ID NO:1), a thymine substitution at nucleotide −1664 (i.e., nucleotide 15918 of SEQ ID NO:1), a guanine substitution at nucleotide −1598 (i.e., nucleotide 15984 of SEQ ID NO:1), a cytosine substitution at nucleotide −1576 (i.e., nucleotide 16006 of SEQ ID NO:1), an adenine substitution at nucleotide −1566 (i.e., nucleotide 16016 of SEQ ID NO:1), a thymine substitution at nucleotide −1541 (i.e., nucleotide 16041 of SEQ ID NO:1), an adenine substitution at nucleotide −1357 (i.e., nucleotide 16225 of SEQ ID NO:1), a cytosine substitution at nucleotide −1189 (i.e., nucleotide 16393 of SEQ ID NO:1), a thymine substitution at nucleotide −1179 (i.e., nucleotide 16403 of SEQ ID NO:1), an adenine substitution at nucleotide −1105 (i.e., nucleotide 16477 of SEQ ID NO:1), a guanine substitution at nucleotide −1102 (i.e., nucleotide 16480 of SEQ ID NO:1), a thymine substitution at nucleotide −1009 (i.e., nucleotide 16573 of SEQ ID NO:1), a cytosine substitution at nucleotide −781 (i.e., nucleotide 16801 of SEQ ID NO:1), insertion of a thymine after nucleotide −730 (i.e., nucleotide 16851 of SEQ ID NO:1), a thymine substitution at nucleotide −637 (i.e., nucleotide 16945 of SEQ ID NO:1), a guanine substitution at nucleotide −634 (i.e., nucleotide 16948 of SEQ ID NO:1), a guanine substitution at nucleotide −625 (i.e., nucleotide 16957 of SEQ ID NO:1), a guanine substitution at nucleotide −530 (i.e., nucleotide 17052 of SEQ ID NO:1), an adenine substitution at nucleotide −526 (i.e., nucleotide 17056 of SEQ ID NO:1), an adenine substitution at nucleotide −463 (i.e., nucleotide 17119 of SEQ ID NO:1), a cytosine substitution at nucleotide −450 (i.e., nucleotide 17132 of SEQ ID NO:1), an adenine substitution at nucleotide −424 (i.e., nucleotide 17158 of SEQ ID NO:1), a guanine substitution at nucleotide −410 (i.e., nucleotide 17172 of SEQ ID NO:1), a thymine substitution at nucleotide −293 (i.e., nucleotide 17289 of SEQ ID NO:1), or a thymine substitution at nucleotide −234 (i.e., nucleotide 17348 of SEQ ID NO:1).

GSTO2 variants within the 3' untranslated region can be, for example, a thymine substitution at nucleotide 1038 (i.e., nucleotide 47671 of SEQ ID NO:1) relative to the adenine in the translation initiation codon, a thymine substitution at nucleotide 1080 (i.e., nucleotide 47713 of SEQ ID NO:1), a guanine substitution at nucleotide 1243 (i.e., nucleotide 47876 of SEQ ID NO:1), a guanine substitution at nucleotide 1343 (i.e., nucleotide 47976 of SEQ ID NO:1), a thymine substitution at nucleotide 1615 (i.e., nucleotide 48248 of SEQ ID NO:1), a cytosine substitution at nucleotide 1649 (i.e., nucleotide 48282 of SEQ ID NO:1), or a thymine substitution at nucleotide 1724 (i.e., nucleotide 48357 of SEQ ID NO:1).

In some embodiments, a GSTO2 nucleic acid molecule can consist essentially of at least ten (e.g., at least 12, at least 15, at least 18, at least 20, or at least 25) contiguous nucleotides of an GSTO2 reference sequence (e.g., SEQ ID NO:1 or SEQ ID NO:8). Such nucleic acids can contain one or more variant positions, with the proviso that the nucleotides at those positions are variant nucleotides as disclosed herein in Table 2, for example. A GSTO2 nucleic acid "consisting essentially of" a particular sequence has the basic and novel characteristic that it can be used to distinguish, based upon hybridization, a nucleic acid having a sequence that contains a variant from a corresponding nucleic acid having a sequence that does not contain the variant (e.g., a wild type sequence). Such nucleic acid molecules can include additional sequences or labels (e.g., a tag or a fluorescent label as disclosed herein), provided that such additions do not affect the basic and novel characteristic of the nucleic acid molecules.

In some embodiments, a GSTO2 nucleic acid sequence can have at least 90% (e.g., 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity with a region of SEQ ID NO:1 or SEQ ID NO:8. The region of SEQ ID NO:1 or SEQ ID NO:8 is at least ten nucleotides in length (e.g., 10, 15, 20, 50, 60, 70, 75, 100, 150 or more nucleotides in length). For example, a nucleic acid can include a GSTO2 nucleic acid sequence with at least 90% identity to nucleotides 75 to 175, 350 to 450, 375 to 475, 425 to 525, 550 to 650, or 600 to 700 of SEQ ID NO:8. A variant GSTO2 nucleotide sequence can have an adenine at nucleotide 121, an adenine at nucleotide 389, an adenine at nucleotide 424, an adenine at nucleotide 472, a thymine at nucleotide 591, or a thymine at nucleotide 630, and combinations thereof, wherein the numbering of the positions is with respect to the numbering of SEQ ID NO:8.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (B12seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S.

government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: –i is set to a file containing the first nucleic acid sequence to be compared (e.g., C:\seq1.txt); –j is set to a file containing the second nucleic acid sequence to be compared (e.g., C:\seq2.txt); –p is set to blastn; –o is set to any desired file name (e.g., C:\output.txt); –q is set to –1; –r is set to 2; and all other options are left at their default setting. The following command will generate an output file containing a comparison between two sequences: C:\Bl2seq –i c:\seq1.txt –j c:\seq2.txt –p blastn –o c:\output.txt –q –1 –r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 969 nucleotides from the target sequence aligned with a region of the sequence set forth in SEQ ID NO:1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900÷969×100=93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing a GSTO2 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, the reference sequences depicted in FIGS. 1 or 2 can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified include those described herein.

GSTO2 Polypeptides

Isolated GSTO2 polypeptides provided herein include an amino acid sequence variant relative to the reference GSTO2 (SEQ ID NO:9, FIG. 2; GenBank Accession No. NM_183239). The term "isolated" with respect to a GSTO2 polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

GSTO2 polypeptides can include variants at one or more of amino acid residues 41, 130, 142, and 158. In particular, an isoleucine residue can be substituted at position 41, a tyrosine residue at position 130, an aspartic acid residue at position 142, or an isoleucine residue at position 158. In some embodiments, activity of GSTO2 polypeptides is altered relative to the reference GSTO2. Certain GSTO2 allozymes can have reduced activity, while other allozymes can have activity that is comparable to the reference GSTO2. Other allozymes can have increased activity relative to the reference GSTO2. Activity of GSTO2 polypeptides can be assessed in vitro. For example, reduction of DHA catalyzed by bacterially expressed GSTO2 can be detected by monitoring an increase in absorbance at 265 nm. Alternatively, activity of GSTO2 polypeptides can be assessed in vivo (e.g., in COS cells).

Other biochemical properties of allozymes, such as apparent $K_m$ values, also can be altered relative to the reference GSTO2. Apparent $K_m$ values can be calculated using, for example, the method of Wilkinson with a computer program written by Cleland. Wilkinson (1961) *Biochem. J.* 80:324-332; and Cleland (1963) *Nature* 198:463-365.

Isolated polypeptides can be obtained, for example, by extraction from a natural source (e.g., testes, liver, kidney, or skeletal muscle), chemical synthesis, or by recombinant production in a host cell. To recombinantly produce GSTO2 polypeptides, a nucleic acid encoding a GSTO2 nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to a GSTO2 nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include pBAD (Invitrogen, Carlsbad, Calif.), the pTYB family of vectors (New England Biolabs), and pGEMEX vectors (Promega); representative mammalian expression vectors include pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include pBacPAK8 or pBacPAK9 (Clontech), and p2Bac (Invitrogen); and representative yeast expression vectors include MATCHMAKER (Clontech) and pPICZ A, B, and C (Invitrogen).

In bacterial systems, a strain of *Escherichia coli* can be used to express GSTO2 variant polypeptides. For example, BL-21 cells can be transformed with a pGEX vector containing a GSTO2 nucleic acid sequence. The transformed bacteria can be grown exponentially and then stimulated with isopropylthiogalactopyranoside (IPTG) prior to harvesting. In general, the GSTO2-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed GSTO2 polypeptide can be released from the GST moiety.

In eukaryotic host cells, a number of viral-based expression systems can be utilized to express GSTO2 variant polypeptides. A nucleic acid encoding a polypeptide can be cloned into, for example, a baculoviral vector such as pBlue-Bac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides can be identified by standard methodology.

Alternatively, a nucleic acid encoding a polypeptide can be introduced into a SV40, retroviral, or vaccinia based viral vector and used to infect suitable host cells.

Eukaryotic cell lines that stably express GSTO2 variant polypeptides can be produced using expression vectors with the appropriate control elements and a selectable marker. For example, the eukaryotic expression vector pCR3.1 (Invitrogen, San Diego, Calif.) and p91023(B) (see Wong et al. (1985) *Science* 228:810-815) or modified derivatives thereof are suitable for expression of GSTO2 variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pCR3.1, pCDNA3.1 (Invitrogen), or pcDNA4/HisMax TOPO (Promega) and then transcribed and translated in vitro using wheat germ extract or rabbit reticulocyte lysate.

GSTO2 variant polypeptides can be purified by known chromatographic methods including ion exchange and gel filtration chromatography. See, for example, Caine et al. (1996) *Protein Expr. Purif.* 8:159-166. GSTO2 polypeptides can be "engineered" to contain a tag sequence describe herein that allows the polypeptide to be purified (e.g., captured onto an affinity matrix). Immunoaffinity chromatography also can be used to purify GSTO2 polypeptides.

Non-Human Mammals

Also featured herein are non-human mammals that include GSTO2 nucleic acids as described herein, as well as progeny and cells of such non-human mammals. Non-human mammals include, for example, rodents such as rats, guinea pigs, and mice, and farm animals such as pigs, sheep, goats, horses, and cattle. Non-human mammals can express a GSTO2 variant nucleic acid in addition to an endogenous GSTO2 (e.g., a transgenic non-human that includes a GSTO2 nucleic acid randomly integrated into the genome of the non-human mammal). Alternatively, an endogenous GSTO2 nucleic acid can be replaced with a GSTO2 variant nucleic acid by homologous recombination. See, Shastry (1998) *Mol. Cell Biochem.* 181:163-179, for a review of gene targeting technology.

In one embodiment, non-human mammals are produced that lack an endogenous GSTO2 nucleic acid (i.e., a knockout), and then a GSTO2 variant nucleic acid as provided herein is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous GSTO2 nucleic acid. That is, cultured ES cells can be transformed with a knockout construct and cells selected in which the GSTO2 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning, A Laboratory Manual*, second edition, Cold Spring Harbor Press, Plainview; N.Y., 1989.

To generate a knockout animal, ES cells having at least one inactivated GSTO2 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated GSTO2 allele. If the original ES cell was heterozygous for the inactivated GSTO2 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the GSTO2 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals. For example, fetal fibroblasts can be genetically modified such that they contain an inactivated endogenous GSTO2 gene and express a GSTO2 nucleic acid, and then fused with enucleated oocytes. After activation of the oocytes, the eggs are cultured to the blastocyst stage, and implanted into a recipient. See, Cibelli et al. (1998) *Science* 280:1256-1258. Adult somatic cells, including, for example, cumulus cells and mammary cells, can be used to produce animals such as mice and sheep, respectively. See, for example, Wakayama et al. (1998) *Nature* 394:369-374; and Wilmut et al. (1997) *Nature* 385:810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama et al., supra.

Non-human mammals such as mice can be used, for example, to screen toxicity of compounds that are substrates for GSTO2, drugs that alter GSTO2 activity, or for carcinogenesis. For example, GSTO2 activity or toxicity can be assessed in a first group of such non-human mammals in the presence of a compound, and compared with GSTO2 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting GSTO2 Sequence Variants

GSTO2 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al. (1995) *Nat. Biotechnol.* 15:33-39), denaturing high performance liquid chromatography (DHPLC, Underhill et al. (1997) *Genome Res.* 7:996-1005), infrared matrix-assisted laser desorption/ionization (IR-MALDI) mass spectrometry (WO 99/57318), and combinations of such methods.

Genomic DNA generally is used in the analysis of GSTO2 nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the GSTO2 gene can be amplified then directly sequenced. Dye primer sequencing can be used to increase the accuracy of detecting heterozygous samples.

Nucleic acid molecules provided herein can be used to detect variant GSTO2 sequences. For example, allele specific hybridization also can be used to detect sequence variants, including complete haplotypes of a subject (e.g., a mammal such as a human). See, Stoneking et al. (1991) *Am. J. Hum. Genet.* 48:370-382; and Prince et al. (2001) *Genome Res.* 11:152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For GSTO2 sequence variants that do not alter a common restriction site, mutagenic primers can be designed that introduce a restriction site when the variant allele is present or when the wild type allele is present. A portion of GSTO2 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of GSTO2 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al. (2001) *Genome* 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, GSTO2 variants can be detected by antibodies that have specific binding affinity for variant GSTO2 polypeptides. Variant GSTO2 polypeptides can be produced in various ways, including recombinantly, as discussed above. Host animals such as rabbits, chickens, mice, guinea pigs, and rats can be immunized by injection of a GSTO2 variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a GSTO2 variant polypeptide and standard hybridoma technology. In particular, monoclonal antibodies can be obtained by any technique that provides for the production of antibody molecules by continuous cell lines in culture such as described by Kohler et al. (1975) *Nature* 256:495, the human B-cell hybridoma technique (Kosbor et al. (1983) *Immunology Today* 4:72; Cote et al. (1983) *Proc. Natl. Acad. Sci USA* 80:2026), and the EBV-hybridoma technique (Cole et al., *Monoclonal Antibodies and Cancer Therapy*, Alan R. Liss, Inc., pp. 77-96 (1983). Such antibodies can be of any immunoglobulin class including IgG, IgM, IgE, IgA, IgD and any subclass thereof. A hybridoma producing monoclonal antibodies can be cultivated in vitro or in vivo.

Antibody fragments that have specific binding affinity for a GSTO2 variant polypeptide can be generated using known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science*, 246:1275 (1989). Once produced, antibodies or fragments thereof are tested for recognition of GSTO2 variant polypeptides by standard immunoassay methods including ELISA techniques, radioimmunoassays and Western blotting. See, *Short Protocols in Molecular Biology*, Chapter 11, Green Publishing Associates and John Wiley & Sons, edited by Ausubel et al., 1992.

Methods

As a result of the present disclosure, it is possible to determine GSH transferase status of a subject (e.g., a mammal such as a human). "GSH transferase status" refers to the ability of a subject to transfer a glutathione group to a substrate. GSH transferase status of a subject can be determined by, for example, measuring the level of GSTO2 activity in the subject using, for example, the methods described herein. Alternatively, GSH transferase status can be evaluated by determining whether a GSH transferase nucleic acid sequence (e.g., a GSTO2 nucleic acid sequence) of a subject contains one or more variants (e.g., one or more variants that are correlated with increased or decreased GSH transferase activity). A variant that results in decreased or increased GSTO2 activity, for example, can be said to result in "reduced" or "enhanced" GSH transferase status, respectively. In some embodiments, the variant profile of a subject can be used to determine the GSH transferase status of the subject.

"Variant profile" refers to the presence or absence of a plurality (e.g., two or more) of GSTO2 nucleotide sequence variants or GSTO2 amino acid sequence variants. For example, a variant profile can include the complete GSTO2 haplotype of the mammal (e.g., see Tables 5-9) or can include the presence or absence of a set of particular non-synonymous SNPs (e.g., single nucleotide substitutions that alter the amino acid sequence of a GSTO2 polypeptide). In one embodiment, the variant profile includes detecting the presence or absence of two or more non-synonymous SNPs (e.g., 2, 3, or 4 non-synonymous SNPs) described herein. There may be ethnic-specific pharmacogenetic variation, as certain of the nucleotide and amino acid sequence variants described herein were detected solely in African-American, Caucasian-American, Han Chinese-American, or Mexican-American subjects. In addition, the variant profile can include detecting the presence or absence of any type of GSTO2 SNP together with any other GSTO2 SNP (e.g., a polymorphism pair or a group of polymorphism pairs). Such polymorphism pairs include, without limitation, the pairs described in Table 4. Further, a variant profile can include detecting the presence or absence of any GSTO2 SNP together with any SNP from other GSH transferases.

GSH transferase activity of an enzyme such as GSTO2 can be measured using, for example, in vitro methods such as those described herein. As used herein, the term "reduced GSH transferase status" refers to a decrease (e.g., a 5%, 10%, 15%, 20%, 25%, 30%, 40%, 50%, 60%, 70%, 75%, 80%, 90%, 95%, or 100% decrease) in GSH transferase activity (e.g., GSTO2 activity) of a subject, as compared to a control level of GSH transferase activity. Similarly, the term "enhanced GSH transferase status" refers to an increase (e.g., a 5%, 10%, 15%, 20%, 25%, 30%, 40%, 50%, 60%, 70%, 75%, 80%, 90%, 95%, 100%, or more than 100% increase) in GSH transferase activity of a subject, as compared to a control level of GSH transferase activity. A control level of GSH transferase activity can be, for example, an average level of GSH transferase activity in a population of individuals. In one embodiment, the population includes individuals that do not contain particular GSTO2 nucleotide sequence variants or particular GSTO2 amino acid sequence variants (e.g., particular variants that affect GSH transferase status). Alternatively, a control level of GSH transferase activity can refer to the level of GSH transferase activity in a control subject (e.g., a subject that does not contain a GSTO2 nucleic acid containing a variant).

In some embodiments, evaluation of GSH transferase status can be used in diagnostic assays to determine whether a particular therapy may be useful in an individual, or to tailor particular treatment regimens to an individual. For example, the presence of absence of one or more variants may indicate an individual's ability to metabolize arsenic, a drinking water contaminant, or arsenic trioxide, an agent that can be used to treat acute promyelocytic leukemia. In further embodiments, GSH transferase status can be linked to predisposition to a particular disease or condition. For example, identification of GSTO2 sequence variants also may allow predisposition to conditions such as cancer, Alzheimer's, or Parkinson's disease to be assessed in individuals. Additional risk factors including, for example, family history and other genetic factors can be considered when determining risk. Predisposition to such diseases can be determined based on the presence or absence of a single GSTO2 sequence variant or based on a variant profile.

Determination of GSH transferase status and predisposition to conditions such as cancer, Alzheimer's, or Parkinson's disease can include identification of genetic markers (e.g., polymorphisms) in linkage disequilibrium with particular GSTO2 alleles. Although such markers may not be relevant from a functional perspective (i.e., may not directly affect function of GSTO2), their presence can be predictive of functional/clinically relevant polymorphisms. Thus, this document also provides methods for detecting a genotype by screening for genetic markers in linkage disequilibrium with particular GSTO2 alleles. The methods can include providing a nucleic acid sample from a subject (e.g., a human subject), and screening the sample for one or more markers in linkage disequilibrium with a particular GSTO2 allele. For example, a method can include screening for markers in linkage disequilibrium with a SNP at nucleotide 121, 389, 424, or 472 relative to the adenine in the translation initiation codon (nucleotide 23393, 27473, 27508, or 45662, respectively, of SEQ ID NO:1). Methods also can include screening for genetic markers in linkage disequilibrium with any of the other SNPs shown in Table 2.

Articles of Manufacture

Articles of manufacture also are provided herein, and can include populations of isolated GSTO2 nucleic acid molecules or GSTO2 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different GSTO2 nucleic acid or GSTO2 polypeptide sequence variant. Such articles of manufacture can include two or more sequence variants of GSTO2, or can include all of the sequence variants known for GSTO2. For example, the article of manufacture can include two or more of the sequence variants identified herein and one or more other GSTO2 sequence variants, such as nucleic acid variants that occur in the promoter region of the GSTO2 gene. Furthermore, nucleic acid molecules containing sequence variants for other GSH transferases can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al. (1996) *Nature Genet.* 14:441-447; and U.S. Pat. Nos. 5,770, 722 and 5,733,729.

The invention will be further described in the following examples, which do not limit the scope of the invention described in the claims.

EXAMPLES

Example 1

Methods and Materials

PCR Amplification and DNA Sequencing: DNA samples from 60 Caucasian-American, 60 African-American, 60 Han Chinese-American, and 60 Mexican-American subjects were obtained from the Coriell Institute Cell Repository (Camden, N.J.). These samples had been anonymized, and written informed consent had been obtained from all donors for the use of their DNA for this purpose. All experiments were reviewed and approved by the Mayo Clinic Institutional Review Board. Fourteen PCR reactions were performed with each DNA sample to amplify all GSTO2 exons and splice junctions, as well as a portion of the 5' flanking region. Primers were designed to hybridize within introns, the 5'-FR, or the 3'-UTR. This approach was used to ensure that a GSTO2 processed pseudogene that maps to chromosome 3 (Whitbread et al. (2003) *Pharmacogenet.* 13:131-144) would not be amplified. Amplicons were sequenced using dye-primer sequencing chemistry to facilitate the identification of heterozygous bases (Chadwick et al. (1996) *Biotechniques* 20:676-683). To make that possible, universal M13 sequencing tags were added to the 5'-ends of each forward and reverse primer. Forward primers contained the M13 forward sequence (5'-TGTAAAACGACGGCCAGT-3'; SEQ ID NO:10), and reverse primers contained the M13 reverse sequence (5'-CAGGAAACAGCTATGACC-3'; SEQ ID NO:11). In addition, resequencing of the GSTO2 5'-FR and the intergenic area utilized dye terminator chemistry. The sequences and locations of each primer within the gene are listed in Table 1. "F" represents forward; "R," reverse; "U," upstream; "D," downstream; "I," intron; "FR," flanking region; and "UTR," untranslated region. The locations of primers within the gene were chosen to avoid repetitive sequence.

Amplifications were performed with AmpliTaq Gold DNA polymerase (Perkin Elmer, Foster City, Calif.) using a "hot start" to help ensure amplification specificity. Each 50 µl reaction mixture contained 1 U of DNA polymerase, 5 µl of a 10-fold diluted DNA sample (160-190 ng DNA), 10 pmol of each primer, 0.05 mM dNTP (Boehringer Mannheim, Indianapolis, Ind.), and 5 µl of 10×PCR buffer that contained 15 mM $MgCl_2$ (Perkin Elmer). Amplifications were performed with a Perkin Elmer model 9700 thermal cycler. PCR cycling parameters involved a 12 minutes hot start at 94° C., 30 cycles at 94° C. for 30 seconds, 30 seconds at the annealing temperature, and a final 10 minute extension at 72° C.

Amplicons were sequenced in the Mayo Molecular Biology Core Facility with an ABI 377 DNA sequencer using BigDye™ (Perkin Elmer) dye-primer sequencing chemistry. Both DNA strands were sequenced in all cases. To exclude PCR-induced artifacts, independent amplification followed by DNA sequencing was performed for all samples in which a SNP was only observed once among the samples resequenced, or for samples with ambiguous chromatograms. DNA sequence chromatograms were analyzed using the PolyPhred 3.0 (Nickerson et al. (1997) *Nucl. Acids Res.* 25:2745-2751) and Consed 8.0 (Gordon et al. (1998) *Genome Res.* 8:195-202) programs developed by the University of Washington (Seattle, Wash.). The University of Wisconsin GCG software package, Version 10, was also used to analyze nucleotide sequence. GenBank accession numbers for the GSTO2 reference sequences were NT_030059 and NM_183239.

Recombinant GSTO2 Expression Constructs and Allozyme Expression: A WT GSTO2 cDNA open reading frame (ORF) sequence was amplified from a pooled human liver cDNA library (Clontech, Mountain View, Calif.). Expression constructs for the nonsynonymous cSNPs observed during the resequencing studies were generated by site-directed mutagenesis using "circular PCR." Sequences of the site-directed mutagenesis primers are listed in Table 1. Site-directed mutagenesis amplification reactions contained 1 U of Pfu Turbo DNA polymerase (Stratagene, La Jolla, Calif.) in a final volume of 25 µl, 10 pmol of primers, 0.24 mM dNTPs, and 2.5 µl of 10×PCR buffer. The sequences of expression constructs were confirmed by sequencing in both directions after cloning into the eukaryotic expression vector pCR3.1 (Invitrogen, Carlsbad, Calif.).

WT and variant GSTO2 expression constructs were transfected into COS-1 cells, together with pSV-β-galactosidase DNA (Promega) to make it possible to use β-galactosidase activity to correct for transfection efficiency. Transfections were performed with Lipofectamine 2000 (Invitrogen), and the cells were cultured for 48 hours in Dulbecco's modified Eagles medium (DMEM; Bio Whittaker, Walkersville, Md.) with 10% fetal bovine serum (Clontech). Cells were homogenized with a Polytron homogenizer (Brinkmann Instruments, Westbury, N.Y.). The homogenates were centrifuged at 100,000×g for 1 hour; and supernatant preparations were stored at −80° C.

Western Blot Analysis: Rabbit polyclonal antibodies were generated to GSTO2 (Cocalico Biologicals, Reamstown, Pa.) using a polypeptide that corresponded to amino acids 10 to 30, with an additional cysteine residue at the amino terminus. This synthetic polypeptide was conjugated to keyhole limpet hemocyanin prior to immunization of rabbits. For quantitative Western blot analysis, cytosol preparations of COS-1 cells transfected with the expression constructs were loaded on a 12% polyacrylamide gel on the basis of β-galactosidase activity to correct for possible variation in transfection efficiency. After SDS-PAGE, the proteins were transferred to a nitrocellulose membrane that was probed with rabbit antiserum to GSTO2, diluted 1:2000 with "blocking buffer." Goat anti-rabbit horseradish peroxidase, diluted 1:20,000, was used as the secondary antibody. Bound antibody was detected with the ECL Western blotting system (Amersham Pharmacia Biotech, Piscataway, N.J.). The level of immunoreactive protein was quantitated using IP Gel Lab (Biosystemetica, Plymouth, UK).

In vitro Translation and Degradation: Selected GSTO2 expression constructs were transcribed and translated in vitro in the presence of $^{35}$S-methionine (1000 Ci/mmol, 2.5 mCi total activity) (Amersham Pharmacia Biotech) using the TNT coupled rabbit reticulocyte lysate (RRL) system (Promega, Madison, Wis.). Reaction mixtures used to generate radioactively labeled protein were incubated at 30° C. for 90 minutes, and 5 µl aliquots were used to perform SDS-PAGE with 10% gels. Protein degradation studies were performed as described (Wang et al. (2003) *Pharmacogenet.* 13:555-564). Briefly, 50 µl of an adenosine 5'-triphosphate (ATP) generating system, 50 µl of "untreated" RRL, and 10 µl of $^{35}$S-methionine radioactively labeled GSTO2 allozyme were mixed. This mixture was incubated at 37° C., and 10 µl aliquots were removed at various time intervals, followed by SDS-PAGE. After electrophoresis, the gels were dried, exposed to X-ray film and the bands of radioactively labeled protein were quantified.

Data analysis: Statistical comparison of the data was performed by ANOVA using the StatView program, version 4.5 (Abacus Concepts, Inc., Berkeley, Calif.). Values for π, θ, and Tajima's D were calculated as described by Tajima (Tajima (1989) *Genet.* 123:585-595), followed by correction for length. Linkage analysis was performed after all DNA samples had been genotyped at each of the polymorphic sites observed, using the EH program developed by Terwilliger and Ott, *Handbook of Human Genetic Linkage,* The Johns Hopkins University Press, Baltimore, pp. 188-193 (1994). D' values, a quantitative method for reporting linkage data that is independent of allele frequency (Hartl and Clark *Principles of Population Genetics,* 3$^{rd}$ edition, Sinauer Associates, Inc., (Sunderland, Mass.), pp. 96-106 (1997); and Hedrick *Genetics of Populations,* 2$^{nd}$ edition, Jones and Bartlett (Sudbury, Mass.), pp. 396-405 (2000)), were calculated. The genotype data also were used to assign inferred haplotypes using a program based on the E-M algorithm (Long et al. (1995) *Am. J. Hum. Genet.* 56:799-810; Excoffier and Slatkin (1995) *Mol. Biol. Evol.* 12:921-927; and Schaid et al. (2002) *Am. J. Hum. Genet.* 70:425-434). Unambiguous haplotype assignment was possible on the basis of genotype for samples that contained no more than one heterozygous polymorphism. Group mean values were compared using student's t-test. Degradation data were plotted using GraphPad Prism (GraphPad Software, San Diego, Calif.).

GSTO2 Enzyme Activity: GSTO2 activity is measured using a bacterially expressed GSTO2 polypeptide. DHA is combined with DHA and GSH, and GSTO2 activity is measured as increased absorbance at 265 nm, which results from reduction of the DHA. This method also can be used to estimate apparent Km values. Alternatively, GSTO2 enzyme activity is measured in vivo (e.g., in CHO cells).

Quantitative RT-PCR: mRNA is isolated from COS-1 cells cotransfected with a control β-Galactosidase reporter and a GSTO2 WT expression construct or GSTO2 variant expression construct using an RNeasy Mini Kit (Qiagen, Valencia, Calif.), according to the manufacturer's instructions. RT-PCR is performed with primers for both GSTO2 and β-Galactosidase as an internal control.

Confocal microscopy: Fluorescein isothiocyanate (FITC)-conjugated goat anti-mouse immunoglobulin and tetramethylrhodamine isothiocyanate (TRITC)-conjugated goat anti-rabbit immunoglobulin are commercially available (e.g., from Southern Biotech (Birmingham, Ala.)). COS-1 cells are subcultured to 50-70% confluence on coverslips, transfected with expression constructs, and cultured for 48 hours. The cells are washed with phosphate buffered saline (PBS), fixed with 3% paraformaldehyde for 12 minutes at room temperature, washed, and incubated at room temperature for 5 minutes with buffer containing 0.5% Triton X-100. The coverslips are then incubated with primary antibodies—rabbit polyclonal antihuman antibody against calnexin (an endoplasmic reticulum marker) and mouse monoclonal anti-His antibody, followed by FITC-conjugated goat anti-mouse or TRITC-conjugated goat anti-rabbit IgG antibody. The COS-1 cells are viewed using a Zeiss LSM 510 confocal microscope with 488 or 570 nm filters for excitation of the green or red fluorochrome, respectively.

GSTO2 reporter gene constructs and luciferase assay: Luciferase reporter gene constructs are created for the most common human GSTO2 5'-FR haplotypes (e.g., haplotypes having a frequency ≧3% in any of the populations). Specifically, a segment containing about 1000 bp of the GSTO2 5'-FR is amplified from human genomic DNA samples that contained the desired haplotypes. The forward and reverse primers include ACC65I and XhoI restriction sites, respectively, to enable subcloning of the amplicons into pGL-3 Basic (Promega), upstream of the firefly luciferase gene open reading frame (ORF). The insert is sequenced in both directions to ensure that the correct sequence is present.

The luciferase reporter gene constructs are used to transiently transfect primary cells or cell lines (e.g., liver, kidney, skeletal muscle, heart, lung, cervix, ovary, or prostate cells). Cells are transfected with 5 µg purified plasmid DNA with 50 ng pRL-TK (Promega) DNA. The Renilla luciferase activity expressed by pRL-TK is used as a control for transfection efficiency. Cells also are transfected with pGL-3 Basic without insert as a control. Transfection is performed using the TransFast reagent (Promega). After 48 hours, cells are lysed and reporter gene activity is measured using a Promega dual-luciferase assay system. Results are reported as the ratio of firefly luciferase light units to Renilla luciferase light units, and all values are expressed as a percentage of the activity of the pGL3 WT 5′-FR construct. All assays in three cell lines are performed at least in duplicate (e.g., in triplicate).

TABLE 1

PCR primers used for resequencing and site directed mutagenesis of GSTO2

| Primer Name | Region Amplified | Primer Sequence (5′ to 3′ direction) | SEQ ID NO |
|---|---|---|---|
| Resequencing primers | | | |
| GSTO1 3′UTR F(730) | 5′ FR | TGTAAAACGACGGCCAGTGGGC AGGAGTCAGCAATAAA* | 12 |
| UR(-1348) | 5′ FR | CAGGAAACAGCTATGACCGGTC TTCAGGGCCAACAATA | 13 |
| UF(-1462) | 5′ FR | TGTAAAACGACGGCCAGTTGCT CTCTTGTTGCTTGTCTTC | 14 |
| UR(-791) | 5′ FR | CAGGAAACAGCTATGACCAGCC TGCTGAATCGGAAAT | 15 |
| UF(-888) | 5′ FR | TGTAAAACGACGGCCAGTTTCG CCATTGAGAGAAACCT | 16 |
| I1R(48) | Exon 1 (5′ UTR) | CAGGAAACAGCTATGACCCTCA AACCCCTCTTCCCTTC | 17 |
| UF(-368) | Exon 1/ Intron 1 | TGTAAAACGACGGCCAGTTAGT TGGCGGGTAGGATCAC | 18 |
| I1R(539) | Exon 1/ Intron 1 | CAGGAAACAGCTATGACCGTGG TTTGCGAAGGTTTCAT | 19 |
| I1F(1608) | Intron 1 | TGTAAAACGACGGCCAGTTCTT TGGTGGCATTATTTTCCTA | 20 |
| I1R(2265) | Intron 1 | CAGGAAACAGCTATGACCAACC TTTTTGGATTTCACTTTCC | 21 |
| I1F(-1423) | Intron 1 | TGTAAAACGACGGCCAGTAGCC GGGAACCAATATGTCT | 22 |
| I1R(-1042) | Intron 1 | CAGGAAACAGCTATGACCCGTA ATGGCTGCTCAACAAA | 23 |
| I1F(-242) | Exon 2 | TGTAAAACGACGGCCAGTGCTG TACTTACTTACCAAAGAGT | 24 |
| I2R(21) | Exon 2 | CAGGAAACAGCTATGACCGACC CCATGGAGAGCACTCACCT | 25 |
| E2F(-34) | Exons 2 and 3 | TGTAAAACGACGGCCAGTGAGC TCCGGGAGCTGCGCAAACCA | 26 |
| I3R(54) | Exons 2 and 3 | CAGGAAACAGCTATGACCGGGC TCCTGTGAGGCGCTGGGTTTGCT | 27 |
| I3F(-85) | Exon 4 | TGTAAAACGACGGCCAGTCTGA TTGCTTCTGCTTTCAAGAAGA | 28 |
| I4R(140) | Exon 4 | CAGGAAACAGCTATGACCCATG CTAGCTAATCTCCTGAGGAT | 29 |
| I4F(-94) | Exon 5 | TGTAAAACGACGGCCAGTGCTG GAGTTATAAAGCTTCGCTGCCT | 30 |
| I5R(227) | Exon 5 | TGTAAAACGACGGCCAGTGAAA GGAAGCAATTCATGGCATGT | 31 |
| I5F(-148) | Exon 6 | CAGGAAACAGCTATGACCGAGA AGAAGCATTCTCCTAACCAGA | 32 |
| I6R(115) | Exon 6 | TGTAAAACGACGGCCAGTCTGA TTCACTTCACAGACATCCTGA | 33 |

TABLE 1-continued

PCR primers used for resequencing and site directed mutagenesis of GSTO2

| Primer Name | Region Amplified | Primer Sequence (5′ to 3′ direction) | SEQ ID NO |
|---|---|---|---|
| I6F(-97) | Exon 7 | CAGGAAACAGCTATGACCCTCA TTCTTCATATCTTGCAAATCTA | 34 |
| 3′UTR R(775) | Exon 7 | CAGGAAACAGCTATGACCCAAG CTGGGGAATTCTGGACAGCGA | 35 |
| I6F(-15) | Exon 7/ 3′ FR | TGTAAAACGACGGCCAGTTTTC CTGTCTTGCAGCTGTG | 36 |
| 3′FR R(1288) | Exon 7/ 3′ FR | CAGGAAACAGCTATGACCTCCC AAAATGTGCTCTGACA | 37 |
| 3′FR R(1218) | 3′ FR | TGTAAAACGACGGCCAGTCCTG CCTAGCCTGTAGCTTCT | 38 |
| 3′FR R(1855) | 3′ FR | CAGGAAACAGCTATGACCTCAA CTTTATCCCCAGTGTGC | 39 |
| Mutagenesis primers | | | |
| O2_V41I_F | | AGGACCGGCCTCATCCTCAAG** | 40 |
| O2_V41I_R | | CTTGAGGATGAGGCGGGTCCT | 41 |
| O2_C130Y_F | | ACCAAGGAGTACCTGGTAGCGTTG | 42 |
| O2_C130Y_R | | CAACGCTACCAGGTACTCCTTGGT | 43 |
| O2_N142D_F | | GAATGCACTAATCTGAAGGCA | 44 |
| O2_N142D_R | | TGCCTTCAGATTAGTGCATTC | 45 |
| O2_L158I_F | | GAAGAGATTATTGAGTATCAG | 46 |
| O2_L158I_R | | CTGATACTCAATAATCTCTTC | 47 |

*Underlined nucleotides in resequencing primers indicate M13 tag
**Underlined nucleotides in mutagenesis primers indicate variant

Example 2

GSTO2 Polymorphisms

Fourteen separate PCR amplifications were performed for each of the DNA samples studied. All PCR amplicons were sequenced on both strands, making it possible to verify the presence of polymorphisms using data from the complimentary strand. Approximately $3 \times 10^6$ pg of DNA was sequenced and analyzed, including the "intergenic" area located between the GSTO1 and GSTO2 genes (i.e., between the final exon of GSTO1 and the first exon of GSTO2). A total of 66 polymorphisms were observed (Table 2). Polymorphisms in exons and flanking regions (FR) are numbered relative to the adenine in the GSTO2 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1).

Variant allele frequencies ranged from 0.8% to 78.3%, with differences between the African-American (AA), Caucasian-American (CA), Han Chinese-American (HCA), and Mexican-American (MA) subjects. Fifty-four SNPs were observed in AA subjects, 19 in CA subjects, 17 in HCA subjects, and 36 in MA subjects. Nineteen of these polymorphisms were specific to AA, 5 to CA, and 2 each were specific to HCA and MA subjects.

Six SNPs were observed within the coding-region (cSNPs), and four of those cSNPs—located in exons 2, 4, and 5—were nonsynonymous, resulting in the amino acid alterations Val41Ile, Cys130Tyr, Asn142Asp, and Leu158Ile. The Val41Ile polymorphism had a frequency of 0.9% in African-Americans but was not observed in DNA from Caucasian-American, Han Chinese-American, or Mexican-American subjects. The Cys130Tyr polymorphism had frequencies of 0.8% in African Americans and 1.7% in Han Chinese-Americans, but was not observed in Caucasian-Americans or Mexican-Americans. The Asn142Asp polymorphism had frequencies of 23.3% in African-Americans, 69.2% in Caucasian-Americans, 78.3% in Han Chinese-Americans, and 74.2% in Mexican-Americans. The Leu158Ile polymorphism had a frequency of 0.8% in Caucasian-Americans, but was not observed in African-Americans, Han Chinese-Americans, or Mexican-Americans. To exclude artifacts introduced by PCR-dependent misincorporation, independent amplifications were performed and the amplicons were sequenced in all cases in which a polymorphism was observed only once among the DNA samples studied. All polymorphisms were in Hardy-Weinberg equilibrium (P>0.05).

Nucleotide diversity, a measure of genetic variation that is adjusted for the number of alleles studied, was calculated for the GSTO2 gene and for the intergenic region. Two standard measures of nucleotide diversity are $\pi$, average heterozygosity per site, and $\theta$, a population mutation measure that is theoretically equal to the neutral mutation parameter (Fullerton et al. (2000) *Am. J. Hum. Genet.* 67:881-900). Values for Tajima's D, a test for the neutral mutation hypothesis (Fullerton et al., supra), also were calculated (Table 3). Under conditions of neutrality, Tajima's D should equal 0. For GSTO2, none of the values for Tajima's D were statistically significant. For the intergenic region, Tajima's D value for AA subjects was statistically significant, raising the possibility that this area may be undergoing selection.

TABLE 2

Human GSTO2 polymorphisms and frequencies

| Polymorphism Position | Location in Gene | Position in SEQ ID 1 | Amino Acid Change | WT Nucleotide | Variant Sequence Nucleotide | AA | CA | HCA | MA |
|---|---|---|---|---|---|---|---|---|---|
| −2012-2013 | 5'FR | 15569/15570 | | | Insertion of G | 0.292 | 0.000 | 0.000 | 0.008 |
| −1785 | 5'FR | 15797 | | T | C | 0.050 | 0.000 | 0.000 | 0.000 |
| −1771 | 5'FR | 15811 | | G | C | 0.008 | 0.000 | 0.000 | 0.000 |
| −1664 | 5'FR | 15918 | | C | T | 0.300 | 0.000 | 0.000 | 0.008 |
| −1598 | 5'FR | 15984 | | C | G | 0.300 | 0.000 | 0.000 | 0.008 |
| −1576 | 5'FR | 16006 | | G | C | 0.300 | 0.000 | 0.000 | 0.008 |
| −1566 | 5'FR | 16016 | | G | A | 0.300 | 0.000 | 0.000 | 0.008 |
| −1541 | 5'FR | 16041 | | C | T | 0.008 | 0.000 | 0.000 | 0.000 |
| −1357 | 5'FR | 16225 | | C | A | 0.300 | 0.000 | 0.000 | 0.008 |
| −1189 | 5'FR | 16393 | | T | C | 0.300 | 0.000 | 0.000 | 0.008 |
| −1179 | 5'FR | 16403 | | G | T | 0.008 | 0.000 | 0.000 | 0.000 |
| −1105 | 5'FR | 16477 | | G | A | 0.117 | 0.258 | 0.167 | 0.242 |
| −1102 | 5'FR | 16480 | | T | G | 0.217 | 0.683 | 0.767 | 0.692 |
| −1009 | 5'FR | 16573 | | C | T | 0.300 | 0.000 | 0.000 | 0.008 |
| −781 | 5'FR | 16801 | | A | C | 0.283 | 0.000 | 0.000 | 0.008 |
| −730-731 | 5'FR | 16851/16852 | | | Insertion of T | 0.283 | 0.000 | 0.000 | 0.008 |
| −637 | 5'FR | 16945 | | C | T | 0.275 | 0.000 | 0.000 | 0.008 |
| −634 | 5'FR | 16948 | | C | G | 0.275 | 0.000 | 0.000 | 0.008 |
| −625 | Exon1 | 16957 | | A | G | 0.000 | 0.000 | 0.017 | 0.000 |
| −530 | Exon1 | 17052 | | C | G | 0.271 | 0.000 | 0.000 | 0.008 |
| −526 | Exon1 | 17056 | | C | A | 0.000 | 0.008 | 0.000 | 0.000 |
| −463 | Exon1 | 17119 | | G | A | 0.271 | 0.000 | 0.000 | 0.008 |
| −450 | Exon1 | 17132 | | A | C | 0.271 | 0.000 | 0.000 | 0.008 |
| −424 | Exon1 | 17158 | | G | A | 0.017 | 0.000 | 0.000 | 0.000 |
| −410 | Exon1 | 17172 | | T | G | 0.008 | 0.000 | 0.000 | 0.000 |
| −293 | Exon1 | 17289 | | A | T | 0.050 | 0.000 | 0.000 | 0.000 |
| −234 | Exon1 | 17348 | | C | T | 0.008 | 0.000 | 0.000 | 0.000 |
| 52 | Intron1 | 17402 | | A | G | 0.008 | 0.000 | 0.000 | 0.000 |
| 152 | Intron1 | 17502 | | G | T | 0.033 | 0.000 | 0.000 | 0.000 |
| 310-311 | Intron1 | 17660/17661 | | | Deletion of CG | 0.008 | 0.000 | 0.000 | 0.000 |
| 311 | Intron1 | 17661 | | G | A | 0.300 | 0.000 | 0.000 | 0.008 |
| 333 | Intron1 | 17683 | | T | C | 0.008 | 0.000 | 0.000 | 0.000 |
| 402 | Intron1 | 17752 | | C | T | 0.042 | 0.025 | 0.017 | 0.025 |
| 426 | Intron1 | 17776 | | T | C | 0.050 | 0.000 | 0.000 | 0.000 |
| 435 | Intron1 | 17785 | | T | A | 0.017 | 0.000 | 0.000 | 0.000 |
| 477-478 | Intron1 | 17827/17828 | | | Insertion of T | 0.008 | 0.033 | 0.033 | 0.000 |
| 1694 | Intron1 | 19044 | | A | G | 0.050 | 0.000 | 0.000 | 0.008 |
| 2003 | Intron1 | 19353 | | A | G | 0.300 | 0.000 | 0.000 | 0.008 |
| 2146 | Intron1 | 19496 | | A | G | 0.000 | 0.017 | 0.000 | 0.008 |
| 2168 | Intron1 | 19518 | | G | A | 0.200 | 0.000 | 0.017 | 0.017 |
| −1131 | Intron1 | 21635 | | C | T | 0.417 | 0.025 | 0.017 | 0.025 |
| −185 | Intron1 | 22581 | | A | G | 0.060 | 0.000 | 0.000 | 0.000 |
| −19 | Intron1 | 22747 | | T | A | 0.000 | 0.000 | 0.000 | 0.008 |
| −12 | Intron1 | 22754 | | G | A | 0.008 | 0.000 | 0.000 | 0.008 |
| −183 | Exon2 | 22814 | | A | G | 0.108 | 0.242 | 0.175 | 0.183 |
| −16 | Intron2 | 23291 | | C | T | 0.008 | 0.000 | 0.000 | 0.000 |
| 121 | Exon3 | 23393 | Val41Ile | G | A | 0.009 | 0.000 | 0.000 | 0.000 |

TABLE 2-continued

Human GSTO2 polymorphisms and frequencies

| Polymorphism Position | Location in Gene | Position in SEQ ID 1 | Amino Acid Change | WT Nucleotide | Variant Nucleotide | AA | CA | HCA | MA |
|---|---|---|---|---|---|---|---|---|---|
| 20 | Intron4 | 26217 | | T | C | 0.200 | 0.560 | 0.642 | 0.667 |
| 39 | Intron4 | 26236 | | C | T | 0.000 | 0.000 | 0.000 | 0.008 |
| −38 | Intron4 | 27413 | | A | C | 0.000 | 0.017 | 0.000 | 0.017 |
| 389 | Exon5 | 27473 | Cys130Tyr | G | A | 0.008 | 0.000 | 0.017 | 0.000 |
| 424 | Exon5 | 27508 | Asn142Asp | A | G | 0.233 | 0.692 | 0.783 | 0.742 |
| 74 | Intron5 | 27626 | | A | G | 0.233 | 0.692 | 0.783 | 0.742 |
| 170 | Intron5 | 27722 | | T | C | 0.000 | 0.008 | 0.000 | 0.000 |
| 472 | Exon6 | 45662 | Leu158Ile | C | A | 0.000 | 0.008 | 0.000 | 0.000 |
| −55 | Intron6 | 47154 | | C | G | 0.058 | 0.000 | 0.008 | 0.000 |
| −21 | Intron6 | 47188 | | C | T | 0.108 | 0.000 | 0.008 | 0.000 |
| 591 | Exon7 | 47224 | | G | T | 0.167 | 0.033 | 0.133 | 0.017 |
| 630 | Exon7 | 47263 | | C | T | 0.117 | 0.000 | 0.000 | 0.008 |
| 1038 | 3'FR | 47671 | | C | T | 0.175 | 0.033 | 0.133 | 0.017 |
| 1080 | 3'FR | 47713 | | C | T | 0.000 | 0.008 | 0.000 | 0.008 |
| 1243 | 3'FR | 47876 | | A | G | 0.000 | 0.017 | 0.000 | 0.000 |
| 1343 | 3'FR | 47976 | | T | G | 0.125 | 0.000 | 0.000 | 0.000 |
| 1615 | 3'FR | 48248 | | C | T | 0.000 | 0.008 | 0.000 | 0.000 |
| 1649 | 3'FR | 48282 | | T | C | 0.000 | 0.000 | 0.000 | 0.008 |
| 1724 | 3'FR | 48357 | | C | T | 0.008 | 0.000 | 0.000 | 0.000 |

TABLE 3

Nucleotide diversity

| | $\pi \times 10^{-3}$* | $\theta \times 10^{-3}$ | Tajima's D | P value** |
|---|---|---|---|---|
| | GSTO2 | | | |
| AA | 1.30 ± 0.70 | 1.40 ± 0.40 | −0.37 | 0.72 |
| CA | 0.50 ± 0.30 | 0.40 ± 0.20 | 0.62 | 0.55 |
| HCA | 0.50 ± 0.30 | 0.60 ± 0.20 | −0.67 | 0.52 |
| MA | 0.50 ± 0.30 | 0.80 ± 0.30 | −1.30 | 0.20 |
| | Intergenic region | | | |
| AA | 3.80 ± 2.03 | 2.20 ± 0.73 | 1.94 | 0.05 |
| CA | 0.55 ± 0.44 | 0.25 ± 0.18 | 1.79 | 0.07 |
| HCA | 0.43 ± 0.37 | 0.25 ± 0.18 | 1.10 | 0.30 |
| MA | 0.66 ± 0.50 | 1.70 ± 0.60 | −1.65 | 0.10 |

*Values are parameter estimates mean ± SE.
**P values refer to Tajima's D.

Example 3

Linkage Disequilibrium Analysis and Haplotype Analysis

Linkage disequilibrium analysis was performed after all of the DNA samples had been genotyped at each of the polymorphic sites. Pairwise combinations of these polymorphisms were tested for linkage disequilibrium using the EH program developed by Terwilliger and Ott, supra. The output of this program was used to calculate d' values, a method for reporting linkage data that is independent of sample size. Pairwise combinations with a statistically significant linkage disequilibrium (P value <0.001) are shown in Table 4. D' values greater than 0 indicate a positive association, while d' values less than 0 indicate a negative association.

The genotype data also were used for haplotype analysis. Haplotypes typically are defined as combinations of alleles on a single chromosome, although they are sometimes referred to in a more restricted definition as all polymorphisms present on a single allele (Altshuler et al. *Nature* 437:1299-1320 (2005)). Haplotypes can be determined unequivocally if not more than one polymorphism per allele is heterozygous, but haplotypes also can be inferred computationally (Schaid, supra). GSTO2 haplotypes, both observed and inferred, with frequencies ≧0.08%, are listed in Tables 5-8. As shown in the tables, the identified haplotypes accounted for 88.9% of all DNA samples from Caucasian-American subjects, 80.8% of all DNA samples from African-American subjects, 95.0% of all DNA samples from Han Chinese-American subjects, and 90.9% of all DNA samples from Mexican-American subjects. A summary of haplotypes having frequencies ≧1% is presented in Table 9. Haplotypes including one or more cSNPs are included even if their frequency is less than 1%.

TABLE 4

Linkage disequilibrium statistics for GSTO2

| Location 1 | Location 2 | D' value | P value |
|---|---|---|---|
| African American Population | | | |
| 5'FR(−2012) | 5'FR(−1664) | 1 | 0 |
| 5'FR(−2012) | 5'FR(−1598) | 1 | 0 |
| 5'FR(−2012) | 5'FR(−1576) | 1 | 0 |
| 5'FR(−2012) | 5'FR(−1566) | 1 | 0 |
| 5'FR(−2012) | 5'FR(−1357) | 0.96 | 0 |
| 5'FR(−2012) | 5'FR(−1189) | 1 | 0 |
| 5'FR(−2012) | 5'FR(−1102) | 1 | 0 |
| 5'FR(−2012) | 5'FR(−1009) | 1 | 0 |
| 5'FR(−2012) | 5'FR(−781) | 0.96 | 0 |
| 5'FR(−2012) | 5'FR(−730) | 0.96 | 0 |
| 5'FR(−2012) | 5'FR(−637) | 0.96 | 0 |
| 5'FR(−2012) | 5'FR(−634) | 0.96 | 0 |
| 5'FR(−2012) | 5'FR(−530) | 0.96 | 0 |
| 5'FR(−2012) | 5'FR(−463) | 0.96 | 0 |
| 5'FR(−2012) | 5'FR(−450) | 0.96 | 0 |
| 5'FR(−2012) | Intron1(311) | 1 | 0 |
| 5'FR(−2012) | Intron6(−55) | 1 | 0 |
| 5'FR(−2012) | Intron6(−21) | 1 | 0 |
| 5'FR(−2012) | 3'FR(1343) | 0.77 | 0.0001 |
| 5'FR(−1785) | Exon1(−293) | 1 | 0 |
| 5'FR(−1785) | Intron1(426) | 1 | |
| 5'FR(−1785) | Intron1(−185) | 1 | 0 |
| 5'FR(−1785) | Exon7(630) | 1 | 0 |
| 5'FR(−1664) | 5'FR(−1598) | 1 | 0 |

TABLE 4-continued

Linkage disequilibrium statistics for GSTO2

| Location 1 | Location 2 | D' value | P value |
|---|---|---|---|
| 5'FR(−1664) | 5'FR(−1576) | 1 | 0 |
| 5'FR(−1664) | 5'FR(−1566) | 1 | 0 |
| 5'FR(−1664) | 5'FR(−1357) | 1 | 0 |
| 5'FR(−1664) | 5'FR(−1189) | 1 | 0 |
| 5'FR(−1664) | 5'FR(−1109) | 1 | 0 |
| 5'FR(−1664) | 5'FR(−781) | 1 | 0 |
| 5'FR(−1664) | 5'FR(−730) | 1 | 0 |
| 5'FR(−1664) | 5'FR(−637) | 1 | 0 |
| 5'FR(−1664) | 5'FR(−634) | 1 | 0 |
| 5'FR(−1664) | 5'FR(−530) | 1 | 0 |
| 5'FR(−1664) | 5'FR(−463) | 1 | 0 |
| 5'FR(−1664) | 5'FR(−450) | 1 | 0 |
| 5'FR(−1664) | Intron1(311) | 1 | 0 |
| 5'FR(−1664) | Intron1(2003) | 1 | 0 |
| 5'FR(−1664) | Intron6(−55) | 1 | 0.0001 |
| 5'FR(−1664) | Intron6(−21) | 1 | 0 |
| 5'FR(−1664) | 3'FR(1343) | 0.76 | 0.0001 |
| 5'FR(−1598) | 5'FR(−1576) | 1 | 0 |
| 5'FR(−1598) | 5'FR(−1566) | 1 | 0 |
| 5'FR(−1598) | 5'FR(−1357) | 1 | 0 |
| 5'FR(−1598) | 5'FR(−1189) | 1 | 0 |
| 5'FR(−1598) | 5'FR(−1009) | 1 | 0 |
| 5'FR(−1598) | 5'FR(−781) | 1 | 0 |
| 5'FR(−1598) | 5'FR(−730) | 1 | 0 |
| 5'FR(−1598) | 5'FR(−637) | 1 | 0 |
| 5'FR(−1598) | 5'FR(−634) | 1 | 0 |
| 5'FR(−1598) | 5'FR(−530) | 1 | 0 |
| 5'FR(−1598) | 5'FR(−463) | 1 | 0 |
| 5'FR(−1598) | 5'FR(−450) | 1 | 0 |
| 5'FR(−1598) | Intron1(311) | 1 | 0 |
| 5'FR(−1598) | Intron1(2003) | 1 | 0 |
| 5'FR(−1598) | Exon5(424) | 1 | 0 |
| 5'FR(−1598) | Intron5(74) | 1 | 0 |
| 5'FR(−1598) | Intron6(−21) | 1 | 0 |
| 5'FR(−1598) | 3'FR(1343) | 0.76 | 0.0001 |
| 5'FR(−1576) | 5'FR(1566) | 1 | 0 |
| 5'FR(−1576) | 5'FR(1357) | 1 | 0 |
| 5'FR(−1576) | 5'FR(1189) | 1 | 0 |
| 5'FR(−1576) | 5'FR(1009) | 1 | 0 |
| 5'FR(−1576) | 5'FR(−781) | 1 | 0 |
| 5'FR(−1576) | 5'FR(−730) | 1 | 0 |
| 5'FR(−1576) | 5'FR(−637) | 1 | 0 |
| 5'FR(−1576) | 5'FR(−634) | 1 | 0 |
| 5'FR(−1576) | 5'FR(−530) | 1 | 0 |
| 5'FR(−1576) | 5'FR(−463) | 1 | 0 |
| 5'FR(−1576) | 5'FR(−450) | 1 | 0 |
| 5'FR(−1576) | Intron1(311) | 1 | 0 |
| 5'FR(−1576) | Intron1(2003) | 1 | 0 |
| 5'FR(−1576) | Intron6(−55) | 1 | 0.0001 |
| 5'FR(−1576) | Intron6(−21) | 1 | 0 |
| 5'FR(−1576) | 3'FR(1343) | 0.76 | 0.0001 |
| 5'FR(−1566) | 5'FR(−1357) | 1 | 0 |
| 5'FR(−1566) | 5'FR(−1189) | 1 | 0 |
| 5'FR(−1566) | 5'FR(−1009) | 1 | 0 |
| 5'FR(−1566) | 5'FR(−781) | 0.96 | 0 |
| 5'FR(−1566) | 5'FR(−730) | 0.96 | 0 |
| 5'FR(−1566) | 5'FR(−637) | 0.96 | 0 |
| 5'FR(−1566) | 5'FR(−634) | 0.96 | 0 |
| 5'FR(−1566) | Exon1(−530) | 0.96 | 0 |
| 5'FR(−1566) | Exon1(−463) | 0.96 | 0 |
| 5'FR(−1566) | Exon1(−450) | 0.96 | 0 |
| 5'FR(−1566) | Intron1(311) | 1 | 0 |
| 5'FR(−1566) | Intron1(2003) | 1 | 0 |
| 5'FR(−1566) | Intron6(−21) | 0.87 | 0 |
| 5'FR(−1566) | 3'FR(1343) | 0.65 | 0.0004 |
| 5'FR(−1541) | Exon1(−410) | 1 | 0 |
| 5'FR(−1357) | 5'FR(−1189) | 1 | 0 |
| 5'FR(−1357) | 5'FR(−1009) | 1 | 0 |
| 5'FR(−1357) | 5'FR(−781) | 1 | 0 |
| 5'FR(−1357) | 5'FR(−730) | 1 | 0 |
| 5'FR(−1357) | 5'FR(−637) | 1 | 0 |
| 5'FR(−1357) | 5'FR(−634) | 1 | 0 |
| 5'FR(−1357) | Exon1(−530) | 1 | 0 |
| 5'FR(−1357) | Exon1(−463) | 1 | 0 |
| 5'FR(−1357) | Intron1(311) | 1 | 0 |
| 5'FR(−1357) | Intron1(2003) | 1 | 0 |
| 5'FR(−1357) | Intron6(−55) | 1 | 0.0001 |
| 5'FR(−1357) | Intron6(−21) | 1 | 0 |
| 5'FR(−1357) | 3'FR(1343) | 0.76 | 0.0001 |
| 5'FR(−1189) | 5'FR(−1009) | 1 | 0 |
| 5'FR(−1189) | 5'FR(−781) | 1 | 0 |
| 5'FR(−1189) | 5'FR(−730) | 1 | 0 |
| 5'FR(−1189) | 5'FR(−637) | 1 | 0 |
| 5'FR(−1189) | 5'FR(−634) | 1 | 0 |
| 5'FR(−1189) | Exon1(−530) | 1 | 0 |
| 5'FR(−1189) | Exon1(−463) | 1 | 0 |
| 5'FR(−1189) | Exon1(−450) | 1 | 0 |
| 5'FR(−1189) | Intron1(311) | 1 | 0 |
| 5'FR(−1189) | Intron1(2003) | 1 | 0 |
| 5'FR(−1189) | Intron6(−55) | 1 | 0.0001 |
| 5'FR(−1189) | Intron6(−21) | 1 | 0 |
| 5'FR(−1189) | 3'FR(1343) | 0.76 | 0.0001 |
| 5'FR(−1105) | Exon2(−183) | 1 | 0 |
| 5'FR(−1102) | Intron4(20) | 1 | 0 |
| 5'FR(−1102) | Exon5(424) | 1 | 0 |
| 5'FR(−1102) | Intron5(74) | 1 | 0 |
| 5'FR(−1009) | 5'FR(−781) | 1 | 0 |
| 5'FR(−1009) | 5'FR(−730) | 1 | 0 |
| 5'FR(−1009) | 5'FR(−637) | 1 | 0 |
| 5'FR(−1009) | 5'FR(−634) | 1 | 0 |
| 5'FR(−1009) | Exon1(530) | 1 | 0 |
| 5'FR(−1009) | Exon1(463) | 1 | 0 |
| 5'FR(−1009) | Exon1(450) | 1 | 0 |
| 5'FR(−1009) | Intron1(311) | 1 | 0 |
| 5'FR(−1009) | Intron1(2003) | 1 | 0 |
| 5'FR(−1009) | Intron6(−55) | 1 | 0.0001 |
| 5'FR(−1009) | Intron6(−21) | 1 | 0 |
| 5'FR(−1009) | 3'FR(1343) | 0.76 | 0.0001 |
| 5'FR(−781) | 5'FR(−730) | 1 | 0 |
| 5'FR(−781) | 5'FR(−637) | 1 | 0 |
| 5'FR(−781) | 5'FR(−634) | 1 | 0 |
| 5'FR(−781) | Exon1(−530) | 1 | 0 |
| 5'FR(−781) | Exon1(−463) | 1 | 0 |
| 5'FR(−781) | Exon1(−450) | 1 | 0 |
| 5'FR(−781) | Intron1(311) | 1 | 0 |
| 5'FR(−781) | Intron1(2003) | 1 | 0 |
| 5'FR(−781) | Intron6(−21) | 0.87 | 0 |
| 5'FR(−730) | 5'FR(−637) | 1 | 0 |
| 5'FR(−730) | 5'FR(−634) | 1 | 0 |
| 5'FR(−730) | Exon1(−530) | 1 | 0 |
| 5'FR(−730) | Exon1(−463) | 1 | 0 |
| 5'FR(−730) | Exon1(−450) | 1 | 0 |
| 5'FR(−730) | Intron1(311) | 1 | 0 |
| 5'FR(−730) | Intron1(2003) | 1 | 0 |
| 5'FR(−730) | Intron6(−21) | 0.87 | 0 |
| 5'FR(637) | 5'FR(634) | 1 | 0 |
| 5'FR(637) | Exon1(−530) | 1 | 0 |
| 5'FR(637) | Exon1(−463) | 1 | 0 |
| 5'FR(637) | Exon1(−450) | 1 | 0 |
| 5'FR(637) | Intron1(311) | 1 | 0 |
| 5'FR(637) | Intron1(2003) | 1 | 0 |
| 5'FR(637) | Intron6(−21) | 0.87 | 0 |
| 5'FR(634) | Exon1(−530) | 1 | 0 |
| 5'FR(634) | Exon1(−463) | 1 | 0 |
| 5'FR(634) | Exon1(−450) | 1 | 0 |
| 5'FR(634) | Intron1(311) | 1 | 0 |
| 5'FR(634) | Intron1(2003) | 1 | 0 |
| 5'FR(634) | Intron6(−21) | 0.87 | 0 |
| 5'FR(530) | Exon1(−463) | 1 | 0 |
| 5'FR(530) | Exon1(−450) | 1 | 0 |
| 5'FR(530) | Intron1(2003) | 1 | 0 |
| 5'FR(530) | Intron6(−21) | 0.87 | 0 |
| Exon1(−463) | Exon1(−450) | 1 | 0 |
| Exon1(−463) | Intron1(311) | 1 | 0 |
| Exon1(−463) | Intron1(2003) | 1 | 0 |
| Exon1(−463) | Intron6(−21) | 0.87 | 0 |
| Exon1(−450) | Intron1(311) | 1 | 0 |
| Exon1(−450) | Intron1(2003) | 1 | 0 |

TABLE 4-continued

Linkage disequilibrium statistics for GSTO2

| Location 1 | Location 2 | D' value | P value |
|---|---|---|---|
| Exon1(−450) | Intron6(−21) | 0.87 | 0 |
| Exon1(−293) | Intron1(426) | 1 | 0 |
| Exon1(−293) | Intron1(−185) | 1 | 0 |
| Exon1(−293) | Exon7(630) | 1 | 0 |
| Intron1(52) | Intron1(310) | 1 | 0 |
| Intron1(52) | Intron1(−12) | 1 | 0 |
| Intron1(152) | Intron6(−55) | 1 | 0 |
| Intron1(310) | Intron1(−12) | 1 | 0 |
| Intron1(311) | Intron1(2003) | 1 | 0 |
| Intron1(311) | Intron6(−21) | 1 | 0 |
| Intron1(402) | Intron1(−1131) | 1 | 0 |
| Intron1(426) | Intron1(−185) | 1 | 0 |
| Intron1(426) | Exon7(630) | 1 | 0 |
| Intron1(1694) | Exon7(630) | 1 | 0 |
| Intron1(2003) | Intron6(−55) | 1 | 0.0001 |
| Intron1(2003) | Intron6(−21) | 1 | 0 |
| Intron1(2003) | 3'FR(1343) | 0.76 | 0.0001 |
| Intron1(2168) | Exon7(591) | 0.59 | 0 |
| Intron1(2168) | 3'FR(1038) | 0.61 | 0 |
| Intron1(−185) | Exon7(630) | 0.82 | 0 |
| Intron4(20) | Exon5(424) | 1 | 0 |
| Intron4(20) | Intron5(74) | 1 | 0 |
| Exon5(424) | Intron5(74) | 1 | 0 |
| Intron6(−55) | Intron6(−21) | 1 | 0 |
| Intron6(−55) | 3'FR(1343) | 1 | 0 |
| Intron6(−21) | 3'FR(1343) | 1 | 0 |
| Exon7(591) | 3'FR(1038) | 1 | 0 |
| Mexican American Population | | | |
| 5'FR(−2012) | 5'FR(−1664) | 1 | 0 |
| 5'FR(−2012) | 5'FR(−1598) | 1 | 0 |
| 5'FR(−2012) | 5'FR(−1576) | 1 | 0 |
| 5'FR(−2012) | 5'FR(−1566) | 1 | 0 |
| 5'FR(−2012) | 5'FR(−1357) | 1 | 0 |
| 5'FR(−2012) | 5'FR(−1189) | 1 | 0 |
| 5'FR(−2012) | 5'FR(−1009) | 1 | 0 |
| 5'FR(−2012) | 5'FR(−781) | 1 | 0 |
| 5'FR(−2012) | 5'FR(−730) | 1 | 0 |
| 5'FR(−2012) | 5'FR(−637) | 1 | 0 |
| 5'FR(−2012) | 5'FR(−634) | 1 | 0 |
| 5'FR(−2012) | Exon1(−530) | 1 | 0 |
| 5'FR(−2012) | Exon1(−463) | 1 | 0 |
| 5'FR(−2012) | Exon1(−450) | 1 | 0 |
| 5'FR(−2012) | Intron1(311) | 1 | 0 |
| 5'FR(−2012) | Intron1(2003) | 1 | 0 |
| 5'FR(−2012) | 3'FR(1649) | 1 | 0 |
| 5'FR(−1664) | 5'FR(1598) | 1 | 0 |
| 5'FR(−1664) | 5'FR(1576) | 1 | 0 |
| 5'FR(−1664) | 5'FR(1566) | 1 | 0 |
| 5'FR(−1664) | 5'FR(1357) | 1 | 0 |
| 5'FR(−1664) | 5'FR(1189) | 1 | 0 |
| 5'FR(−1664) | 5'FR(1009) | 1 | 0 |
| 5'FR(−1664) | 5'FR(781) | 1 | 0 |
| 5'FR(−1664) | 5'FR(730) | 1 | 0 |
| 5'FR(−1664) | 5'FR(637) | 1 | 0 |
| 5'FR(−1664) | 5'FR(634) | 1 | 0 |
| 5'FR(−1664) | Exon1(−530) | 1 | 0 |
| 5'FR(−1664) | Exon1(−463) | 1 | 0 |
| 5'FR(−1664) | Exon1(−450) | 1 | 0 |
| 5'FR(−1664) | Intron1(311) | 1 | 0 |
| 5'FR(−1664) | Intron1(2003) | 1 | 0 |
| 5'FR(−1664) | 3'FR(1649) | 1 | 0 |
| 5'FR(−1598) | 5'FR(−1576) | 1 | 0 |
| 5'FR(−1598) | 5'FR(−1566) | 1 | 0 |
| 5'FR(−1598) | 5'FR(−1357) | 1 | 0 |
| 5'FR(−1598) | 5'FR(−1189) | 1 | 0 |
| 5'FR(−1598) | 5'FR(−1009) | 1 | 0 |
| 5'FR(−1598) | 5'FR(−781) | 1 | 0 |
| 5'FR(−1598) | 5'FR(−730) | 1 | 0 |
| 5'FR(−1598) | 5'FR(−637) | 1 | 0 |
| 5'FR(−1598) | 5'FR(−634) | 1 | 0 |
| 5'FR(−1598) | Exon1(−530) | 1 | 0 |
| 5'FR(−1598) | Exon1(−463) | 1 | 0 |
| 5'FR(−1598) | Exon1(−450) | 1 | 0 |
| 5'FR(−1598) | Intron1(311) | 1 | 0 |
| 5'FR(−1598) | Intron1(2003) | 1 | 0 |
| 5'FR(−1598) | 3'FR(1649) | 1 | 0 |
| 5'FR(−1576) | 5'FR(−1566) | 1 | 0 |
| 5'FR(−1576) | 5'FR(−1357) | 1 | 0 |
| 5'FR(−1576) | 5'FR(−1189) | 1 | 0 |
| 5'FR(−1576) | 5'FR(−1009) | 1 | 0 |
| 5'FR(−1576) | 5'FR(−781) | 1 | 0 |
| 5'FR(−1576) | 5'FR(−730) | 1 | 0 |
| 5'FR(−1576) | 5'FR(−637) | 1 | 0 |
| 5'FR(−1576) | 5'FR(−634) | 1 | 0 |
| 5'FR(−1576) | Exon1(−530) | 1 | 0 |
| 5'FR(−1576) | Exon1(−463) | 1 | 0 |
| 5'FR(−1576) | Exon1(−450) | 1 | 0 |
| 5'FR(−1576) | Intron1(311) | 1 | 0 |
| 5'FR(−1576) | Intron1(2003) | 1 | 0 |
| 5'FR(−1576) | 3'FR(1649) | 1 | 0 |
| 5'FR(−1566) | 5'FR(−1357) | 1 | 0 |
| 5'FR(−1566) | 5'FR(−1189) | 1 | 0 |
| 5'FR(−1566) | 5'FR(−1009) | 1 | 0 |
| 5'FR(−1566) | 5'FR(−781) | 1 | 0 |
| 5'FR(−1566) | 5'FR(−730) | 1 | 0 |
| 5'FR(−1566) | 5'FR(−637) | 1 | 0 |
| 5'FR(−1566) | 5'FR(−634) | 1 | 0 |
| 5'FR(−1566) | Exon1(−530) | 1 | 0 |
| 5'FR(−1566) | Exon1(−463) | 1 | 0 |
| 5'FR(−1566) | Exon1(−450) | 1 | 0 |
| 5'FR(−1566) | Intron1(311) | 1 | 0 |
| 5'FR(−1566) | Intron1(2003) | 1 | 0 |
| 5'FR(−1566) | 3'FR(1649) | 1 | 0 |
| 5'FR(−1357) | 5'FR(−1189) | 1 | 0 |
| 5'FR(−1357) | 5'FR(−1109) | 1 | 0 |
| 5'FR(−1357) | 5'FR(−781) | 1 | 0 |
| 5'FR(−1357) | 5'FR(−730) | 1 | 0 |
| 5'FR(−1357) | 5'FR(−637) | 1 | 0 |
| 5'FR(−1357) | 5'FR(−634) | 1 | 0 |
| 5'FR(−1357) | Exon1(−530) | 1 | 0 |
| 5'FR(−1357) | Exon1(−463) | 1 | 0 |
| 5'FR(−1357) | Exon1(−450) | 1 | 0 |
| 5'FR(−1357) | Intron1(311) | 1 | 0 |
| 5'FR(−1357) | Intron1(2003) | 1 | 0 |
| 5'FR(−1357) | 3'FR(1649) | 1 | 0 |
| 5'FR(−1189) | 5'FR(−1009) | 1 | 0 |
| 5'FR(−1189) | 5'FR(−781) | 1 | 0 |
| 5'FR(−1189) | 5'FR(−730) | 1 | 0 |
| 5'FR(−1189) | 5'FR(−637) | 1 | 0 |
| 5'FR(−1189) | 5'FR(−634) | 1 | 0 |
| 5'FR(−1189) | Exon1(−530) | 1 | 0 |
| 5'FR(−1189) | Exon1(−463) | 1 | 0 |
| 5'FR(−1189) | Exon1(−450) | 1 | 0 |
| 5'FR(−1189) | Intron1(311) | 1 | 0 |
| 5'FR(−1189) | Intron1(2003) | 1 | 0 |
| 5'FR(−1189) | 3'FR(1649) | 1 | 0 |
| 5'FR(−1105) | 5'FR(−1102) | 1 | 0 |
| 5'FR(−1105) | Exon2(−183) | 1 | 0 |
| 5'FR(−1105) | Intron4(20) | 0.76 | 0 |
| 5'FR(−1105) | Exon5(424) | 0.75 | 0 |
| 5'FR(−1105) | Intron5(74) | 0.75 | 0 |
| 5'FR(−1102) | Exon2(−183) | 1 | 0 |
| 5'FR(−1102) | Intron4(20) | 0.78 | 0 |
| 5'FR(−1102) | Exon5(424) | 1 | 0 |
| 5'FR(−1102) | Intron5(74) | 1 | 0 |
| 5'FR(−1009) | 5'FR(−781) | 1 | 0 |
| 5'FR(−1009) | 5'FR(−730) | 1 | 0 |
| 5'FR(−1009) | 5'FR(−637) | 1 | 0 |
| 5'FR(−1009) | 5'FR(−634) | 1 | 0 |
| 5'FR(−1009) | Exon1(−530) | 1 | 0 |
| 5'FR(−1009) | Exon1(−463) | 1 | 0 |
| 5'FR(−1009) | Exon1(−450) | 1 | 0 |
| 5'FR(−1009) | Intron1(311) | 1 | 0 |
| 5'FR(−1009) | Intron1(2003) | 1 | 0 |
| 5'FR(−1009) | 3'FR(1649) | 1 | 0 |
| 5'FR(−781) | 5'FR(−730) | 1 | 0 |
| 5'FR(−781) | 5'FR(−637) | 1 | 0 |

TABLE 4-continued

Linkage disequilibrium statistics for GSTO2

| Location 1 | Location 2 | D' value | P value |
|---|---|---|---|
| 5'FR(−781) | 5'FR(−634) | 1 | 0 |
| 5'FR(−781) | Exon1(−530) | 1 | 0 |
| 5'FR(−781) | Exon1(−463) | 1 | 0 |
| 5'FR(−781) | Exon1(−450) | 1 | 0 |
| 5'FR(−781) | Intron1(311) | 1 | 0 |
| 5'FR(−781) | Intron1(2003) | 1 | 0 |
| 5'FR(−781) | 3'FR(1649) | 1 | 0 |
| 5'FR(−730) | 5'FR(−637) | 1 | 0 |
| 5'FR(−730) | 5'FR(−634) | 1 | 0 |
| 5'FR(−730) | Exon1(−530) | 1 | 0 |
| 5'FR(−730) | Exon1(−463) | 1 | 0 |
| 5'FR(−730) | Exon1(−450) | 1 | 0 |
| 5'FR(−730) | Intron1(311) | 1 | 0 |
| 5'FR(−730) | Intron1(2003) | 1 | 0 |
| 5'FR(−730) | 3'FR(1649) | 1 | 0 |
| 5'FR(−637) | 5'FR(−634) | 1 | 0 |
| 5'FR(−637) | Exon1(−530) | 1 | 0 |
| 5'FR(−637) | Exon1(−463) | 1 | 0 |
| 5'FR(−637) | Exon1(−450) | 1 | 0 |
| 5'FR(−637) | Intron1(311) | 1 | 0 |
| 5'FR(−637) | Intron1(2003) | 1 | 0 |
| 5'FR(−637) | 3'FR(1649) | 1 | 0 |
| 5'FR(−634) | Exon1(−530) | 1 | 0 |
| 5'FR(−634) | Exon1(−463) | 1 | 0 |
| 5'FR(−634) | Exon1(−450) | 1 | 0 |
| 5'FR(−634) | Intron1(311) | 1 | 0 |
| 5'FR(−634) | Intron1(2003) | 1 | 0 |
| 5'FR(−634) | 3'FR(1649) | 1 | 0 |
| Exon1(−530) | Exon1(−463) | 1 | 0 |
| Exon1(−530) | Exon1(−450) | 1 | 0 |
| Exon1(−530) | Intron1(311) | 1 | 0 |
| Exon1(−530) | Intron1(2003) | 1 | 0 |
| Exon1(−530) | 3'FR(1649) | 1 | 0 |
| Exon1(−463) | Exon1(−450) | 1 | 0 |
| Exon1(−463) | Intron1(311) | 1 | 0 |
| Exon1(−463) | Intron1(2003) | 1 | 0 |
| Exon1(−463) | 3'FR(1649) | 1 | 0 |
| Exon1(−450) | Intron1(311) | 1 | 0 |
| Exon1(−450) | Intron1(2003) | 1 | 0 |
| Exon1(−450) | 3'FR(1649) | 1 | 0 |
| Intron1(311) | Intron1(2003) | 1 | 0 |
| Intron1(311) | 3'FR(1649) | 1 | 0 |
| Intron1(402) | Intron1(−1131) | 1 | 0 |
| Intron1(402) | Intron1(−38) | 1 | 0 |
| Intron1(1694) | Exon7(630) | 1 | 0 |
| Intron1(2003) | 3'FR(1649) | 1 | 0 |
| Intron1(2168) | Exon7(591) | 0.49 | 0.0002 |
| Intron1(2168) | 3'FR(1038) | 0.49 | 0.0002 |
| Intron1(1131) | Intron4(−38) | 1 | 0 |
| Exon2(−183) | Intron(20) | 1 | 0 |
| Exon2(−183) | Exon5(424) | 1 | 0 |
| Exon2(−183) | Intron5(74) | 1 | 0 |
| Intron4(20) | Exon5(424) | 1 | 0 |
| Intron4(20) | Intron5(74) | 1 | 0 |
| Exon5(424) | Intron5(74) | 1 | 0 |
| Exon7(591) | 3'FR(1038) | 1 | 0 |
| Caucasian American Population | | | |
| 5'FR(−2012) | Intron1(2146) | 0.49 | 0.0002 |
| 5'FR(−1105) | 5'FR(−1102) | 1 | 0 |
| 5'FR(−1105) | Exon2(−183) | 0.9 | 0 |
| 5'FR(−1105) | Intron4(20) | 0.79 | 0 |
| 5'FR(−1105) | Exon5(424) | 0.8 | 0 |
| 5'FR(−1105) | Intron5(74) | 0.8 | 0 |
| 5'FR(−1102) | Intron1(402) | 0.85 | 0.0001 |
| 5'FR(−1102) | Intron1(−1131) | 0.85 | 0.0001 |
| 5'FR(−1102) | Exon2(−183) | 0.89 | 0 |
| 5'FR(−1102) | Intron4(20) | 0.77 | 0.0002 |
| 5'FR(−1102) | Intron4(−38) | 0.78 | 0 |
| 5'FR(−1102) | Exon5(424) | 0.82 | 0 |
| 5'FR(−1102) | Intron5(74) | 0.82 | 0 |
| Exon1(−526) | Exon7(591) | 1 | 0.0002 |
| Intron1(402) | Intron1(−1131) | 1 | 0 |
| Intron1(402) | Intron4(−38) | 1 | 0 |
| Intron1(477) | Exon7(591) | 0.74 | 0 |
| Intron1(477) | 3'FR(1038) | 1 | 0 |
| Intron1(477) | 3'FR(1243) | 1 | 0 |
| Intron1(−1131) | Intron4(−38) | 1 | 0 |
| Exon2(−183) | Intron4(20) | 1 | 0 |
| Exon2(−183) | Exon5(424) | 1 | 0 |
| Exon2(−183) | Intron5(74) | 1 | 0 |
| Intron4(20) | Exon5(424) | 1 | 0 |
| Intron4(20) | Intron5(74) | 1 | 0 |
| Exon5(424) | Intron5(74) | 1 | 0 |
| Exon7(591) | 3'FR(1038) | 0.74 | 0 |
| Han Chinese American Population | | | |
| 5'FR(−1105) | 5'FR(−1102) | 1 | 0 |
| 5'FR(−1105) | Exon2(−183) | 1 | 0 |
| 5'FR(−1105) | Exon2(424) | 0.86 | 0 |
| 5'FR(−1105) | Intron5(74) | 0.86 | 0 |
| 5'FR(−1102) | Exon2(−183) | 1 | 0 |
| 5'FR(−1102) | Intron5(20) | 0.8 | 0 |
| 5'FR(−1102) | Exon5(424) | 0.95 | 0 |
| 5'FR(−1102) | Intron5(74) | 0.95 | 0 |
| Exon1(−625) | Intron1(477) | 0.95 | 0 |
| Intron1(402) | Intron1(−1131) | 1 | 0 |
| Intron1(477) | 3'FR(1038) | 1 | 1E−04 |
| Exon2(−183) | Exon5(424) | 1 | 0 |
| Exon2(−183) | Intron5(74) | 1 | 0 |
| Intron4(20) | Exon5(424) | 1 | 0 |
| Intron4(20) | Intron5(74) | 1 | 0 |
| Exon5(424) | Intron5(74) | 1 | 0 |
| Intron6(−55) | Intron6(−21) | 1 | 0 |
| Exon7(591) | 3'FR(1038) | 0.93 | 0 |

TABLE 5

GSTO2 Haplotypes for Caucasian-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 50.06% | o | D | T | G | C | C | G | G | C | C | T | G | G | G |
| 21.60% | o | D | T | G | C | C | G | G | C | C | T | G | A | T |
| 9.92% | o | D | T | G | C | C | G | G | C | C | T | C | G | G |
| 3.14% | i | D | T | G | C | C | G | G | C | C | T | G | A | T |
| 1.67% | i | D | T | G | C | C | G | G | C | C | T | G | G | G |
| 1.67% | i | D | T | G | C | C | G | G | C | C | T | G | G | T |
| 0.83% | i | D | T | G | C | C | G | G | C | C | T | G | G | T |

TABLE 5-continued

GSTO2 Haplotypes for Caucasian-American Population

| 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) | Intron1 (+52) |
|---|---|---|---|---|---|---|---|---|---|---|---|---|---|---|
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |

| Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) | Intron1 (−185) | Intron1 (−19) |
|---|---|---|---|---|---|---|---|---|---|---|---|---|---|---|
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | C | T | T | I | A | A | A | G | C | A | T |
| G | I | G | T | T | T | T | D | A | A | A | G | T | A | T |

| Intron1 (−12) | Exon2 (−183) | Intron2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) | Intron6 (−55) | Intron6 (−21) | Exon7 (+591) |
|---|---|---|---|---|---|---|---|---|---|---|---|---|---|---|
| G | A | C | G | T | C | A | G | A | A | T | C | C | C | G |
| G | G | C | G | C | C | A | G | G | G | T | C | C | C | G |
| G | A | C | G | C | C | A | G | A | A | T | C | C | C | G |
| G | A | C | G | T | C | A | G | A | A | T | C | C | C | G |
| G | A | C | G | C | C | A | G | G | G | T | C | C | C | G |
| G | A | C | G | C | C | A | G | G | G | T | C | C | C | T |
| G | A | C | G | C | C | A | G | G | G | T | C | C | C | G |

| Exon7 (+630) | 3'FR (+1038) | 3'FR (+1080) | 3'FR (+1243) | 3'FR (+1343) | 3'FR (+1615) | 3'FR (+1649) | 3'FR (+1724) |
|---|---|---|---|---|---|---|---|
| C | C | C | A | T | C | T | C |
| C | C | C | A | T | C | T | C |
| C | C | C | A | T | C | T | C |
| C | C | C | A | T | C | T | C |
| C | C | C | A | T | C | T | C |
| C | T | C | G | T | C | T | C |
| C | C | C | A | T | C | T | C |

*o = observed; i = inferred

TABLE 6

GSTO2 Haplotypes for African-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 16.70% | i | I | T | G | T | G | C | A | C | A | C | G | G | C |
| 14.30% | i | D | T | G | C | C | G | G | C | C | T | G | G | T |
| 14.20% | o | D | T | G | C | C | G | G | C | C | T | G | G | G |
| 6.53% | i | D | T | G | C | C | G | G | C | C | T | G | A | T |
| 5.00% | i | D | T | G | C | C | G | G | C | C | T | G | G | T |
| 4.17% | i | D | T | G | C | C | G | G | C | C | T | G | G | T |
| 3.33% | i | D | C | G | C | C | G | G | C | C | T | G | G | T |
| 3.33% | i | D | T | G | C | C | G | G | C | C | T | G | G | G |
| 3.33% | i | D | T | G | C | C | G | G | C | C | T | G | G | T |
| 2.50% | o | D | T | G | C | C | G | G | C | C | T | G | G | G |
| 2.50% | i | I | T | G | T | G | C | A | C | A | C | G | G | T |
| 1.67% | i | D | C | G | C | C | G | G | C | C | T | G | G | T |
| 1.67% | i | D | T | G | C | C | G | G | C | C | T | G | G | T |
| 1.53% | i | D | T | G | C | C | G | G | C | C | T | G | G | T |

| 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) | Intron1 (+52) |
|---|---|---|---|---|---|---|---|---|---|---|---|---|---|---|
| T | C | I | T | G | A | G | C | A | C | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |

TABLE 6-continued

GSTO2 Haplotypes for African-American Population

| | | | | | | | | | | | | | | |
|---|---|---|---|---|---|---|---|---|---|---|---|---|---|---|
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | T | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| T | C | I | T | G | A | G | C | A | C | G | T | A | C | A |
| C | A | D | C | C | A | C | C | G | A | G | T | T | C | A |
| C | A | D | C | C | A | C | C | G | A | G | T | A | C | A |
| C | A | D | C | C | A | C | C | G | A | G | T | A | C | A |

| Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) | Intron1 (−185) | Intron1 (−19) |
|---|---|---|---|---|---|---|---|---|---|---|---|---|---|---|
| G | I | A | T | C | T | T | D | A | G | A | G | C | A | T |
| G | I | G | T | C | T | T | D | A | A | A | A | C | A | T |
| G | I | G | T | C | T | T | D | A | A | A | G | C | A | T |
| G | I | G | T | C | T | T | D | A | A | A | G | C | A | T |
| G | I | G | T | C | T | T | D | G | A | A | G | C | A | T |
| G | I | G | T | C | C | T | D | A | A | A | G | C | G | T |
| G | I | G | T | C | T | T | D | A | A | A | G | C | A | T |
| G | I | G | T | T | T | T | D | A | A | A | G | T | A | T |
| G | I | G | T | C | T | T | D | A | A | A | G | C | A | T |
| G | I | A | T | C | T | T | D | A | G | A | G | C | A | T |
| G | I | G | T | C | C | T | D | A | A | A | G | C | G | T |
| G | I | G | T | C | T | A | D | A | A | A | A | C | A | T |
| G | I | G | T | C | T | T | D | A | A | A | A | C | A | T |

| Intron1 (−12) | Exon2 (−183) | Intron2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) | Intron6 (−55) | Intron6 (−21) | Exon7 (+591) |
|---|---|---|---|---|---|---|---|---|---|---|---|---|---|---|
| G | A | C | G | C | C | A | G | G | G | T | C | C | C | G |
| G | A | C | G | C | C | A | G | G | G | T | C | C | C | G |
| G | A | C | G | T | C | A | G | A | A | T | C | C | C | G |
| G | G | C | G | C | C | A | G | G | G | T | C | C | C | G |
| G | A | C | G | C | C | A | G | G | G | T | C | C | C | G |
| G | A | C | G | C | C | A | G | G | G | T | C | C | C | G |
| G | A | C | G | C | C | A | G | G | G | T | C | C | C | G |
| G | A | C | G | T | C | A | G | A | A | T | C | C | C | T |
| G | A | C | G | C | C | A | G | G | G | T | C | C | C | G |
| G | A | C | G | C | C | A | G | A | A | T | C | C | C | G |
| G | A | C | G | C | C | A | G | G | G | T | C | C | T | G |
| G | A | C | G | C | C | A | G | G | G | T | C | C | C | T |
| G | A | C | G | C | C | A | G | G | G | T | C | C | C | T |
| G | A | C | G | C | C | A | G | G | G | T | C | C | C | G |

| Exon7 (+630) | 3'FR (+1038) | 3'FR (+1080) | 3'FR (+1243) | 3'FR (+1343) | 3'FR (+1615) | 3'FR (+1649) | 3'FR (+1724) |
|---|---|---|---|---|---|---|---|
| C | C | C | A | T | C | T | C |
| C | C | C | A | T | C | T | C |
| C | C | C | A | T | C | T | C |
| C | C | C | A | T | C | T | C |
| C | C | C | A | T | C | T | C |
| T | C | C | A | T | C | T | C |
| T | C | C | A | T | C | T | C |
| C | T | C | A | T | C | T | C |
| C | C | C | A | T | C | T | C |
| C | C | C | A | T | C | T | C |
| C | C | C | A | G | C | T | C |
| T | T | C | A | T | C | T | C |
| C | T | C | A | T | C | T | C |
| C | T | C | A | G | C | T | C |

*o = observed; i = inferred

TABLE 7

GSTO2 Haplotypes for Han Chinese-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 55.20% | o | D | T | G | C | C | G | G | C | C | T | G | G | G |
| 13.30% | o | D | T | G | C | C | G | G | C | C | T | G | A | T |
| 12.30% | o | D | T | G | C | C | G | G | C | C | T | G | G | G |
| 6.43% | o | D | T | G | C | C | G | G | C | C | T | G | G | G |
| 1.67% | i | D | T | G | C | C | G | G | C | C | T | G | A | T |
| 1.67% | o | D | T | G | C | C | G | G | C | C | T | G | A | T |
| 1.67% | i | D | T | G | C | C | G | G | C | C | T | G | G | T |
| 1.67% | i | D | T | G | C | C | G | G | C | C | T | G | G | T |
| 1.07% | i | D | T | G | C | C | G | G | C | C | T | G | G | G |

| 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) | Intron1 (+52) |
|---|---|---|---|---|---|---|---|---|---|---|---|---|---|---|
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |

| Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) | Intron1 (−185) | Intron1 (−19) |
|---|---|---|---|---|---|---|---|---|---|---|---|---|---|---|
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | C | T | T | D | A | A | A | A | C | A | T |
| G | I | G | T | C | T | T | I | A | A | A | G | C | A | T |
| G | I | G | T | C | T | T | D | A | A | A | G | C | A | T |

| Intron1 (−12) | Exon2 (−183) | Intron2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) | Intron6 (−55) | Intron6 (−21) | Exon7 (+591) |
|---|---|---|---|---|---|---|---|---|---|---|---|---|---|---|
| G | A | C | G | T | C | A | G | A | A | T | C | C | C | G |
| G | G | C | G | C | C | A | G | G | G | T | C | C | C | G |
| G | A | C | G | C | C | A | G | A | A | T | C | C | C | G |
| G | A | C | G | T | C | A | G | A | A | T | C | C | C | T |
| G | G | C | G | C | C | A | A | G | G | T | C | C | C | G |
| G | G | C | G | T | C | A | G | A | A | T | C | C | C | G |
| G | A | C | G | C | C | A | G | G | G | T | C | C | C | T |
| G | A | C | G | C | C | A | G | G | G | T | C | C | C | T |
| G | A | C | G | C | C | A | G | A | A | T | C | C | C | T |

| Exon7 (+630) | 3'FR (+1038) | 3'FR (+1080) | 3'FR (+1243) | 3'FR (+1343) | 3'FR (+1615) | 3'FR (+1649) | 3'FR (+1724) |
|---|---|---|---|---|---|---|---|
| C | C | C | A | T | C | T | C |
| C | C | C | A | T | C | T | C |
| C | C | C | A | T | C | T | C |
| C | T | C | A | T | C | T | C |
| C | C | C | A | T | C | T | C |
| C | C | C | A | T | C | T | C |
| C | T | C | A | T | C | T | C |
| C | T | C | A | T | C | T | C |
| C | T | C | A | T | C | T | C |

*o = observed; i = inferred

TABLE 8

GSTO2 Haplotypes for Mexican-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 60.70% | o | D | T | G | C | C | G | G | C | C | T | G | G | G |
| 16.70% | o | D | T | G | C | C | G | G | C | C | T | G | A | T |
| 6.84% | o | D | T | G | C | C | G | G | C | C | T | G | G | G |
| 3.51% | i | D | T | G | C | C | G | G | C | C | T | G | A | T |
| 1.67% | i | D | T | G | C | C | G | G | C | C | T | G | G | T |
| 1.49% | i | D | T | G | C | C | G | G | C | C | T | G | A | T |

| 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) | Intron1 (+52) |
|---|---|---|---|---|---|---|---|---|---|---|---|---|---|---|
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |
| C | A | D | C | C | A | C | C | G | A | G | T | A | C | A |

| Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) | Intron1 (−185) | Intron1 (−19) |
|---|---|---|---|---|---|---|---|---|---|---|---|---|---|---|
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | C | T | T | D | A | A | A | G | C | A | T |
| G | I | G | T | T | T | T | D | A | A | A | G | T | A | T |
| G | I | G | T | C | T | T | D | A | A | A | G | C | A | T |

| Intron1 (−12) | Exon2 (−183) | Intron2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) | Intron6 (−55) | Intron6 (−21) | Exon7 (+591) |
|---|---|---|---|---|---|---|---|---|---|---|---|---|---|---|
| G | A | C | G | T | C | A | G | A | A | T | C | C | C | G |
| G | G | C | G | C | C | A | G | G | G | T | C | C | C | G |
| G | A | C | G | C | C | A | G | A | A | T | C | C | C | G |
| G | A | C | G | T | C | A | G | A | A | T | C | C | C | G |
| G | A | C | G | C | C | C | G | G | G | T | C | C | C | G |
| G | A | C | G | C | C | A | G | A | A | T | C | C | C | G |

| Exon7 (+630) | 3'FR (+1038) | 3'FR (+1080) | 3'FR (+1243) | 3'FR (+1343) | 3'FR (+1615) | 3'FR (+1649) | 3'FR (+1724) |
|---|---|---|---|---|---|---|---|
| C | C | C | A | T | C | T | C |
| C | C | C | A | T | C | T | C |
| C | C | C | A | T | C | T | C |
| C | C | C | A | T | C | T | C |
| C | C | C | A | T | C | T | C |
| C | C | C | A | T | C | T | C |

*o = observed; i = inferred

TABLE 9

Summary of GSTO2 haplotypes

| | AA | CA | HCA | MA | 5'FR (−2012) | 5'FR (−1785) | 5'FR (−1771) | 5'FR (−1664) | 5'FR (−1598) | 5'FR (−1576) | 5'FR (−1566) | 5'FR (−1357) | 5'FR (−1189) | 5'FR (−1105) | 5'FR (−1102) |
|---|---|---|---|---|---|---|---|---|---|---|---|---|---|---|---|
| 1 | 0.17 | — | — | — | I | T | G | T | G | C | A | A | C | G | T |
| 2 | 0.14 | — | — | 0.01 | D | T | G | C | C | G | G | C | T | G | T |
| 3 | 0.07 | 0.22 | 0.13 | 0.16 | D | T | G | C | C | G | G | C | T | A | T |
| 4 | 0.05 | — | — | — | D | T | G | C | C | G | G | C | T | G | T |
| 5 | 0.04 | — | — | 0.01 | D | T | G | C | C | G | G | C | T | G | T |
| 6 | 0.03 | — | — | — | D | C | G | C | C | G | G | C | T | G | T |
| 7 | 0.03 | 0.01 | 0.01 | 0.01 | D | T | G | C | C | G | G | C | T | G | T |
| 8 | 0.03 | 0.01 | 0.01 | 0.01 | D | T | G | C | C | G | G | C | T | G | T |
| 9 | — | 0.03 | — | 0.01 | D | T | G | C | C | G | G | C | T | A | T |
| 10 | 0.03 | — | — | — | I | T | G | T | G | C | A | A | C | G | T |
| 11 | 0.02 | — | — | — | D | C | G | C | C | G | G | C | T | G | T |
| 12 | 0.02 | — | — | — | D | T | G | C | C | G | G | C | T | G | T |
| 13 | — | — | 0.02 | 0.01 | D | T | G | C | C | G | G | C | T | G | T |
| 14 | 0.02 | — | — | — | D | T | G | C | C | G | G | C | T | G | T |
| 15 | 0.01 | — | — | — | D | T | C | C | C | G | G | C | T | A | T |
| 16 | — | — | 0.02 | — | D | T | G | C | C | G | G | C | T | A | T |

TABLE 9-continued

Summary of GSTO2 haplotypes

| | | | | | | | | | | | | | | |
|---|---|---|---|---|---|---|---|---|---|---|---|---|---|---|
| 17 | 0.14 | 0.5 | 0.55 | 0.61 | D | T | G | C | C | G | G | C | T | G | G |
| 18 | 0.03 | — | 0.06 | — | D | T | G | C | C | G | G | C | T | G | G |
| 19 | 0.03 | 0.1 | 0.12 | 0.07 | D | T | G | C | C | G | G | C | T | G | G |
| 20 | — | 0.01 | — | — | D | T | G | C | C | G | G | C | T | G | G |

| | 5'FR (−1009) | 5'FR (−781) | 5'FR (−730) | 5'FR (−637) | 5'FR (−634) | Exon1 (−530) | Exon1 (−463) | Exon1 (−450) | Exon1 (−293) | Intron1 (+311) | Intron1 (+402) | Intron1 (+426) | Intron1 (+435) | Intron1 (+1694) | Intron1 (+2003) |
|---|---|---|---|---|---|---|---|---|---|---|---|---|---|---|---|
| 1 | T | C | I | T | G | G | A | C | A | A | C | T | T | A | G |
| 2 | C | A | D | C | C | C | G | A | A | G | C | T | T | A | A |
| 3 | C | A | D | C | C | C | G | A | A | G | C | T | T | A | A |
| 4 | C | A | D | C | C | C | G | A | A | G | C | T | T | A | A |
| 5 | C | A | D | C | C | C | G | A | A | G | C | T | T | G | A |
| 6 | C | A | D | C | C | C | G | A | T | G | C | C | T | A | A |
| 7 | C | A | D | C | C | C | G | A | A | G | T | T | T | A | A |
| 8 | C | A | D | C | C | C | G | A | A | G | T | T | T | A | A |
| 9 | C | A | D | C | C | C | G | A | A | G | C | T | T | A | A |
| 10 | T | C | I | T | G | G | A | C | A | A | C | T | T | A | G |
| 11 | C | A | D | C | C | C | G | A | T | G | C | C | T | A | A |
| 12 | C | A | D | C | C | C | G | A | A | G | C | T | A | A | A |
| 13 | C | A | D | C | C | C | G | A | A | G | C | T | T | A | A |
| 14 | C | A | D | C | C | C | G | A | A | G | C | T | T | A | A |
| 15 | C | A | D | C | C | C | G | A | A | G | C | T | T | A | A |
| 16 | C | A | D | C | C | C | G | A | A | G | C | T | T | A | A |
| 17 | C | A | D | C | C | C | G | A | A | G | C | T | T | A | A |
| 18 | C | A | D | C | C | C | G | A | A | G | C | T | T | A | A |
| 19 | C | A | D | C | C | C | G | A | A | G | C | T | T | A | A |
| 20 | C | A | D | C | C | C | G | A | A | G | C | T | T | A | A |

| | Intron1 (+2168) | Intron1 (−1131) | Intron1 (−185) | Exon2 (−183) | Exon3 (+121) | Intron4 (+20) | Exon5 (+389) | Exon5 (+424) | Intron5 (+74) | Exon6 (+472) | Intron6 (−21) | Exon7 (+591) | Exon7 (+630) | 3' FR (+1038) | 3'FR (+1343) |
|---|---|---|---|---|---|---|---|---|---|---|---|---|---|---|---|
| 1 | G | C | A | A | G | C | G | G | G | C | C | G | C | C | T |
| 2 | A | C | A | A | G | C | G | G | G | C | C | G | C | C | T |
| 3 | G | C | A | G | G | C | G | G | G | C | C | G | C | C | T |
| 4 | G | C | A | A | G | C | G | G | G | C | C | G | C | C | T |
| 5 | G | C | A | A | G | C | G | G | G | C | C | G | T | C | T |
| 6 | G | C | G | A | G | C | G | G | G | C | C | G | T | C | T |
| 7 | G | T | A | A | G | C | G | G | G | C | C | G | C | C | T |
| 8 | G | T | A | A | G | C | G | G | G | C | C | G | C | C | T |
| 9 | G | C | A | A | G | T | G | A | A | C | C | G | C | C | T |
| 10 | G | C | A | A | G | C | G | G | G | C | T | G | C | C | G |
| 11 | G | C | G | A | G | C | G | G | G | C | C | T | T | T | T |
| 12 | A | C | A | A | G | C | G | G | G | C | C | T | C | T | T |
| 13 | A | C | A | A | G | C | G | G | G | C | C | T | C | T | T |
| 14 | A | C | A | A | G | C | G | G | G | C | C | T | C | T | G |
| 15 | G | C | A | G | A | C | G | G | G | C | C | T | C | T | T |
| 16 | G | C | A | G | G | C | A | G | G | C | C | G | C | C | T |
| 17 | G | C | A | A | G | T | G | A | A | C | C | G | C | C | T |
| 18 | G | C | A | A | G | T | G | A | A | C | T | C | C | T | T |
| 19 | G | C | A | A | G | C | G | A | A | C | C | G | C | C | T |
| 20 | G | C | A | A | G | C | G | A | A | A | C | G | C | C | T |

Example 4

Immunoreactivity of GSTO2 Allozymes

As an initial step in the study of the possible functional implications of nonsynonymous cSNPs in the GSTO2 gene, expression constructs were created for all variant allozymes, and those constructs were used to transfect COS-1 cells. This mammalian cell line was transfected to ensure the presence of mammalian post-translational modification and the mammalian machinery for protein degradation. The GSTO2 expression constructs were cotransfected with β-galactosidase to make it possible to correct for variations in transfection efficiency. The antibodies for GSTO2 were directed against peptides that did not include any of the genetically variant amino acids. When GSTO2 constructs were transiently expressed in COS-1 cells, levels of the Cys130Tyr13 and Leu158Ile allozymes, as well as the double variant Asn142Asp/Leu 158Ile allozyme, were strikingly reduced. The Val41Ile and Asn142Asp allozymes were expressed at approximately 80% of the level of the WT allozyme (Table 10). The GSTO2 antibody cross-reacted with a protein in the COS-1 cells with a molecular mass slightly higher than that for recombinant GSTO2.

Attempts were made to complement expression studies with parallel assays of level of enzyme activity, but the assays currently available for GSTO2 activity—assays that have been used to study purified, bacterially expressed protein (Schmuck et al. (2005) *Pharmacogenet Genomics* 15:493-

TABLE 10

GSTO2 immunoreactive protein levels

| | |
|---|---|
| WT | 100 ± 2.3 |
| Val41Ile | 82.8 ± 1.6 |
| Cys130Tyr | 49.4 ± 2.8 |
| Asn142Asp | 76.1 ± 3.0 |
| Leu158Ile | 17.3 ± 1.7 |
| Asn142Asp/Leu158Ile | 15.2 ± 2.5 |

Example 5

GSTO2 Degradation Studies

To investigate the mechanisms responsible for the striking decrease in expression of the GSTO2 Cys130Tyr and Leu158Ile allozymes, protein degradation studies were performed using RRL. Radioactive WT and variant GSTO2 allozymes were synthesized using "treated" RRL, and the recombinant proteins were incubated for various periods of time with "untreated" RRL and an ATP generating system to follow the time course of protein degradation. The CYS130Tyr, Leu158Ile, and Asn142Asp/Leu158Ile allozymes were degraded much more rapidly than WT GSTO2, with Leu158Ile and Asn142Asp/Leu158Ile being degraded more rapidly than Cys130Tyr (FIG. 3). After 24 hours, 26% of Cys130Tyr, 6.6% of Leu158Ile, 5.6% of Asn142Asp/Leu158Ile, and 73% of the WT protein remained. Therefore, accelerated degradation appeared to be responsible, at least in part, for differences in levels of the GSTO2 variant allozymes after expression in COS-1 cells.

Example 6

Activity and Substrate Kinetics of GSTO2 Allozymes

Cell homogenate preparations containing recombinant GSTO2 allozymes, prepared as described in Example 1, are used to assess catalytic activity. The resulting activities are adjusted to a percentage of the WT GSTO2 enzyme activity. To determine whether alterations in activity of the GSTO2 variants might be related to quantity of immunoreactive enzyme protein, quantitative Western blot analyses are conducted.

Alterations in amino acid sequence can alter enzyme substrate affinity and/or catalytic efficiency. Substrate kinetic studies are conducted to determine whether the allozymes differ from the WT GSTO2 protein in these aspects. A series of DHA concentrations are used to estimate apparent $K_m$ values for recombinant wild type GSTO2 and for the variant allozymes.

Example 7 mRNA Levels of GSTO2 Allozymes

RT-PCR was used to determine whether differences in protein levels were due to differences in mRNA levels. To evaluate the mRNA level after transient expression of GSTO2 WT and one or more GSTO allozymes, RT-PCR is performed using mRNA isolated from transfected COS-1 cells. β-Galactosidase is used to correct for transfection efficiency and also as an internal control for RT-PCR.

Example 8

Reporter Assays

Luciferase reporter assays are conducted to determine whether polymorphisms in the 5'-FR affect transcription of GSTO2 allozymes. Reporter gene constructs including commonly occurring haplotypes (e.g., haplotypes with an allele frequency greater than 3%) are created within the first 1 kb upstream of the translation initiation codon. These constructs are transfected into primary cells or cell lines such as liver, kidney, skeletal muscle, heart, lung, cervix, ovary, or prostate cells. After incubation for 48 hours, cells are harvested and lysed, and luciferase activity is measured using a dual-luciferase assay system.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting of a variant glutathione S-transferase omega 2 (GSTO2) nucleic acid sequence, wherein said variant GSTO2 nucleic acid sequence is selected from the group consisting of:
   a) at least fifteen contiguous nucleotides of SEQ ID NO:8, wherein said sequence includes nucleotide 121, 389, or 472 of SEQ ID NO:8, with the proviso that the nucleotide at position 121 is adenine, the nucleotide at position 389 is adenine, or the nucleotide at position 472 is adenine; and
   b) the full-length complement of a).

2. The isolated nucleic acid of molecule of claim 1, wherein said isolated nucleic acid molecule is from 15 to 100 nucleotides in length.

3. The isolated nucleic acid molecule of claim 1, wherein said isolated nucleic acid molecule is from 20 to 50 nucleotides in length.

4. An article of manufacture comprising a substrate, wherein said substrate comprises a population of the isolated variant GSTO2 nucleic acid molecules of claim 1.

5. The article of manufacture of claim 4, wherein said substrate comprises a plurality of discrete regions, wherein each said region comprises a population of isolated variant GSTO2 nucleic acid molecules, and wherein each said population of molecules comprises a different GSTO2 nucleotide sequence variant.

6. An isolated nucleic acid molecule consisting of a variant glutathione S-transferase omega 2 (GSTO2) nucleic acid and a label, wherein the sequence of said variant GSTO2 nucleic acid is selected from the group consisting of:
   a) at least fifteen contiguous nucleotides of SEQ ID NO:8, wherein said sequence includes nucleotide 121,389, or 472 of SEQ ID NO:8, with the proviso that the nucleotide at position 121 is adenine, the nucleotide at position 389 is adenine, or the nucleotide at position 472 is adenine; and
   b) the full-length complement of a).

7. The isolated nucleic acid of molecule of claim 6, wherein said isolated nucleic acid molecule is from 15 to 100 nucleotides in length.

8. The isolated nucleic acid molecule of claim 6, wherein said isolated nucleic acid molecule is from 20 to 50 nucleotides in length.

9. The isolated nucleic acid molecule of claim 6, wherein said label is a fluorescent moiety.

10. The isolated nucleic acid molecule of claim 6, wherein said label is biotin.

* * * * *